US012685561B2

(12) United States Patent

Cantor et al.

(10) Patent No.: US 12,685,561 B2

(45) Date of Patent: Jul. 21, 2026

(54) EXPANDABLE SURGICAL ACCESS PORT

(71) Applicant: Vycor Medical, Inc., Boca Raton, FL (US)

(72) Inventors: David Cantor, Rome (IT); Robert Schaefer, Riverside, CA (US)

(73) Assignee: Vycor Medical, Inc., Boca Raton, FL (US)

( * ) Notice: Subject to any disclaimer, the term of this patent is extended or adjusted under 35 U.S.C. 154(b) by 259 days.

(21) Appl. No.: 18/217,089

(22) Filed: Jun. 30, 2023

(65) Prior Publication Data

US 2024/0008896 A1 Jan. 11, 2024

Related U.S. Application Data

(60) Provisional application No. 63/358,651, filed on Jul. 6, 2022.

(51) Int. Cl.
*A61B 17/34* (2006.01)
*A61B 17/02* (2006.01)

(52) U.S. Cl.
CPC ...... *A61B 17/3423* (2013.01); *A61B 17/0206* (2013.01); *A61B 17/0293* (2013.01); *A61B 17/3462* (2013.01)

(58) Field of Classification Search
CPC ........................ A61B 17/0206; A61B 17/0293
USPC ............................................................ 606/1
See application file for complete search history.

(56) References Cited

U.S. PATENT DOCUMENTS

| | | | |
|---|---|---|---|
| 1,428,653 A | 9/1922 | Nick | |
| 1,849,701 A | 3/1932 | Allyn | |
| 2,769,441 A | 11/1956 | Abramson | |
| 2,922,415 A | 1/1960 | Campagna | |
| 3,417,746 A | 12/1968 | Moore | |
| 3,608,547 A | 9/1971 | Sato | |
| 3,626,471 A | 12/1971 | Florin | |
| 3,690,323 A | 9/1972 | Wortman et al. | |
| 3,766,910 A | 10/1973 | Lake | |
| 3,789,829 A | 2/1974 | Hasson | |
| 3,882,855 A | 5/1975 | Schulte et al. | |
| 3,888,117 A | 6/1975 | Lewis | |
| 4,263,900 A | 4/1981 | Nicholson | |
| 4,300,541 A | 11/1981 | Burgin | |
| 4,312,353 A | 1/1982 | Shahbabian | |
| 4,386,602 A | 6/1983 | Sheldon et al. | |

(Continued)

FOREIGN PATENT DOCUMENTS

| | | |
|---|---|---|
| CN | 101720207 A | 6/2010 |
| CN | 201879787 U | 6/2011 |

(Continued)

OTHER PUBLICATIONS

Office Action issued in U.S. Appl. No. 16/872,868, dated Jul. 2, 2024 (10 pages).

(Continued)

*Primary Examiner* — Nicole F Johnson

(74) *Attorney, Agent, or Firm* — CM Law, LLP

(57) ABSTRACT

An expandable surgical access port having movable arms and a membrane on the arms. The arms are movable by a mechanism that operates without moving in the longitudinal direction, and may include position indicators, slots for lights and electrical wires through the arms, and other features. A method for making a surgical access port is also provided.

28 Claims, 27 Drawing Sheets

(56)         References Cited

U.S. PATENT DOCUMENTS

| | | | |
|---|---|---|---|
| 4,502,468 A | 3/1985 | Burgin |
| 4,585,438 A | 4/1986 | Makler |
| 4,636,199 A | 1/1987 | Victor |
| 4,638,798 A | 1/1987 | Sheldon et al. |
| 4,742,815 A | 5/1988 | Ninan et al. |
| 4,931,039 A | 6/1990 | Coe et al. |
| 4,945,896 A | 8/1990 | Gade |
| 5,052,373 A | 10/1991 | Michelson |
| 5,135,526 A | 8/1992 | Zinnanti et al. |
| 5,160,323 A | 11/1992 | Andrew |
| 5,161,534 A | 11/1992 | Berthiaume |
| 5,183,464 A | 2/1993 | Dubrul et al. |
| 5,197,484 A | 3/1993 | Kornberg et al. |
| 5,230,623 A | 7/1993 | Guthrie et al. |
| 5,232,451 A | 8/1993 | Freitas et al. |
| 5,249,568 A | 10/1993 | Brefka et al. |
| 5,251,127 A | 10/1993 | Raab |
| 5,256,149 A | 10/1993 | Banik et al. |
| 5,271,380 A | 12/1993 | Riek et al. |
| 5,275,583 A | 1/1994 | Crainich |
| 5,284,130 A | 2/1994 | Ratliff |
| 5,305,203 A | 4/1994 | Raab |
| 5,320,611 A | 6/1994 | Bonutti et al. |
| 5,334,150 A | 8/1994 | Kaali |
| 5,356,421 A | 10/1994 | Castro |
| 5,376,076 A | 12/1994 | Kaali |
| 5,380,291 A | 1/1995 | Kaali |
| 5,409,453 A | 4/1995 | Lundquist et al. |
| 5,431,151 A | 7/1995 | Riek et al. |
| 5,431,676 A | 7/1995 | Dubrul et al. |
| 5,441,041 A | 8/1995 | Sauer et al. |
| 5,445,142 A | 8/1995 | Hassler |
| 5,467,762 A | 11/1995 | Sauer et al. |
| 5,509,893 A | 4/1996 | Pracas |
| 5,513,238 A | 4/1996 | Leber et al. |
| 5,540,711 A | 7/1996 | Kieturakis et al. |
| 5,551,947 A | 9/1996 | Kaali |
| 5,555,283 A | 9/1996 | Shui et al. |
| 5,562,696 A | 10/1996 | Nobles et al. |
| 5,569,160 A | 10/1996 | Sauer et al. |
| D377,093 S | 12/1996 | Michelson |
| 5,591,192 A | 1/1997 | Privitera et al. |
| 5,609,562 A | 3/1997 | Kaali |
| 5,658,236 A | 8/1997 | Sauer et al. |
| 5,662,111 A | 9/1997 | Cosman |
| 5,665,072 A | 9/1997 | Yoon |
| 5,676,673 A | 10/1997 | Ferre et al. |
| 5,685,820 A | 11/1997 | Riek et al. |
| 5,702,761 A | 12/1997 | DiChiara et al. |
| 5,738,628 A | 4/1998 | Sierocuk et al. |
| 5,748,703 A | 5/1998 | Cosman |
| 5,748,767 A | 5/1998 | Raab |
| 5,762,629 A | 6/1998 | Kambin |
| 5,778,043 A | 7/1998 | Cosman |
| 5,782,807 A | 7/1998 | Falvai et al. |
| 5,785,648 A | 7/1998 | Min |
| 5,792,044 A | 8/1998 | Foley et al. |
| 5,800,352 A | 9/1998 | Ferre et al. |
| 5,803,089 A | 9/1998 | Ferre et al. |
| 5,829,444 A | 11/1998 | Ferre et al. |
| 5,846,249 A | 12/1998 | Thompson |
| 5,848,967 A | 12/1998 | Cosman |
| 5,860,996 A | 1/1999 | Urban et al. |
| 5,873,822 A | 2/1999 | Ferre et al. |
| 5,891,157 A | 4/1999 | Day et al. |
| 5,902,272 A | 5/1999 | Eggers et al. |
| 5,921,992 A | 7/1999 | Costales et al. |
| 5,947,981 A | 9/1999 | Cosman |
| 5,967,970 A | 10/1999 | Cowan et al. |
| 5,967,980 A | 10/1999 | Ferre et al. |
| 5,971,997 A | 10/1999 | Guthrie et al. |
| 6,005,919 A | 12/1999 | Kooy et al. |
| 6,006,126 A | 12/1999 | Cosman |
| 6,007,481 A | 12/1999 | Riek et al. |
| 6,041,101 A | 3/2000 | Kooy et al. |
| 6,047,218 A | 4/2000 | Whayne et al. |
| 6,083,191 A | 7/2000 | Rose et al. |
| 6,093,145 A | 7/2000 | Berg et al. |
| 6,096,038 A | 8/2000 | Michelson |
| 6,120,465 A | 9/2000 | Guthrie et al. |
| 6,129,685 A | 10/2000 | Howard |
| 6,142,931 A | 11/2000 | Kaji et al. |
| 6,156,054 A | 12/2000 | Zadno-Azizi et al. |
| 6,159,178 A | 12/2000 | Sharkawy et al. |
| 6,167,295 A | 12/2000 | Cosman |
| 6,175,756 B1 | 1/2001 | Ferre et al. |
| 6,179,826 B1 | 1/2001 | Aebischer et al. |
| 6,214,017 B1 | 4/2001 | Stoddard et al. |
| 6,221,078 B1 | 4/2001 | Bylsma |
| 6,224,599 B1 | 5/2001 | Bayham et al. |
| 6,228,059 B1 | 5/2001 | Astarita |
| 6,236,875 B1 | 5/2001 | Bucholz et al. |
| 6,245,052 B1 | 6/2001 | Orth et al. |
| 6,256,859 B1 | 7/2001 | Stoddard et al. |
| 6,259,943 B1 | 7/2001 | Cosman et al. |
| 6,275,725 B1 | 8/2001 | Cosman |
| 6,277,069 B1 | 8/2001 | Gray |
| 6,278,766 B1 | 8/2001 | Kooy et al. |
| 6,283,912 B1 | 9/2001 | Hu et al. |
| 6,293,952 B1 | 9/2001 | Brosens et al. |
| 6,296,647 B1 | 10/2001 | Robionek et al. |
| 6,312,443 B1 | 11/2001 | Stone |
| 6,326,875 B1 | 12/2001 | Tuovinen |
| 6,331,180 B1 | 12/2001 | Cosman et al. |
| 6,341,231 B1 | 1/2002 | Ferre et al. |
| 6,351,659 B1 | 2/2002 | Vilsmeier |
| 6,351,661 B1 | 2/2002 | Cosman |
| 6,359,959 B1 | 3/2002 | Butler et al. |
| 6,364,832 B1 | 4/2002 | Propp |
| 6,371,964 B1 | 4/2002 | Vargas et al. |
| 6,374,135 B1 | 4/2002 | Bucholz |
| 6,383,191 B1 | 5/2002 | Zdeblick et al. |
| 6,405,072 B1 | 6/2002 | Cosman |
| 6,409,686 B1 | 6/2002 | Guthrie et al. |
| 6,416,520 B1 | 7/2002 | Kynast et al. |
| 6,425,859 B1 | 7/2002 | Foley et al. |
| 6,428,556 B1 | 8/2002 | Chin |
| 6,445,944 B1 | 9/2002 | Ostrovsky |
| 6,459,769 B1 | 10/2002 | Cosman |
| 6,461,330 B1 | 10/2002 | Miyagi |
| 6,478,028 B1 | 11/2002 | Paolitto et al. |
| 6,478,806 B2 | 11/2002 | McFarlane |
| 6,551,240 B2 | 4/2003 | Henzler |
| 6,565,574 B2 | 5/2003 | Michelson |
| 6,589,211 B1 | 7/2003 | Macleod |
| 6,595,917 B2 | 7/2003 | Nieto |
| 6,596,008 B1 | 7/2003 | Kambin |
| 6,599,292 B1 | 7/2003 | Ray |
| 6,602,227 B1 | 8/2003 | Cimino et al. |
| 6,605,036 B1 | 8/2003 | Wild |
| 6,613,038 B2 | 9/2003 | Bonutti et al. |
| 6,654,999 B2 | 12/2003 | Stoddard et al. |
| 6,662,036 B2 | 12/2003 | Cosman |
| 6,669,685 B1 | 12/2003 | Rizoiu et al. |
| 6,675,040 B1 | 1/2004 | Cosman |
| 6,685,630 B2 | 2/2004 | Sauer et al. |
| 6,730,021 B2 | 5/2004 | Vassiliades et al. |
| 6,761,687 B1 | 7/2004 | Doshi et al. |
| D495,053 S | 8/2004 | Laun |
| 6,863,674 B2 | 3/2005 | Kasahara et al. |
| 6,896,680 B2 | 5/2005 | Michelson |
| 6,942,634 B2 | 9/2005 | Odland |
| 7,081,089 B2 | 7/2006 | Bonadio et al. |
| 7,150,714 B2 | 12/2006 | Myles |
| 7,153,304 B2 | 12/2006 | Robie et al. |
| 7,182,729 B2 | 2/2007 | Abdelgany et al. |
| 7,235,084 B2 | 6/2007 | Skakoon et al. |
| 7,344,495 B2 | 3/2008 | Ravikumar et al. |
| 7,374,534 B2 | 5/2008 | Dalton |
| 7,435,219 B2 | 10/2008 | Kim |
| 7,449,011 B2 | 11/2008 | Wenchell et al. |
| 7,474,820 B2 | 1/2009 | Vayser et al. |
| 7,479,150 B2 | 1/2009 | Rethy et al. |
| 7,481,766 B2 | 1/2009 | Lee et al. |

(56) References Cited

U.S. PATENT DOCUMENTS

| | | |
|---|---|---|
| 7,510,524 B2 | 3/2009 | Vayser et al. |
| 7,513,869 B2 | 4/2009 | Branch et al. |
| 7,556,600 B2 | 7/2009 | Landry et al. |
| 7,594,888 B2 | 9/2009 | Raymond et al. |
| 7,645,232 B2 | 1/2010 | Shluzas |
| 7,686,492 B2 | 3/2010 | Vayser et al. |
| 7,691,120 B2 | 4/2010 | Shluzas et al. |
| 7,758,501 B2 | 7/2010 | Frasier et al. |
| 7,799,035 B2 | 9/2010 | Krueger et al. |
| 7,850,608 B2 | 12/2010 | Hamada |
| 7,892,174 B2 | 2/2011 | Hestad et al. |
| 7,931,589 B2 | 4/2011 | Cohen et al. |
| 7,935,053 B2 | 5/2011 | Karpowicz et al. |
| 7,981,031 B2 | 7/2011 | Frasier et al. |
| 7,988,625 B2 | 8/2011 | Abdelgany et al. |
| 8,062,217 B2 | 11/2011 | Boucher et al. |
| 8,105,236 B2 | 1/2012 | Malandain et al. |
| 8,152,721 B2 | 4/2012 | Michaeli et al. |
| 8,231,570 B2 | 7/2012 | Ortiz et al. |
| 8,291,781 B2 | 10/2012 | Guerrero et al. |
| 8,353,826 B2 | 1/2013 | Weiman |
| 8,360,970 B2 | 1/2013 | Mangiardi |
| 8,386,052 B2 | 2/2013 | Harris et al. |
| 8,409,083 B2 | 4/2013 | Mangiardi |
| 8,409,089 B2 | 4/2013 | Michaeli et al. |
| 8,454,504 B2 | 6/2013 | Michaeli et al. |
| 8,517,935 B2 | 8/2013 | Marchek et al. |
| 8,523,769 B2 | 9/2013 | Fehling et al. |
| 8,550,995 B2 | 10/2013 | Frasier et al. |
| 8,574,154 B2 | 11/2013 | Loftus et al. |
| 8,579,809 B2 | 11/2013 | Parker |
| 8,602,984 B2 | 12/2013 | Raymond et al. |
| 8,608,650 B2 | 12/2013 | Mangiardi |
| 8,608,769 B2 | 12/2013 | Kahle et al. |
| 8,622,897 B2 | 1/2014 | Raymond et al. |
| 8,663,102 B2 | 3/2014 | Michaeli et al. |
| 8,679,088 B2 | 3/2014 | Abrahams |
| 8,821,394 B2 | 9/2014 | Hawkins et al. |
| 8,876,687 B2 | 11/2014 | Jones et al. |
| 8,894,573 B2 | 11/2014 | Loftus et al. |
| 8,956,285 B2 | 2/2015 | Gephart et al. |
| 8,974,380 B2 | 3/2015 | Michaeli et al. |
| 8,992,425 B2 | 3/2015 | Karpowicz et al. |
| 8,992,558 B2 | 3/2015 | Stone et al. |
| 9,028,402 B2 | 5/2015 | Wenchell |
| 9,161,820 B2 | 10/2015 | Mark et al. |
| 9,179,903 B2 | 11/2015 | Cianfrani et al. |
| 9,186,175 B2 | 11/2015 | Mark et al. |
| 9,216,015 B2 | 12/2015 | Wilson |
| 9,265,523 B2 | 2/2016 | Mark et al. |
| 9,307,969 B2 | 4/2016 | Novak et al. |
| 9,387,010 B2 | 7/2016 | Mark et al. |
| 9,492,065 B2 | 11/2016 | Tesar et al. |
| 9,521,997 B2 | 12/2016 | Hawkins et al. |
| 9,572,560 B2 | 2/2017 | Mast et al. |
| 9,579,121 B2 | 2/2017 | Mark et al. |
| 9,693,761 B2 | 7/2017 | Fedorov et al. |
| 9,757,147 B2 | 9/2017 | Mark et al. |
| 9,770,261 B2 | 9/2017 | Mark et al. |
| 9,808,231 B2 | 11/2017 | Miraki et al. |
| 9,848,864 B2 | 12/2017 | Lauchner |
| 9,855,027 B2 | 1/2018 | Ziolo et al. |
| 9,949,814 B2 | 4/2018 | Alexander et al. |
| 9,980,745 B2 | 5/2018 | Burg et al. |
| 10,016,214 B2 | 7/2018 | Sawalhe et al. |
| 10,022,520 B2 | 7/2018 | Mark |
| 10,080,561 B2 | 9/2018 | Lauchner |
| 10,188,376 B2 | 1/2019 | Miraki et al. |
| 10,258,316 B2 | 4/2019 | Rhad et al. |
| 10,327,748 B2 | 6/2019 | Gifford et al. |
| 10,376,258 B2 | 8/2019 | Cantor et al. |
| 10,543,016 B2 | 1/2020 | Cantor et al. |
| 10,687,797 B2 | 6/2020 | Stone et al. |
| 11,191,532 B2 | 12/2021 | Popejoy et al. |
| 2001/0010002 A1 | 7/2001 | Michelson |
| 2001/0011175 A1 | 8/2001 | Hunter et al. |
| 2001/0027271 A1 | 10/2001 | Franck et al. |
| 2001/0037050 A1 | 11/2001 | Lemperle |
| 2002/0022764 A1 | 2/2002 | Smith et al. |
| 2002/0151769 A1 | 10/2002 | Kim |
| 2002/0161366 A1 | 10/2002 | Robie et al. |
| 2003/0040753 A1 | 2/2003 | Daum et al. |
| 2003/0073934 A1 | 4/2003 | Putz |
| 2003/0139648 A1 | 7/2003 | Foley et al. |
| 2003/0145865 A1 | 8/2003 | Sterman et al. |
| 2003/0233115 A1 | 12/2003 | Eversull et al. |
| 2004/0024291 A1 | 2/2004 | Zinkel |
| 2004/0059375 A1 | 3/2004 | Ginn et al. |
| 2004/0068172 A1 | 4/2004 | Nowinski et al. |
| 2004/0097792 A1 | 5/2004 | Moll et al. |
| 2004/0102804 A1 | 5/2004 | Chin |
| 2004/0186346 A1 | 9/2004 | Smith et al. |
| 2004/0230100 A1 | 11/2004 | Shluzas |
| 2005/0085841 A1 | 4/2005 | Eversull et al. |
| 2005/0273132 A1 | 12/2005 | Shluzas et al. |
| 2005/0277811 A1 | 12/2005 | Richards et al. |
| 2006/0041270 A1 | 2/2006 | Lenker et al. |
| 2006/0122462 A1 | 6/2006 | Roth et al. |
| 2006/0212062 A1 | 9/2006 | Farascioni |
| 2006/0229636 A1 | 10/2006 | Woodburn et al. |
| 2006/0287583 A1 | 12/2006 | Mangiardi |
| 2007/0038033 A1 | 2/2007 | Jones et al. |
| 2007/0060939 A1 | 3/2007 | Lancial et al. |
| 2007/0129747 A1 | 6/2007 | Dorman |
| 2007/0135679 A1 | 6/2007 | Hunt et al. |
| 2007/0208366 A1 | 9/2007 | Pellegrino et al. |
| 2007/0232874 A1 | 10/2007 | Ince |
| 2008/0058590 A1 | 3/2008 | Saadat et al. |
| 2008/0100061 A1 | 5/2008 | Sage et al. |
| 2008/0109026 A1 | 5/2008 | Kassam |
| 2008/0119693 A1 | 5/2008 | Makower et al. |
| 2009/0048622 A1 | 2/2009 | Wilson |
| 2009/0306586 A1 | 12/2009 | Ross et al. |
| 2009/0312611 A1 | 12/2009 | Mangiardi |
| 2010/0010315 A1 | 1/2010 | Mangiardi |
| 2010/0160947 A1 | 6/2010 | Akyuz et al. |
| 2010/0274094 A1 | 10/2010 | Abdelgany et al. |
| 2011/0118710 A1 | 5/2011 | Begemann et al. |
| 2011/0160672 A1 | 6/2011 | Boebel et al. |
| 2011/0196205 A1 | 8/2011 | Hathaway et al. |
| 2011/0301423 A1 | 12/2011 | Koros et al. |
| 2011/0301424 A1 | 12/2011 | Steigerwald |
| 2012/0016204 A1 | 1/2012 | Bastia |
| 2012/0016316 A1 | 1/2012 | Zhuang et al. |
| 2012/0022575 A1 | 1/2012 | Mire et al. |
| 2012/0035424 A1 | 2/2012 | Schulte |
| 2012/0071748 A1 | 3/2012 | Mark et al. |
| 2012/0101341 A1 | 4/2012 | Malandain et al. |
| 2012/0253375 A1 | 10/2012 | Mark et al. |
| 2012/0265058 A1 | 10/2012 | Carrascosa |
| 2012/0289816 A1 | 11/2012 | Mark et al. |
| 2013/0066154 A1 | 3/2013 | Mangiardi |
| 2013/0066157 A1 | 3/2013 | Guralnik et al. |
| 2013/0090680 A1 | 4/2013 | Akyuz et al. |
| 2013/0102851 A1 | 4/2013 | Mark et al. |
| 2013/0102886 A1 | 4/2013 | Mark et al. |
| 2013/0204095 A1 | 8/2013 | Mark et al. |
| 2013/0204287 A1 | 8/2013 | Mark et al. |
| 2013/0211200 A1 | 8/2013 | Brannon |
| 2013/0245381 A1 | 9/2013 | Dang et al. |
| 2014/0107426 A1 | 4/2014 | Wilson |
| 2014/0171873 A1 | 6/2014 | Mark et al. |
| 2014/0187922 A1 | 7/2014 | Mark et al. |
| 2015/0223832 A1 | 8/2015 | Swaney et al. |
| 2016/0015374 A1 | 1/2016 | Gifford et al. |
| 2016/0015375 A1 | 1/2016 | Kaiser et al. |
| 2016/0317182 A1 | 11/2016 | Mark et al. |
| 2017/0000579 A1 | 1/2017 | Mark et al. |
| 2017/0209133 A1 | 7/2017 | Ciulla et al. |
| 2017/0215860 A1 | 8/2017 | Trimarche et al. |
| 2017/0265893 A1 | 9/2017 | Mark et al. |
| 2017/0265894 A1 | 9/2017 | Mark et al. |
| 2017/0360291 A1 | 12/2017 | Chegini et al. |
| 2018/0014890 A1 | 1/2018 | Stanton et al. |

(56)                  References Cited

U.S. PATENT DOCUMENTS

| | | | |
|---|---|---|---|
| 2018/0085182 A1 | 3/2018 | Ewers et al. | |
| 2018/0125603 A1 | 5/2018 | Cantor et al. | |
| 2018/0161024 A1 | 6/2018 | Davis et al. | |
| 2019/0223856 A1* | 7/2019 | Cantor | A61B 17/3421 |
| 2019/0247087 A1 | 8/2019 | Brown et al. | |
| 2020/0179003 A1 | 6/2020 | Widenhouse et al. | |
| 2020/0275919 A1 | 9/2020 | Stone et al. | |
| 2021/0033827 A1 | 2/2021 | Kim et al. | |
| 2021/0085363 A1 | 3/2021 | Mark et al. | |
| 2021/0236161 A1 | 8/2021 | Mark et al. | |
| 2021/0393290 A1 | 12/2021 | Baril et al. | |
| 2021/0401457 A1 | 12/2021 | Schaefer | |
| 2023/0011661 A1 | 1/2023 | Mark et al. | |

FOREIGN PATENT DOCUMENTS

| | | | |
|---|---|---|---|
| CN | 103619264 A | 3/2014 | |
| CN | 203724147 U | 7/2014 | |
| DE | 102005032197 A1 | 1/2007 | |
| JP | 02289221 A | 11/1990 | |
| JP | 05344978 A | 12/1993 | |
| JP | 09224943 | 9/1997 | |
| JP | 2000287915 A | 10/2000 | |
| JP | 2003153907 | 5/2003 | |
| RU | 45928 U1 | 6/2005 | |
| RU | 55570 U1 | 8/2006 | |
| SU | 131027 A1 | 3/1959 | |
| SU | 349136 | 9/1972 | |
| SU | 585840 A1 | 12/1977 | |
| SU | 1521465 A1 | 11/1989 | |
| WO | 9628083 A1 | 9/1996 | |
| WO | 0143627 A1 | 6/2001 | |
| WO | 2001043627 A1 | 6/2001 | |
| WO | 2006017507 A2 | 2/2006 | |
| WO | 2006050047 A2 | 5/2006 | |
| WO | 2006050225 A2 | 5/2006 | |
| WO | 2010076555 A1 | 7/2010 | |
| WO | 2013063027 A1 | 5/2013 | |
| WO | 2014137530 A1 | 9/2014 | |
| WO | 2014137551 A1 | 9/2014 | |
| WO | 2018218992 A1 | 12/2018 | |

OTHER PUBLICATIONS

"Neuronavigation", from Wikipedia, dated Jul. 30, 2014, 2 pages.
Alberti et al., "Frameless Navigation and Endoscopy", J. Neurosurg., Sep. 2001;95(3), pp. 541-543.
Alexander et al., "Chapter 20: Stereotactic Frame Systems: The COMPASS System", Advanced Neurosurgical Navigation, 1999, pp. 267-277.
Amstutz et al., "A-Mode Ultrasound-Based Registration in Computer-Aided Surgery of the Skull", Arch. Otolaryngol Head Neck Surg., 2003, 129(12), pp. 1310-1316.
Andrews et al., "A Review of Brain Retraction and Recommendations for Minimizing Intraoperative Brain Injury", Neurosurgery, 1993, 33(6), pp. 1052-1063.
Burtscher et al., "Neuroendoscopy Based on Computer Assisted Adjustment of the Endoscope Holder in the Laboratory", Minimum Invasive Neurosurgery, 2003, 46, pp. 208-214.
Canadian Examination Report for Canadian Application No. 3,043,182, dated Sep. 12, 2022, 9 pages.
Chinese Office Action for Chinese Application No. 201580031654.3, dated Sep. 30, 2017, 18 pages.
Chinese Office Action for Chinese Application No. 201780082607.0, dated Dec. 27, 2021, with translation, 19 pages.
Decision for Rejection for Japanese Application No. 2009-539227, dated May 31, 2013, 8 pages.
Del Ray Medical Center Press Release, "Advanced Neuroscience Network Brings New Innovations in Neurosurgery to South Florida", May 13, 2015, pp. 1-6.
Ding et al., "Endoport-assisted Microsurgical Resection of Cerebral Cavernous Malformations", J. Clin. Neurosci., Jun. 2015, vol. 22, No. 6, pp. 1025-1029. (Abstract only).

Eldeib et al., "Rigid Neuroendoscope Navigation System for Minimally Invasive Surgery", Engineering in Medicine and Biology, 1999, 1 page. (Abstract only).
Engh et al., "NeuroendoportSM Surgery Facilitates Removal of Hard-to-Reach Brain Tumors", Neurosurgery News, Spring 2009, vol. 10, No. 2, 8 pages.
European Communication for European Application No. 15 793 215.3, dated Jan. 15, 2018, 4 pages.
European Communication for European Application No. 17 868 180.5, dated Jun. 17, 2020, 1 page.
Extended European Communication for European Application No. 06 840 022.5, dated Mar. 26, 2013, 7 pages.
Extended European Communication for European Application No. 15 793 215.3, dated Mar. 24, 2017, 6 pages.
Extended European Communication for European Application No. 17 868 180.5, dated May 29, 2020, 5 pages.
Extended European Search Report for European Application No. 23 165 657.0, dated Jun. 16, 2023, 5 pages.
Final Office Action for U.S. Appl. No. 14/134,360, dated Jan. 12, 2016, 13 pages.
Final Office Action for U.S. Appl. No. 14/727,374, dated Nov. 23, 2016, 14 pages.
Final Office Action for U.S. Appl. No. 15/372,890, dated Feb. 21, 2019, 15 pages.
Fukamachi et al., "Postoperative Intracerebral Hemorrhages: A Survey of Computed Tomographic Findings After 1074 Intracranial Operations", Surg. Neurol., Jun. 1985, 23(6), pp. 575-580. 2019.
Greenfield et al., "Stereotactic Minimally Invasive Tubular Retractors System for Deep Brain Lesions", Neurosurgery, 2008, 63(4), pp. 334-339. (Abstract only).
Gumprecht et al., "Neuroendoscopy Combined with Frameless Neuronavigation", British Journal of Neurosurgery, 2000, 14(2), pp. 129-131.
Hellwig et al., "Neuroendoscopic Treatment for Colloid Cysts of the Third Ventricle: The Experience of a Decade", Neurosurgery, Mar. 2003, vol. 52, Iss. 3, pp. 525-533.
Herrera et al., "Use of Transparent Plastic Tubular Retractor in Surgery for Deep Brain Lesions: A Case Series", Surgical Technology International XIX, published in 2010, pp. 1-4.
Hilton et al., "METRx Microdiscectomy Surgical Technique", Medtronic Sofamor Danek, 2001, 20 pages.
International Preliminary Report on Patentability for International Application No. PCT/US2006/061246, dated Jun. 3, 2009, 5 pages.
International Preliminary Report on Patentability for International Application No. PCT/US2015/030528, dated Nov. 15, 2016, 7 pages.
International Preliminary Report on Patentability for International Application No. PCT/US2017/060373, dated May 7, 2019, 8 pages.
International Search Report and Written Opinion for International Application No. PCT/US2015/030528, dated Aug. 14, 2015, 8 pages.
International Search Report and Written Opinion for International Application No. PCT/US2017/060373, dated Jan. 23, 2018, 8 pages.
International Search Report and Written Opinion for International Application No. PCT/US2022/043282, dated Nov. 21, 2022, 11 pages.
International Search Report and Written Opinion for International Application No. PCT/US2006/061246, dated Sep. 11, 2007, 5 pages.
Japanese Notice of Reasons for Rejection for Japanese Application No. 2019-545728, mailed Sep. 7, 2021, with translation, 7 pages.
K043602 510(k) Summary, Feb. 23, 2005, 5 pages.
K060973 510(k) Summary, Jul. 26, 2006, 6 pages.
Kelly et al., "The Stereotaxic Retractor in Computer-Assisted Stereotaxic Microsurgery", J. Neurosurgery, 1988, 69, pp. 301-306.
Konen et al., "An Image-based Navigation Support System for Neuroendoscopic Surgery", in: R. Ahlers (ed.), 5. Symposium Bildverarbeitung, 1997, Technische Akademie Esslingen, 8 pages.
Kubo et al., "A Newly Designed Disposable Introducer Sheath for a Ventricular Fiberscope", Minim Invasive Neurosurg, 2004, 47(2), pp. 124-126.

(56) References Cited

OTHER PUBLICATIONS

Lemole et al., "Cranial Application of Frameless Stereotaxy", Barrow Neurological Institute, Barrow Quarterly, 2001, vol. 17, No. 1, 12 pages.

McInerney et al., "Frameless Stereotaxy of the Brain", The Mount Sinai Journal of Medicine, Sep. 2000, vol. 67, No. 4, pp. 300-310.

Mettler et al., "Optical Trocar Systems: Laparoscopic Entry and its Complications (A Study of Cases in Germany)", Gynaecological Endoscopy, Dec. 1999, vol. 8, Iss. 6, pp. 383-389. (Abstract only).

Nagatani et al., "High Definition Exoscope System for Microneurosurgery: Use of an Exoscope in Combination with Tubular Retraction and Frameless Neuronavigation for Microsurgical Resection of Deep Brain Lesions", No Shinkei Geka, Jul. 2015, 43(7), pp. 611-617.

NICO Corporation Press Release, "NICO Corporation Gains Market Expansion after Multiple Published Clinical Articles Support Access Technology for Deep Brain Lesions", May 5, 2015, 2 pages.

Non Final Office Action for U.S. Appl. No. 14/727,374, dated Jul. 22, 2016, 35 pages.

Non Final Office Action for U.S. Appl. No. 14/711,305, dated Dec. 7, 2016, 42 pages.

Non Final Office Action for U.S. Appl. No. 14/727,361, dated Jul. 14, 2016, 31 pages.

Written Opinion of the International Searching Authority in application No. PCT/US2023/026683, Mailed Dec. 14, 2023.

Office Action issued in U.S. Appl. No. 17/473,282, dated Aug. 5, 2024 (25 pages).

Non Final Office Action for U.S. Appl. No. 15/004,332, dated Feb. 14, 2017, 13 pages.

Non Final Office Action for U.S. Appl. No. 15/004,332, dated Nov. 18, 2016, 26 pages.

Non Final Office Action for U.S. Appl. No. 15/613,904, dated Oct. 5, 2018, 34 pages.

Non Final Office Action for U.S. Appl. No. 16/369,848, dated Feb. 1, 2021, 42 pages.

Non Final Office Action for U.S. Appl. No. 16/369,862, dated Oct. 13, 2020, 27 pages.

Notice of Allowance for U.S. Appl. No. 13/674,507, mailed Dec. 9, 2015, 7 pages.

Notice of Allowance for U.S. Appl. No. 14/134,360, mailed Mar. 11, 2016, 10 pages.

Notice of Allowance for U.S. Appl. No. 14/711,305, mailed Apr. 18, 2017, 11 pages.

Notice of Allowance for U.S. Appl. No. 14/727,361, mailed Sep. 21, 2016, 8 pages.

Notice of Allowance for U.S. Appl. No. 14/727,374, mailed Jan. 19, 2017, 9 pages.

Notice of Allowance for U.S. Appl. No. 15/004,332, mailed Jun. 14, 2017, 7 pages.

Notice of Allowance for U.S. Appl. No. 15/083,916, mailed Jan. 30, 2018, 12 pages.

Notice of Allowance for U.S. Appl. No. 15/083,940, mailed Jan. 22, 2018, 7 pages.

Notice of Allowance for U.S. Appl. No. 15/372,890, mailed Mar. 26, 2019, 8 pages.

Notice of Allowance for U.S. Appl. No. 15/613,904, mailed Feb. 8, 2019, 9 pages.

Notice of Allowance for U.S. Appl. No. 15/805,821, mailed Sep. 25, 2019, 9 pages.

O'Shaughnessy, P., "New Brain Tumor Technology Helps Man Who Took Two Bullets to the Head Return to Normal Life", Daily News, Jun. 19, 2011, 2 pages.

Office Action for U.S. Appl. No. 13/674,507, dated Jul. 27, 2015, 11 pages.

Office Action for U.S. Appl. No. 14/134,360, dated Jul. 7, 2015, 23 pages.

Ogura et al., "New Microsurgical Technique for Intraparenchymal Lesions of the Brain: Transcyclinder Approach", Aeta Neurochirurgica (Wein) 2006, 148, pp. 779-785.

Otsuki et al., "Stereotactic Guiding Tube for Open-System Endoscopy: A New Approach for the Stereotactic Endoscopic Resection of Intra-Axial Brain Tumors", Neurosurgery, 1990, 27(2), pp. 326-330.

Preliminary Amendment and Request for Interference for U.S. Appl. No. 14/134,360, dated Dec. 23, 2013, 3 pages.

Prevedello et al., "Vycor ViewSite TCR: Endoscope Guided Intraparenchimal Brain Tumor Ressection", Ohio State University Medical Center Minimally Invasive Neurosurgery, 2 pages.

Rampini et al., "Stereotactically Guided Endoscopy for the Treatment of Arachnoid Cysts", Pediatric Neurosurgery, 1998, 29(2), pp. 102-104. (Abstract only).

Raza et al., "Minimally Evasive Trans-Portal Resection of Deep Intracranial Lesions", Neurosurgery, vol. 54, Feb. 2011, pp. 1-7.

Recinos et al., "Use of Minimally Invasive Tubular Retraction System for Deep-seated Tumors in Pediatric Patients", J. Neurosurg. Pediatrics 7, 2011, pp. 516-521.

Ross et al., "A Simple Stereotactic Retractor for the use with the Leskell Stereotactic System", Neurosurgery, 1993, 32 (3), pp. 475-476, discussion p. 476.

Rymarczuk et al., "Use of Minimally Invasive Retractor System for Retrieval of Intracranial Fragments in Wartime Trauma", World Neurosurgery, 2015, pp. 1-26.

Scholz et al., "Development of an Endoscopic Navigation System Based on Digital Image Processing", Computer Aided Surgery, 1998, 3(3), pp. 134-143. (Abstract only).

Scholz et al., "Virtual Image Navigation: A New Method to Control Intraoperative Bleeding in Neuroendoscopic Surgery", Neurosurg. Focus, 2000, 8(6), pp. 1-8.

Shoakazemi et al., "A 3D Endoscopic Transtubular Transcallosal Approach to the Third Ventrile", J. Neurosurg., 2015, pp. 1-10.

Shults et al., Neuro-opthalmic Complications of Intracranial Catheters, Neurosurgery, vol. 33, No. 1, Jul. 1993, pp. 135-138.

Slavin, K. "Testimonials", no date, but admitted as prior art between Jun. 17, 2005 and Mar. 27, 2012, 4 pages.

Spetzger et al., "Navigational Microneurosurgery: Experience with EasyGuide Neuro", Medicamundi, 1997, 41(1), pp. 28-35.

Tao et al., "Microsurgical Resection for Lateral Ventricular Meningiomas with Neuronavigation and Tubular Retractor System", Chin. J. Neurosurgery, vol. 31, No. 4, 2015, pp. 332-336. (Abstract only).

"UPMC: Minimally Invasive Brain Surgery, Legacy of Innovations, Breakthroughs in Minimally Invasive Brain Surgery at UPMC", http://www.brainsurgery.upmc.com/meet-the-surgcons/legacy-of-innovations.aspx, 2014, 1 page.

Vycor Medical, "Vycor ViewSite TC: Endoscopic Intraparenchimal Brain Tumor Resection with Image Guidance," 2 pages, no date but admitted as prior art between Jun. 17, 2005 and Mar. 27, 2012, 2 pages.

Wang et al., "Endoscopic Hematoma Evacuation in Patients with Spontaneous Supratentorial Intracerebral Hemorrhage", Journal of the Chinese Medical Association, 78, 2015, pp. 101-107.

Zhong et al., "Brain Retraction Injury", Neurological Research, Dec. 2003, vol. 25, pp. 831-838.

Non Final Office Action for U.S. Appl. No. 15/372,890, dated Oct. 1, 2018, 31 pages.

International Search Report for App. No. PCT/US2023/026683, dated Dec. 14, 2023.

Non Final Office Action for U.S. Appl. No. 17/479,325, mailed Aug. 29, 2023, 16 pages.

Japanese Office Action in corresponding JP Application No. 2024-576609 (8 pages), mailed Jan. 6, 2026.

European Search Report in corresponding EP application 23836014 (8 pages), mailed May 22, 2026.

* cited by examiner

Fig. 6A
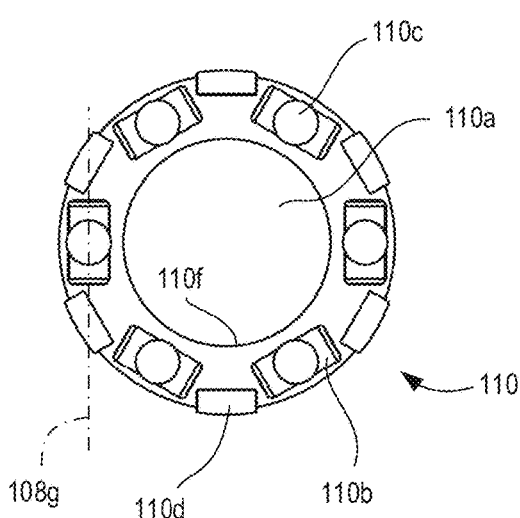
Fig. 6B
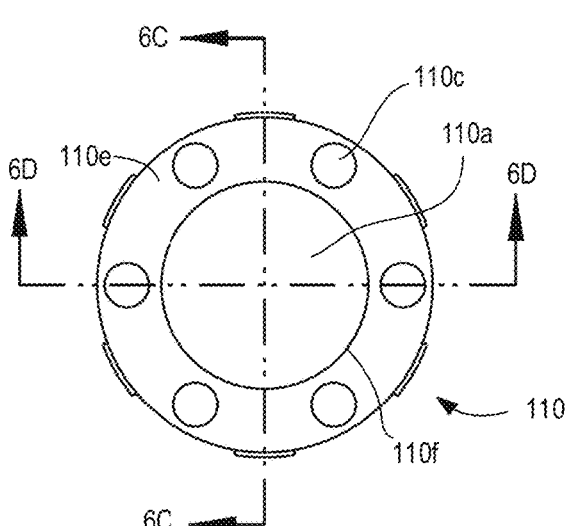
Fig. 6C
Fig. 6D

Fig. 7A
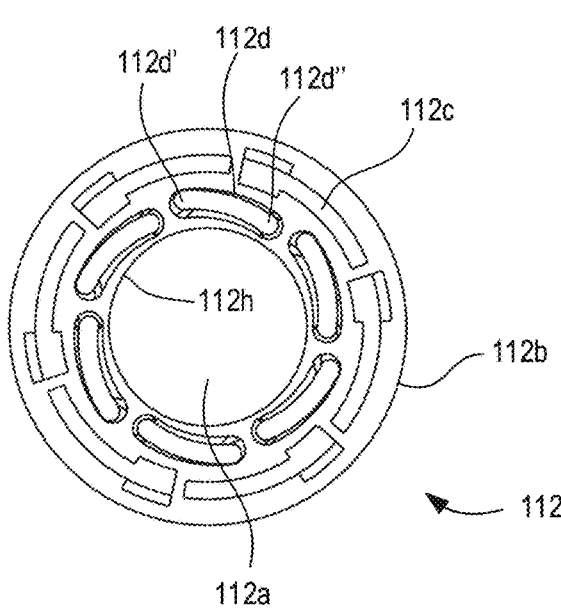
Fig. 7B
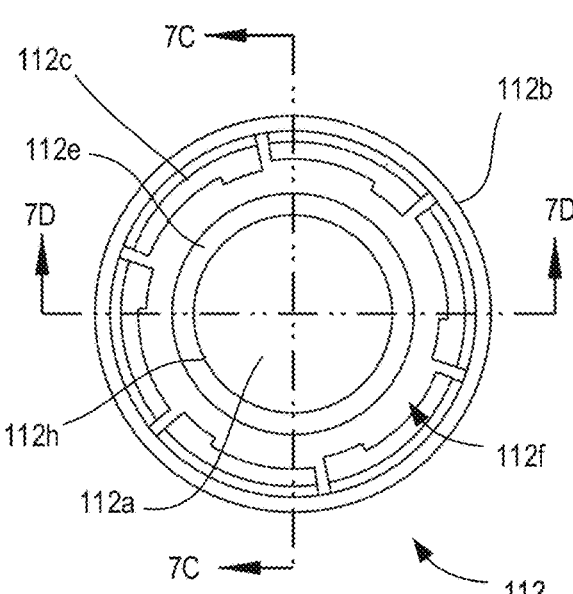
Fig. 7C
Fig. 7D

Fig. 10A
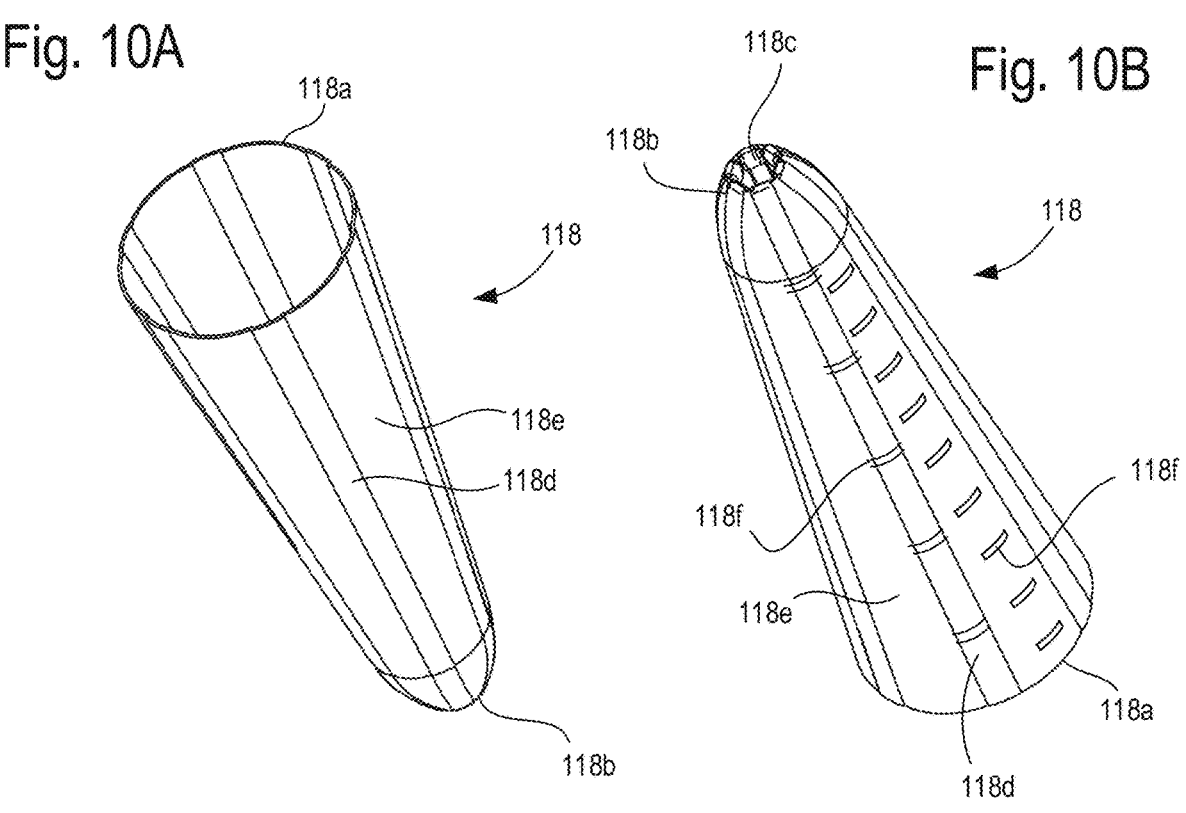
Fig. 10B
Fig. 10C
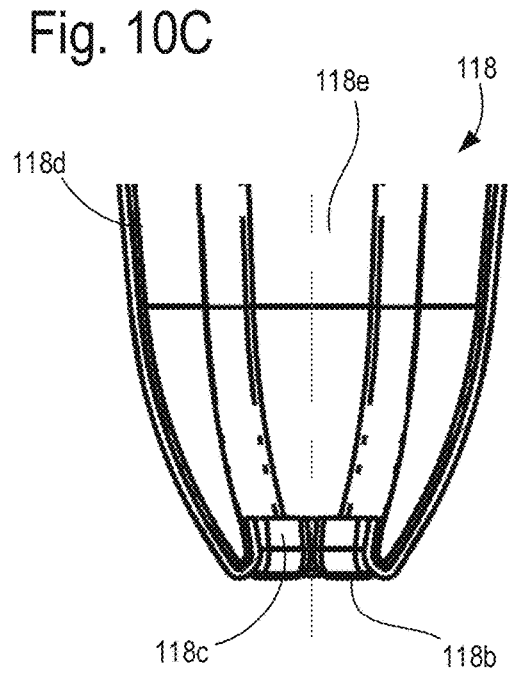
Fig. 10D
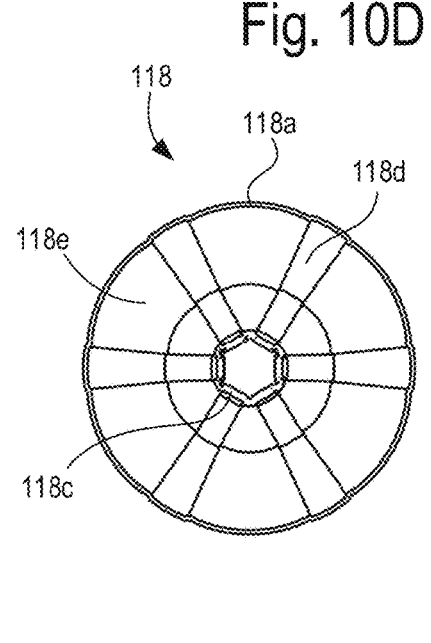

Fig. 11A
Fig. 11B
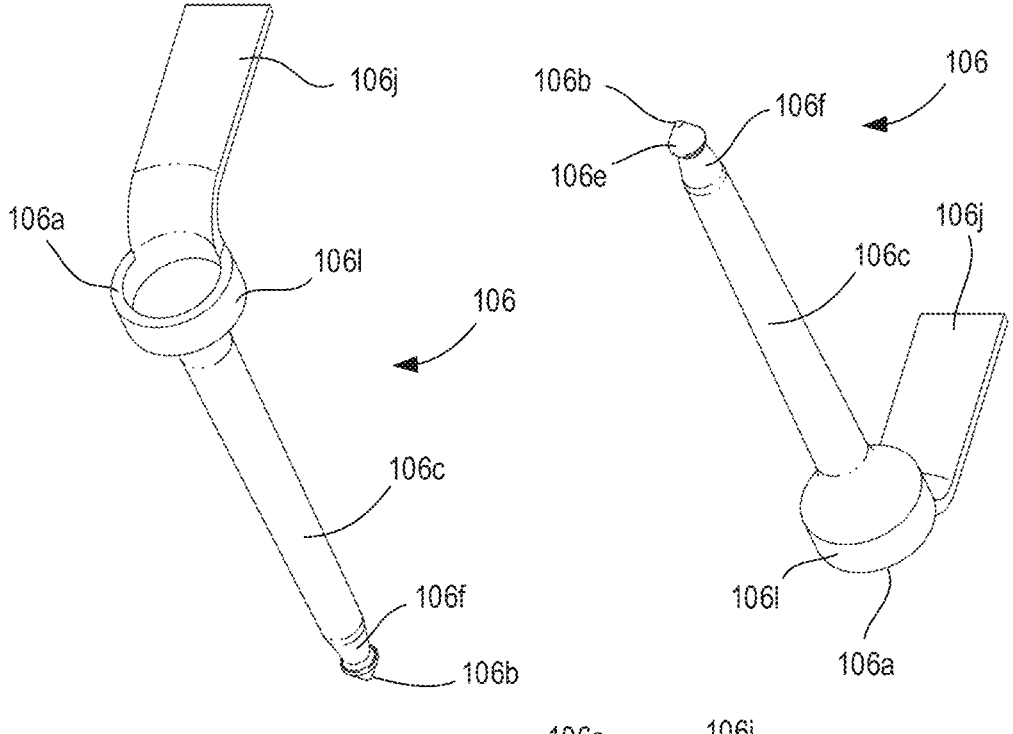
Fig. 11C
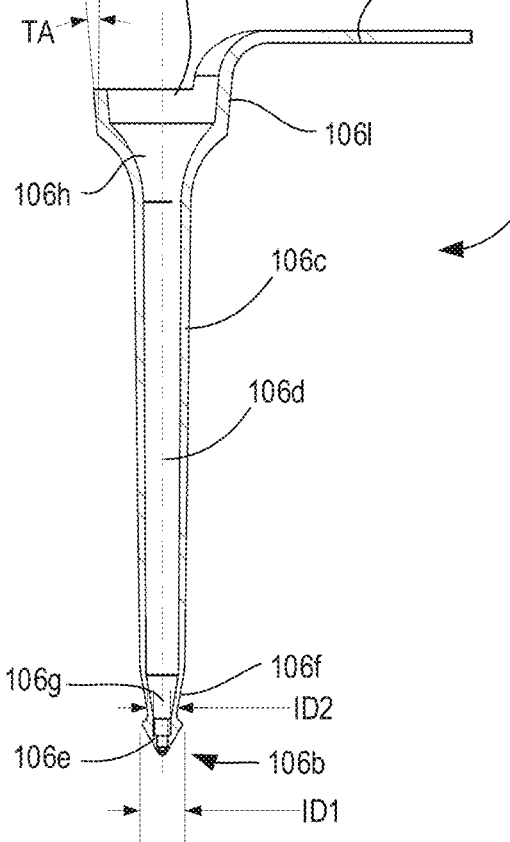

Fig. 24A
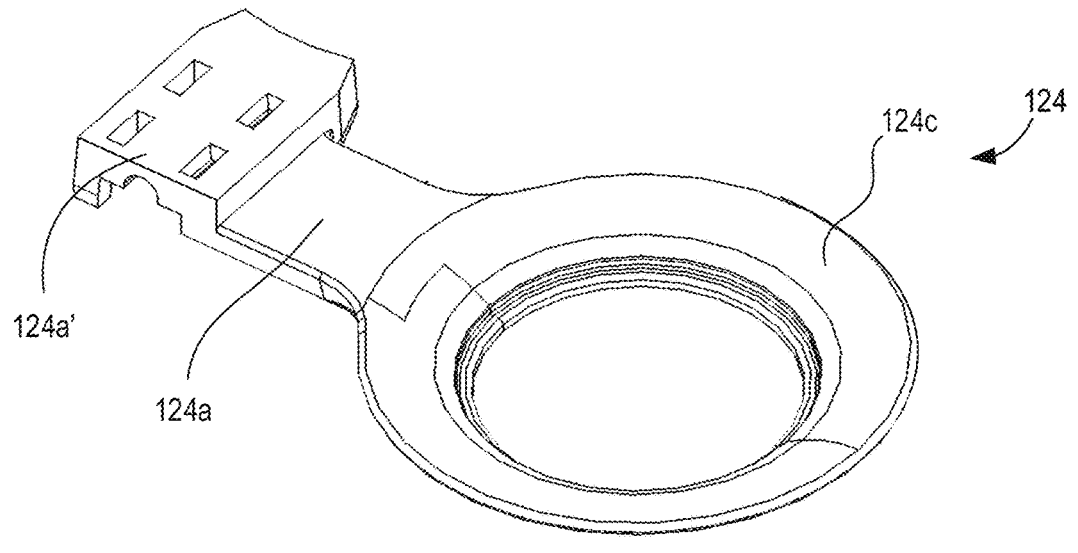
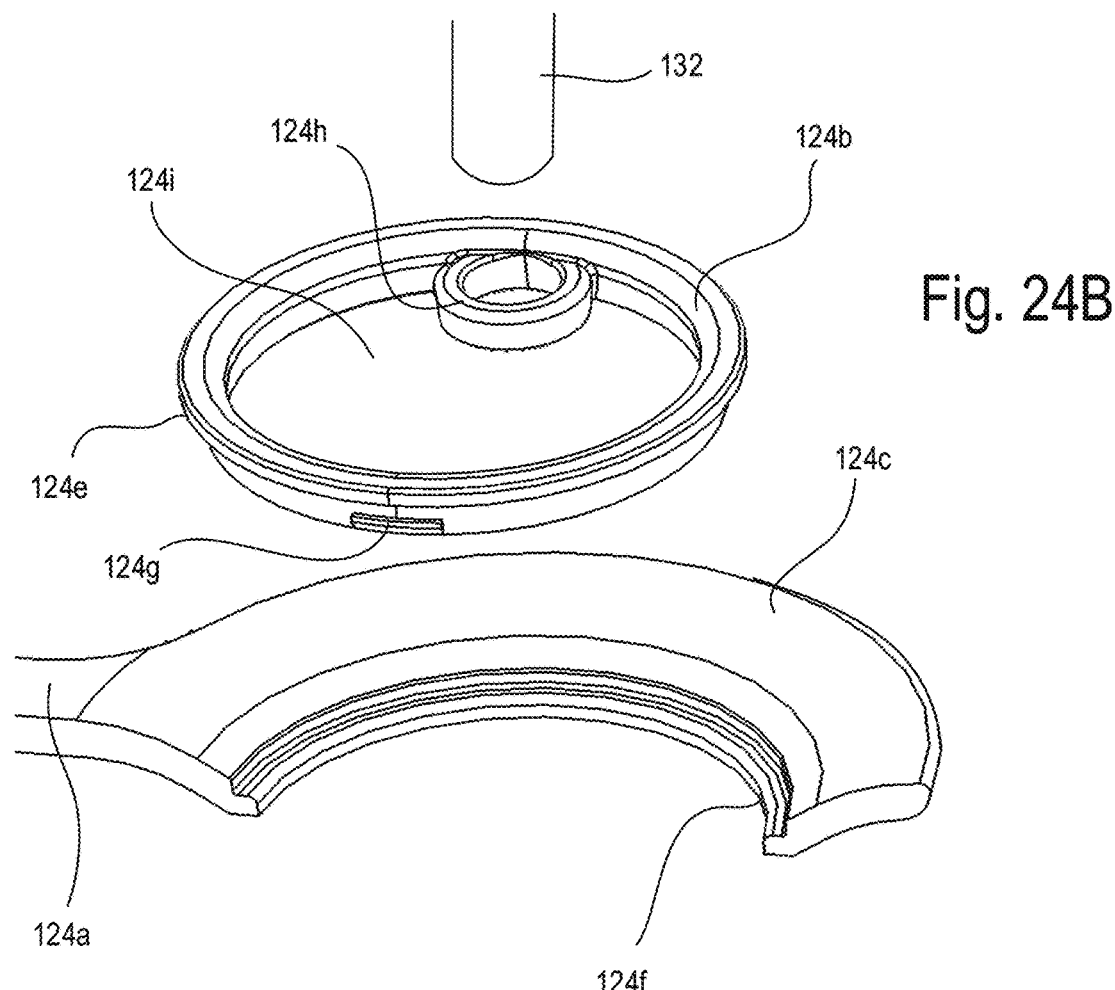
Fig. 24B

EXPANDABLE SURGICAL ACCESS PORT

This application claims priority to U.S. Provisional Application Ser. No. 63/358,651, filed Jul. 6, 2022, which is incorporated herein by reference.

BACKGROUND

A variety of access ports have been proposed and used for accessing the delicate tissue of the brain. Accessing brain tissue, especially interior brain tissue that is not accessible at the surface, poses a variety of challenges. For example, it is desirable to minimize damage to the brain tissue by atraumatically forming a pathway for access. To this end, surgical access ports typically have a tapered distal end to gently spread the tissue as the access port is moved into position at the surgery site. Upon reaching the surgery site, the central portion of the access port is removed or the access port is expanded to form a pathway for surgical instruments.

Another challenge with brain access ports is that the brain tissue can be damaged simply by contact with the wall of the access port. Intracranial pressure causes the brain tissue local to the access port to compress, potentially leading to brain ischemia—i.e., a reduction in blood flow and oxygen that can potentially lead to death of the local brain tissue. Such damage was particularly likely in the past, when flat blade or spoon retractors were used to create a surgical access pathway. The change to access ports having a full circular or oval shape has helped reduce the likelihood of ischemia, but this risk still remains under any circumstance in which the brain tissue is compressed.

While various brain access ports are known, there is an ongoing need to improve the art of surgical access ports.

SUMMARY

In one aspect, there is provided an expandable surgical access port comprising: an activation assembly defining an activation assembly opening surrounding a longitudinal axis, the activation assembly comprising: an activation arm mounting body defining an activation arm mounting body opening surrounding at least a portion of the activation assembly opening, the activation arm mounting body comprising a plurality of pivot locations surrounding the longitudinal axis, each pivot location defining a respective pivot axis extending in a plane perpendicular to the longitudinal axis and not intersecting the longitudinal axis, and an activation ring mounted to the activation arm mounting body and defining an activation ring opening surrounding at least a portion of the activation assembly opening, wherein the activation ring is rotatable about the longitudinal axis relative to the activation arm mounting body, to rotate between a first activation ring position and a second activation ring position, wherein the activation ring remains at a fixed location along the longitudinal axis throughout a full range of movement between the first activation ring position and the second activation ring position; a plurality of activation arms arranged around the longitudinal axis, each activation arm extending in a distal direction from a respective proximal arm end to a respective distal arm end, with each respective proximal arm end being pivotally connected to the activation assembly at a respective one of the plurality of pivot locations, wherein each activation arm is pivotable about the respective pivot axis, upon movement of the activation ring from the first activation ring position to the second activation ring position, from a respective first arm position in which each respective distal arm end is spaced a respective first distance from the longitudinal axis, and a respective second arm position in which each respective distal arm end is spaced a respective second distance from the longitudinal axis, wherein each respective second distance is greater in magnitude than each respective first distance; a membrane surrounding the plurality of activation arms and extending from a proximal membrane end adjacent the activation assembly to a distal membrane end, wherein the membrane comprises a flexible material that is expandable to permit the plurality of activation arms to move from the respective first positions to the respective second positions.

In some aspects, the activation arm mounting body comprises: a port housing defining a port housing opening surrounding at least a portion of the activation assembly opening and comprising a plurality of first pivot recesses; and a lock ring defining a lock ring opening surrounding at least a portion of the activation assembly opening and comprising a plurality of second pivot recesses; wherein the lock ring is secured to the port housing with each of the first pivot recesses adjacent to a respective one of the second pivot recesses to define a respective one of the pivot locations.

In some aspects, the lock ring is secured to the port housing by a plurality of locking tabs and corresponding locking tab receivers.

In some aspects, the activation ring is attached to the port housing by a rotatable connection.

In some aspects, the rotatable connection comprises a plurality of sliding tabs and corresponding sliding tab receivers.

In some aspects, each pivot location comprises a respective activation arm port extending in the distal direction along the longitudinal axis from the respective pivot axis, and each activation arm is movable within at least a portion of each activation arm port.

In some aspects, the activation ring is rotatable in a first direction to drive the activation arms from their respective first arm positions to their respective second arm positions, and rotatable in a second direction to drive the activation arms from their respective second arm positions to their respective first arm positions.

In some aspects, the activation ring comprises a plurality of cam slots, each cam slot extending about a portion of the activation ring opening from a respective first cam slot end to a respective second cam slot end, wherein each respective second cam slot end is closer to the longitudinal axis than each respective first cam slot end.

In some aspects, each activation arm comprises a respective pivot, and a respective cam follower extending in the proximal direction from the respective pivot and into a respective one of the cam slots; and wherein rotation of the activation ring from the first activation ring position to the second activation ring position causes each respective cam follower to move from the respective first cam slot end to the respective second cam slot end to thereby move the respective activation arm from the respective first arm position to the respective second arm position.

In some aspects, each pivot location comprises a respective cam follower port extending in a proximal direction, opposite the distal direction, along the longitudinal axis from the respective pivot axis, and each cam follower extends through a respective one of the cam follower ports.

In some aspects, the activation ring comprises a tapered inlet surface reducing in diameter in the distal direction.

In some aspects, each activation arm comprises: a respective pivot located at the respective proximal arm end and rotationally secured a respective one of the pivot locations; and a respective straight elongated body extending from the respective pivot to the respective distal arm end; wherein the respective distal arm end of each activation arm comprises an inward bend towards the longitudinal axis.

In some aspects, at least one of the activation arms comprises a respective light located at the respective distal arm end.

In some aspects, the at least one activation arm comprises a respective slot extending at least partially between the respective proximal arm end and the respective distal arm end from a proximal slot end to a distal slot end, and wherein the respective light is located at the respective distal slot end.

In some aspects, the at least one activation arm comprises one of a light guide and an electrical wire extending along the slot from the proximal slot end to the light.

In some aspects, the proximal slot end is at the respective pivot of the respective activation arm.

In some aspects, the respective slot is located in a respective outer radial surface of the respective activation arm.

In some aspects, each pivot axis is tangential to the longitudinal axis.

In some aspects, the activation ring is positioned on a proximal side of the activation arm mounting body.

In some aspects, the activation ring comprises an outer surface defining a grip, wherein the grip is larger in a respective diameter than a respective diameter of an adjacent portion of the activation arm mounting body.

In some aspects, the activation ring is positioned on a proximal side of the activation arm mounting body.

In some aspects, the activation ring comprises an outer surface comprising knurling.

In some aspects, the activation ring mounting body further comprises one or more extensions located at or proximally from a proximal side of the activation ring.

In some aspects, the activation ring mounting body further comprises one or more extensions configured to connect to one or more of: a clamp, a navigation device, and a surgical tool mount.

In some aspects, there further is a position indicator configured to identify a position of the activation ring relative to the activation arm mounting body.

In some aspects, the activation arm mounting body comprises one or more body position indicators; and the activation ring comprises one or more ring position indicators; wherein the one or more body position indicators and the one or more ring position indicators are aligned when the activation ring is at one or more predetermined positions relative to the activation arm mounting body.

In some aspects, the activation ring comprises an outer surface defining a grip, wherein the grip is larger in a respective diameter than a respective diameter of an adjacent portion of the activation arm mounting body.

In some aspects, depth markers are spaced along the longitudinal axis and visible on or through the membrane.

In some aspects, the expandable surgical access port further comprises a surgical tool mount configured to secure to the activation arm mounting body, the surgical tool mount comprising: a ring-shaped mount body defining a circular opening; and a ring-shaped connector mounted in the opening and configured to rotate about a central axis of the circular opening, the ring-shaped connector having a tool lock radially offset from the central axis of the circular opening.

In some aspects, the ring-shaped connector is freely rotatable about at least a portion of the central axis of the circular opening and does not comprise a rotation lock.

In another exemplary aspect, there is provided an expandable surgical access port comprising: an activation assembly defining an activation assembly opening surrounding a longitudinal axis; a plurality of activation arms arranged around the longitudinal axis and movably attached to the activation assembly, each activation arm comprising an elongated body extending in a distal direction from the activation assembly to a respective distal arm end; and a flexible membrane surrounding the plurality of activation arms and extending from a proximal membrane end adjacent the activation assembly to a distal membrane end adjacent the respective distal arm ends; wherein at least one activation arm comprises: a respective slot extending between the activation assembly and the respective distal arm end from a proximal slot end to a distal slot end, and a respective light located at the respective distal slot end.

In some aspects, there further is a light connector extending along the slot from the proximal slot end to the light.

In some aspects, the light connector comprises at least one of a light guide and an electrical wire.

In some aspects, the proximal slot end is at a respective pivot joining the respective activation arm to the activation assembly.

In some aspects, the activation assembly comprises a housing interior space configured to receive a portion of the light connector, and the proximal slot end is open to the housing interior space.

In some aspects, the activation assembly comprises: an activation arm mounting body defining an activation arm mounting body opening surrounding at least a portion of the activation assembly opening, the activation arm mounting body comprising a plurality of pivot locations surrounding the longitudinal axis, each pivot location defining a respective pivot axis extending in a plane perpendicular to the longitudinal axis and not intersecting the longitudinal axis; and an activation ring mounted to the activation arm mounting body and defining an activation ring opening surrounding at least a portion of the activation assembly opening, wherein the activation ring is rotatable about the longitudinal axis relative to the activation arm mounting body, to rotate between a first activation ring position and a second activation ring position; wherein each of the plurality of activation arms is pivotally connected to the activation assembly at a respective one of the plurality of pivot locations, and each activation arm is pivotable about the respective pivot axis, upon movement of the activation ring from the first activation ring position to the second activation ring position, from a respective first arm position in which each respective distal arm end is spaced a respective first distance from the longitudinal axis, and a respective second arm position in which each respective distal arm end is spaced a respective second distance from the longitudinal axis, wherein each respective second distance is greater in magnitude than each respective first distance.

In some aspects, the proximal slot end is at a respective pivot joining the respective activation arm to the respective pivot location.

In some aspects, the activation ring remains at a fixed location along the longitudinal axis throughout a full range of movement between the first activation ring position and the second activation ring position.

In some aspects, the activation arm mounting body comprises: a port housing defining a port housing opening surrounding at least a portion of the activation assembly opening; a connector housing defining a connector housing opening surrounding at least a portion of the activation assembly opening, the connector housing being adjacent to the port housing and defining the housing interior space between the connector housing and the port housing; and a lock ring defining a lock ring opening surrounding at least a portion of the activation assembly opening.

In some aspects, the lock ring is secured to the connector housing with at least a portion of the port housing captured between the lock ring and the connector housing.

In some aspects, there also is provided a plurality of locking tabs extending into the portion of the port housing captured between the lock ring and the connector housing and a plurality of locking tab receivers configured to connect to the plurality of locking tabs.

In some aspects, the plurality of pivot locations are defined between the lock ring and the port housing.

In some aspects, the activation assembly housing interior space comprises a portion extending radially from the longitudinal axis and open in a proximal direction opposite the distal direction.

In some aspects, the respective slot is located in a respective outer radial surface of the respective activation arm.

In some aspects, the flexible membrane surrounds the respective outer radial surface and the respective slot.

In some aspects, the flexible membrane is molded in place.

In another exemplary aspect, there is provided an expandable surgical access port comprising: an activation assembly defining an activation assembly opening surrounding a longitudinal axis; a plurality of activation arms arranged around the longitudinal axis, each activation arm extending in a distal direction from a respective proximal arm end to a respective distal arm end, with each respective proximal arm end being movably connected to the activation assembly and movable, upon operation of the activation assembly, between a respective first position in which each respective distal arm end is spaced a respective first distance from the longitudinal axis, and a respective second position in which each respective distal arm end is spaced a respective second distance from the longitudinal axis, wherein each respective second distance is greater in magnitude than each respective first distance; and a membrane surrounding the plurality of activation arms and extending in the distal direction from a proximal membrane end adjacent the activation assembly to a distal membrane end adjacent the respective distal arm ends, wherein the membrane comprises a flexible material that is overmolded onto the plurality of activation arms and expandable to permit the plurality of activation arms to move from the respective first positions to the respective second positions.

In some aspects, the membrane comprises a thermoplastic elastomer.

In some aspects, the membrane comprises an elastomer based on styrenic olefinic rubber and hydrogenated isoprene, containing polypropylene as a reinforcing agent and mineral oil as a plasticizer and processing aid.

In some aspects, the membrane has a wall thickness of 0.024 inches to 0.008 inches.

In some aspects, the membrane has a wall thickness of 0.020 inches to 0.012 inches.

In some aspects, the membrane has a wall thickness of 0.015 inches to 0.017 inches.

In some aspects, the membrane is expandable by at least 250% at the distal membrane end.

In some aspects, the membrane is expandable by at least 300% at the distal membrane end.

In some aspects, the membrane is expandable by at least 350% at the distal membrane end.

In some aspects, the membrane is expandable at the distal membrane end from a diameter of 0.40 inches or less to a diameter of 0.80 inches or more.

In some aspects, the membrane is expandable at the distal membrane end from a diameter of 0.30 inches or less to a diameter of 0.90 inches or more.

In some aspects, the membrane is expandable at the distal membrane end from a diameter of 0.25 inches or less to a diameter of 1.00 inches or more.

In some aspects, the membrane comprises a respective rib located on an outer radial surface of each activation arm, and a respective wall extending between each adjacent pair of ribs.

In some aspects, the membrane comprises a lip that wraps around the respective distal arm ends.

In some aspects, each activation arm comprises a respective outer radial surface, and each outer radial surface comprises a respective slot extending at least partially between the respective proximal arm end and the respective distal arm end, and respective portions of the overmolded flexible membrane material extend into each slot.

In some aspects, at least one of the respective slots comprises a light encased between the respective slot and the respective portion of the overmolded flexible membrane.

In another exemplary aspect, there is provided a method for manufacturing an expandable surgical access port, the method comprising: providing an activation assembly defining an activation assembly opening surrounding a longitudinal axis; providing a plurality of activation arms arranged around the longitudinal axis, each activation arm extending in a distal direction from a respective proximal arm end to a respective distal arm end, with each respective proximal arm end being movably connected to the activation assembly and movable, upon operation of the activation assembly, between a respective first position in which each respective distal arm end is spaced a respective first distance from the longitudinal axis, and a respective second position in which each respective distal arm end is spaced a respective second distance from the longitudinal axis, wherein each respective second distance is greater in magnitude than each respective first distance; and overmolding a membrane onto the plurality of activation arms, the membrane extending in the distal direction from a proximal membrane end adjacent the activation assembly to a distal membrane end adjacent the respective distal arm ends, wherein the membrane comprises a flexible material that is expandable to permit the plurality of activation arms to move from the respective first positions to the respective second positions.

In some aspects, the membrane comprises a thermoplastic elastomer.

In some aspects, the membrane comprises an elastomer based on styrenic olefinic rubber and hydrogenated isoprene, containing polypropylene as a reinforcing agent and mineral oil as a plasticizer and processing aid.

In some aspects, the membrane has a wall thickness of 0.024 inches to 0.008 inches.

In some aspects, the membrane has a wall thickness of 0.020 inches to 0.012 inches.

In some aspects, the membrane has a wall thickness of 0.015 inches to 0.017 inches.

In some aspects, the membrane is expandable by at least 250% at the distal membrane end.

In some aspects, the membrane is expandable by at least 300% at the distal membrane end.

In some aspects, the membrane is expandable by at least 350% at the distal membrane end.

In some aspects, the membrane is expandable at the distal membrane end from a diameter of 0.40 inches or less to a diameter of 0.80 inches or more.

In some aspects, the membrane is expandable at the distal membrane end from a diameter of 0.30 inches or less to a diameter of 0.90 inches or more.

In some aspects, the membrane is expandable at the distal membrane end from a diameter of 0.25 inches or less to a diameter of 1.00 inches or more.

In some aspects, each activation arm comprises a respective outer radial surface, and overmolding the membrane onto the plurality of activation arms comprises overmolding the membrane over the respective outer radial surface of each activation arm.

In some aspects, each activation arm comprises a respective slot extending at least partially along the respective outer radial surface, and overmolding the membrane comprises overmolding respective portions of the membrane material into each slot.

In some aspects, at least one respective slot comprises a light, and overmolding the membrane comprises encasing the light between the respective slot and the membrane.

In some aspects, overmolding the membrane comprises forming a respective rib located on an outer radial surface of each activation arm, and a respective wall extending between each adjacent pair of ribs.

In some aspects, overmolding the membrane comprises overmolding a lip that wraps around each respective distal arm end.

In another exemplary aspect, there is provided an expandable surgical access port assembly comprising: an activation assembly defining an activation assembly opening surrounding a longitudinal axis; a plurality of activation arms arranged around the longitudinal axis, each activation arm extending in a distal direction from a respective proximal arm end at the activation assembly to a respective distal arm end, wherein each respective proximal arm end is movable, upon operation of the activation assembly, between a respective first position in which each respective distal arm end is spaced a respective minimum distance from the longitudinal axis, and a respective second position in which each respective distal arm end is spaced a respective maximum distance from the longitudinal axis, wherein each respective maximum distance is greater in magnitude than each respective minimum distance; a membrane surrounding the plurality of activation arms and extending in the distal direction from a proximal membrane end adjacent the activation assembly to a distal membrane end, wherein the membrane is expandable to permit the plurality of activation arms to move from the respective first positions to the respective second positions; and an introducer extending from a proximal introducer end to a distal introducer end, the introducer comprising: a tubular wall defining a cannula extending within the introducer from the proximal introducer end to a point adjacent to the distal introducer end, an introducer tip located at the distal introducer end, the introducer tip being tapered to increase in size in the proximal direction to a first introducer diameter, an outer annular recess comprising a region located proximally to the introducer tip and having a second introducer diameter, the second introducer diameter being less than the first introducer diameter; wherein: the introducer is selectively insertable through the activation assembly opening and connected to the activation assembly at an operative position, with the cannula located along the longitudinal axis and the introducer tip extending in the distal direction beyond the respective distal arm ends; and with the introducer at the operative position and the plurality of activation arms in the respective first positions, at least a portion of each distal arm end is positioned within the outer annular recess.

In some aspects, each activation arm comprises a respective pivot located at the respective proximal arm end and rotationally secured at a respective pivot location to the activation ring assembly.

In some aspects, each activation arm is configured to pivot about a respective pivot axis, and each respective pivot axis is tangential to the longitudinal axis.

In some aspects, each activation arm comprises a respective straight elongated body extending from the respective pivot to the respective distal arm end.

In some aspects, each respective distal arm end of each activation arm comprises an inward bend towards the longitudinal axis, and each respective inward bend is positioned within the annular recess when the plurality of activation arms or in the respective first positions.

In some aspects, with the introducer at the operative position and the plurality of activation arms in the respective first positions, the introducer tip and the plurality of activation arms or the membrane form a continuous tapered outer wall.

In some aspects, the introducer cannula terminates at the distal introducer end at a probe tip receiver configured to retain one or more different navigation probe tips.

In some aspects, the activation assembly comprises an inner face surrounding the activation assembly opening; and the introducer comprises an outer face; wherein, with the introducer at the operative position, the outer face is in contact with the inner face to prevent movement of the outer face in a perpendicular direction relative to the longitudinal axis.

In some aspects, at least one of the inner face and the outer face is tapered to decrease in diameter in the distal direction.

In some aspects, the inner face and the outer face are tapered to decrease in diameter in the distal direction.

In some aspects, the inner face and the outer face each comprises a respective conical surface.

In some aspects, the respective conical surfaces of the inner face and the outer face have matching respective taper angles.

In some aspects, the activation assembly comprises a plurality of position indicators configured to indicate when the plurality of activation arms are in at least one of the respective first positions and the respective second positions.

In some aspects, the activation assembly comprises a plurality of position indicators configured to indicate when the plurality of activation arms are in respective intermediate positions between the respective first positions and the respective second position.

In some aspects, the respective intermediate positions comprise respective positions in which the distal arm ends are spaced apart at the first introducer diameter.

BRIEF DESCRIPTION OF THE DRAWINGS

FIGS. 6A to 6D are bottom plan, top plan, side cross-section and front cross-section various views, respectively, of an exemplary lock ring.

FIGS. 7A to 7D are bottom plan, top plan, side cross-section and front cross-section various views, respectively, of an exemplary activation ring.

FIGS. 10A to 10D are top isometric, bottom isometric, detail side cross-section and top plan views, respectively, of an exemplary.

FIGS. 11A to 11C are top isometric, bottom isometric, and side cross-section views of an exemplary introducer.

FIGS. 19A to 19C are top plan, top isometric and bottom isometric views, respectively, of an exemplary surgical tool mount.

FIGS. 24A and 24B illustrate another example of a surgical tool mount.

In the drawings, features that are repeated in substantially identical form are in many cases designated at a single location to preserve the clarity of the drawings. Like features are designated in different embodiments with like reference numbers.

DESCRIPTION OF EXEMPLARY EMBODIMENTS

The present disclosure provides non-limiting examples of embodiments of expandable brain access ports. Specific details of these embodiments are provided to aid in understanding, but such details are not intended to limit the scope of any of the appended claims, except as specifically recited in the claims. It will also be understood that certain details not currently recited in the claims may be added to the claims in the future, particularly as it becomes apparent through consideration of prior art and other factors that these details provide a benefit over the known art.

Figure 1:
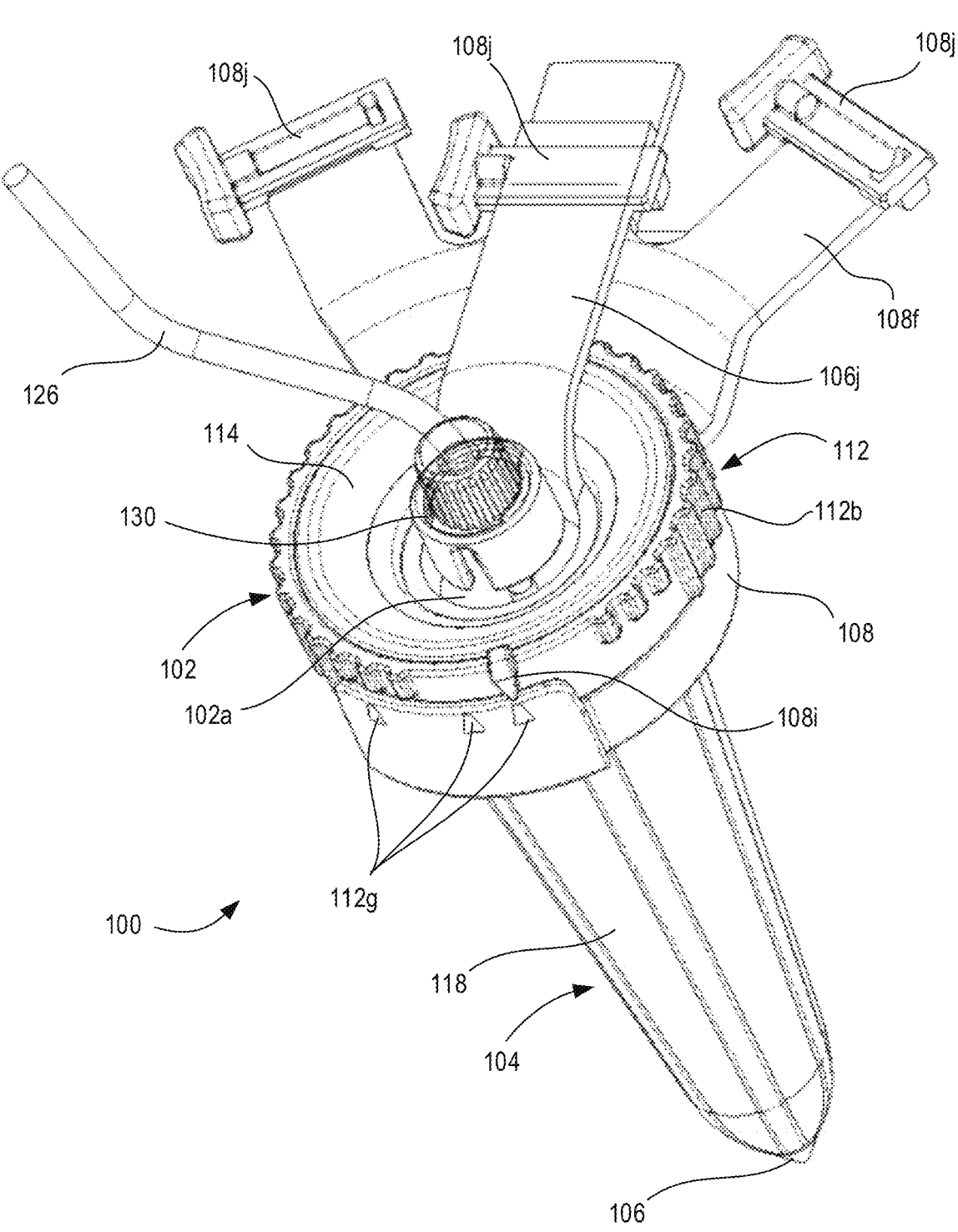
FIG. 1 is an isometric view of an exemplary embodiment of an expandable access port shown assembled with a navigation probe.

A first example of an expandable access port 100 is shown in FIG. 1. The expandable access port 100 generally includes an activation assembly 102, and expandable port 104, and an introducer 106. Details of these features are discussed below. The expandable access port 100 is configured to hold or provide access for one or more surgical instruments, such as endoscopes, resection tools, suction hoses, lights, and navigation devices. To this end, the activation assembly 102 defines an activation assembly opening 102a that surrounds a longitudinal axis 100a of the expandable access port 100.

In the case of FIG. 1, the expandable access port 100 is set up in a configuration to hold a navigation probe 126 located internal to the expandable access port 100. The navigation probe 126 is connected to a tracking system that monitors the position of the navigation probe 126. A typical navigation probe 126 and tracking system are registered to track the position of the probe's tip 126b and the trajectory of the probe shaft 126a. When integrated into the expandable access port 100, the probe tip 126b may be located at the distal tip of the introducer 106 to simply use the pre-set registration of the navigation probe 126 to track the introducer tip, and thus assume or extrapolate the position of the remainder of the expandable access port 100. It is also possible to register the navigation probe 126 to track the full shape and position of the expandable access port 100, regardless of the actual position of the probe tip 126b and probe shaft 126a. For example, if the probe tip 126b is seated a certain fixed distance from the distal end of the introducer 106, an offset can be programmed into the tracking system to account for this known offset. It is also possible to register the exact shape of the expandable access port 100 and/or the expandable port 104, to track the entire shape of device. Such navigation probes 126 and their tracking systems, including methods for setting an offset and determining the shape of the device, are known in the art, and need not be described in detail herein.

A probe lock 130 is provided to selectively hold the navigation probe 126 at a fixed location relative to the expandable access port 100. A non-limiting example of a suitable probe lock 130 may be found in U.S. application Ser. No. 17/473,282 (publication no. 2021/0401457), which is incorporated by reference herein. Other examples and details of probe locks 130 are provided below.

In use, the activation assembly 102 and expandable port 104 may be provided as an assembled structure that is not generally intended for disassembly (e.g., no reversible fasteners such as screws), but this is not strictly required. The introducer 106 can be secured to the activation assembly 102 and expandable port 104 to facilitate atraumatic insertion of the expandable access port 100 into the brain to the surgery site. The navigation probe 126 may be used to help direct the expandable access port 100 precisely to the surgery site. Upon insertion to the desired location, the introducer 106 is removed, and the activation assembly 102 is operated to expand the expandable port 104. At the conclusion of surgery, the expandable access port 100 is withdrawn from the brain. The expandable port 104 may or may not be retracted prior to withdrawing the expandable access port 100.

Figures 2A, 2B:
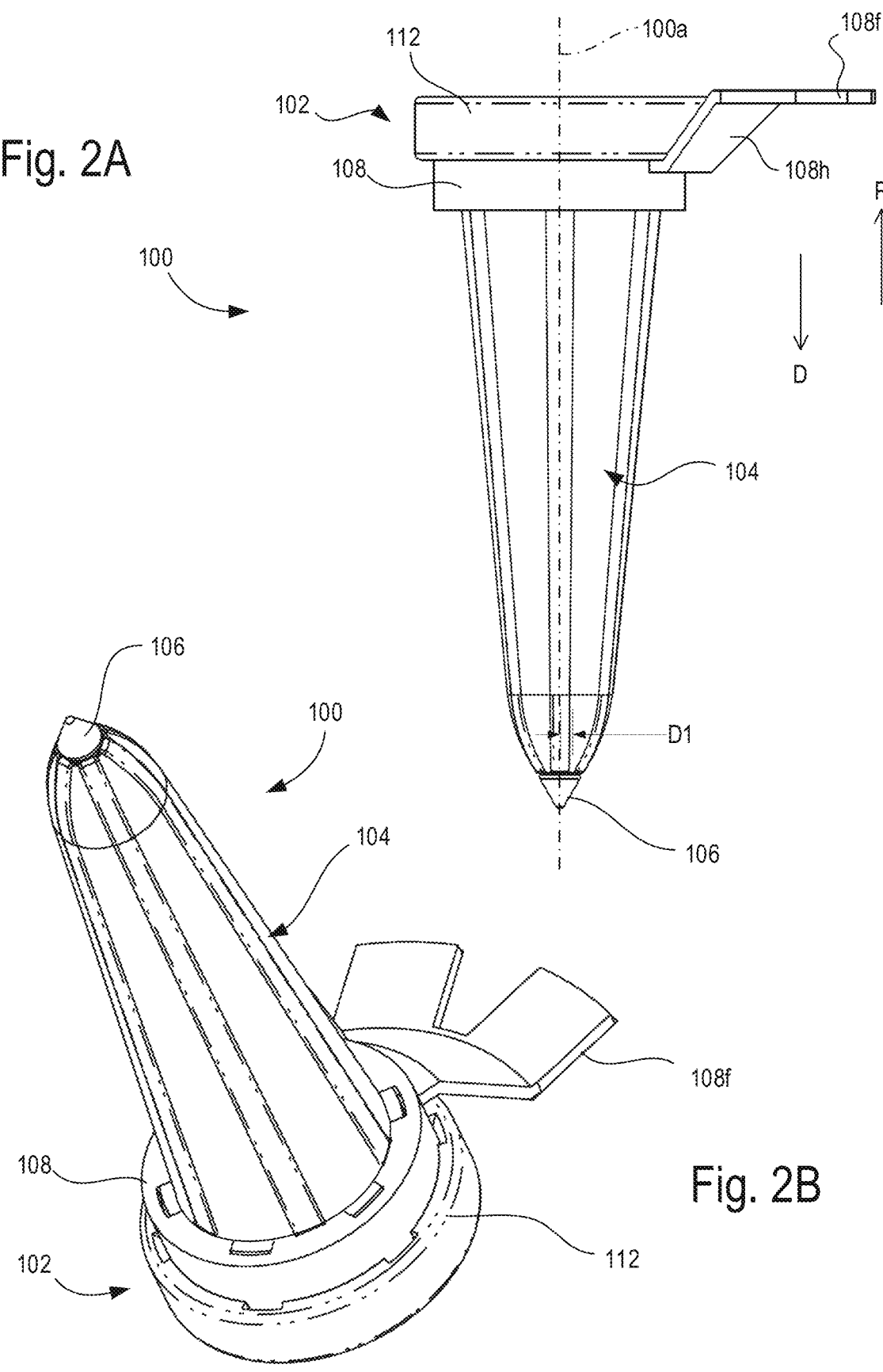
FIGS. 2A and 2B are side plan and isometric views of another exemplary embodiment of an expandable access port, shown with its expandable port in a contracted position.
Figures 3A, 3B:
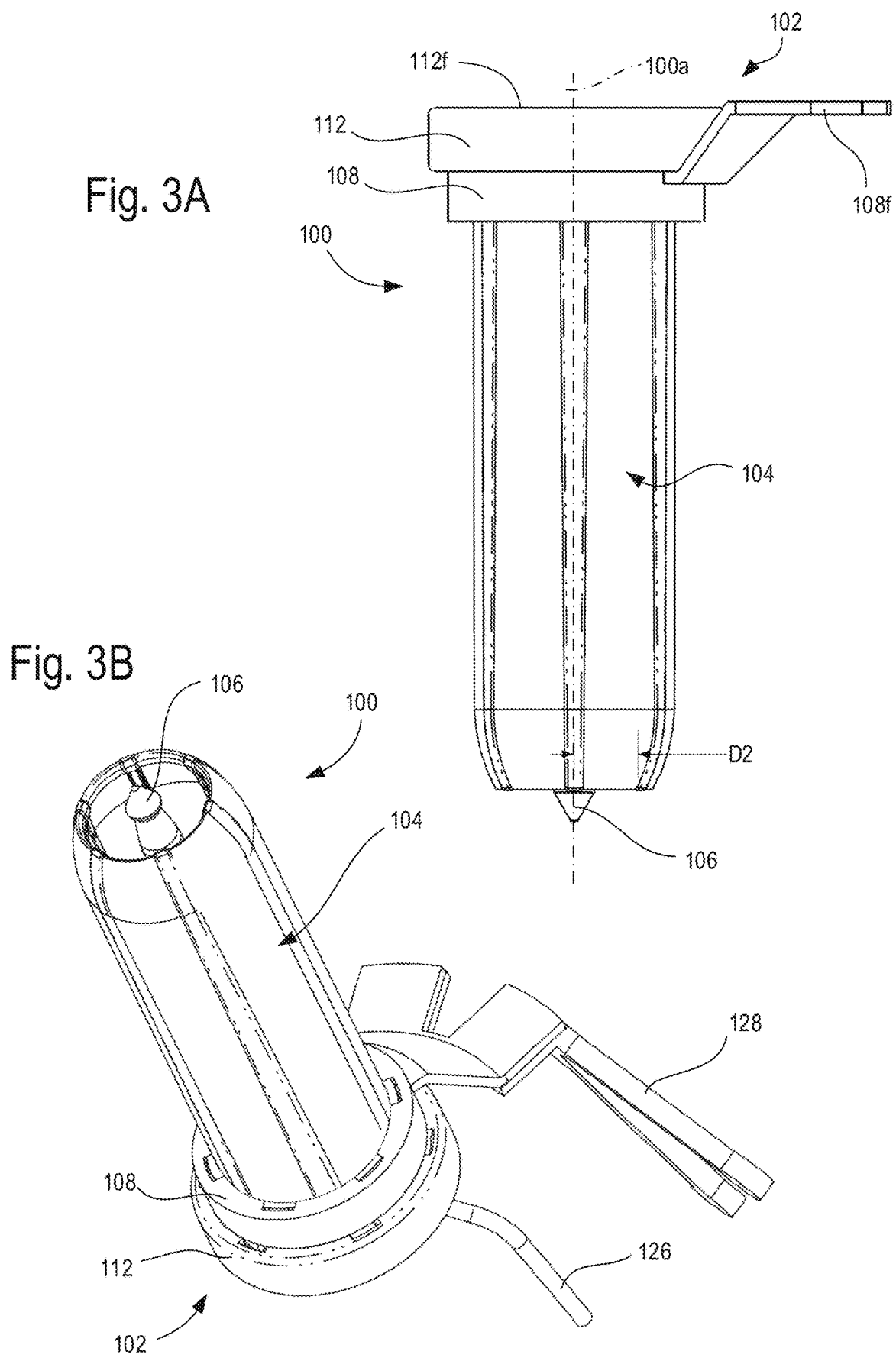
FIGS. 3A and 3B are side plan and isometric views of the expandable access port of FIGS. 2A and 2B, shown with its expandable port 104 in an expanded position.
Figures 4A, 4B:
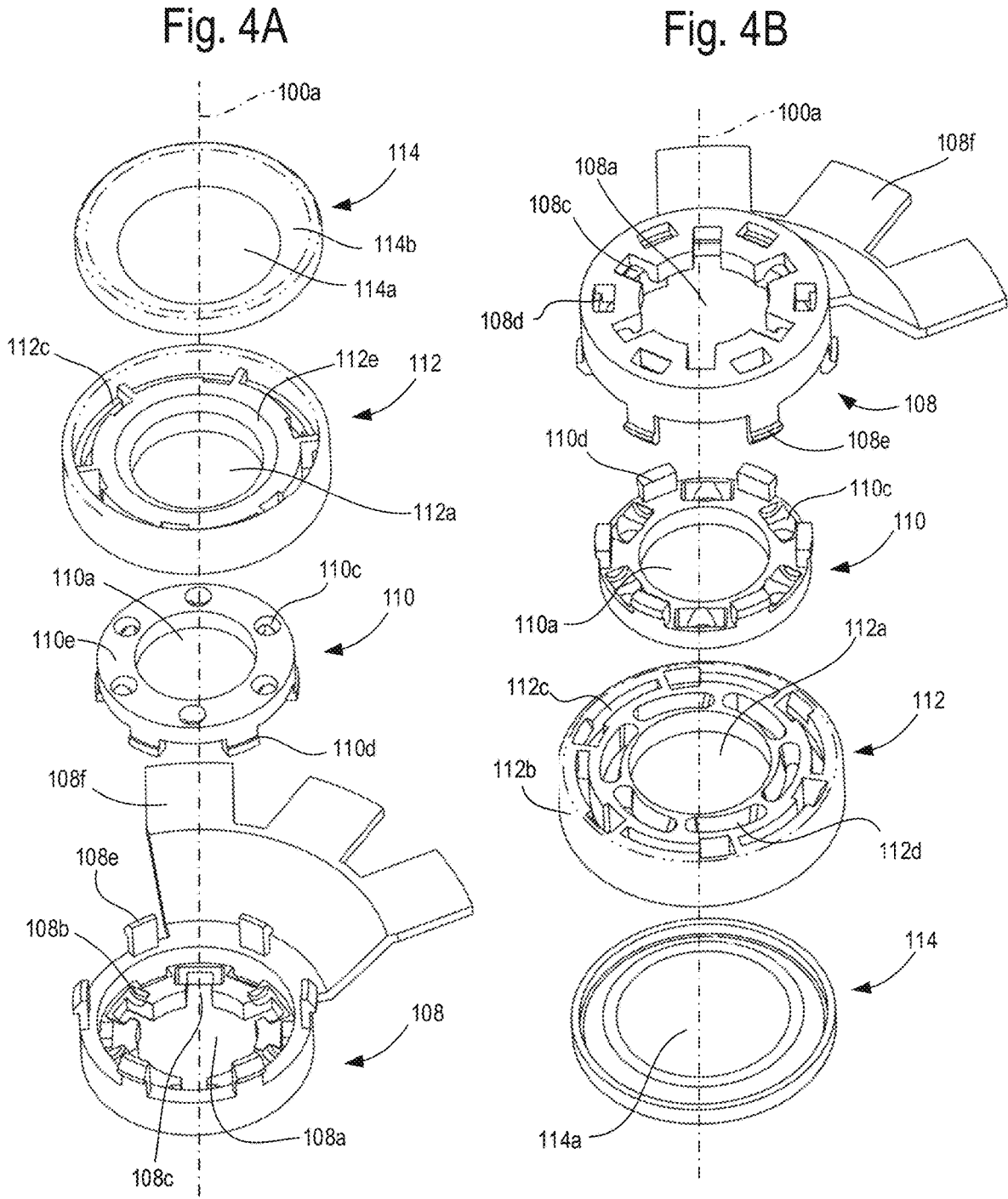
FIGS. 4A and 4B are top and bottom exploded isometric views of an activation assembly.
Figures 5A, 5B, 5C, 5D:
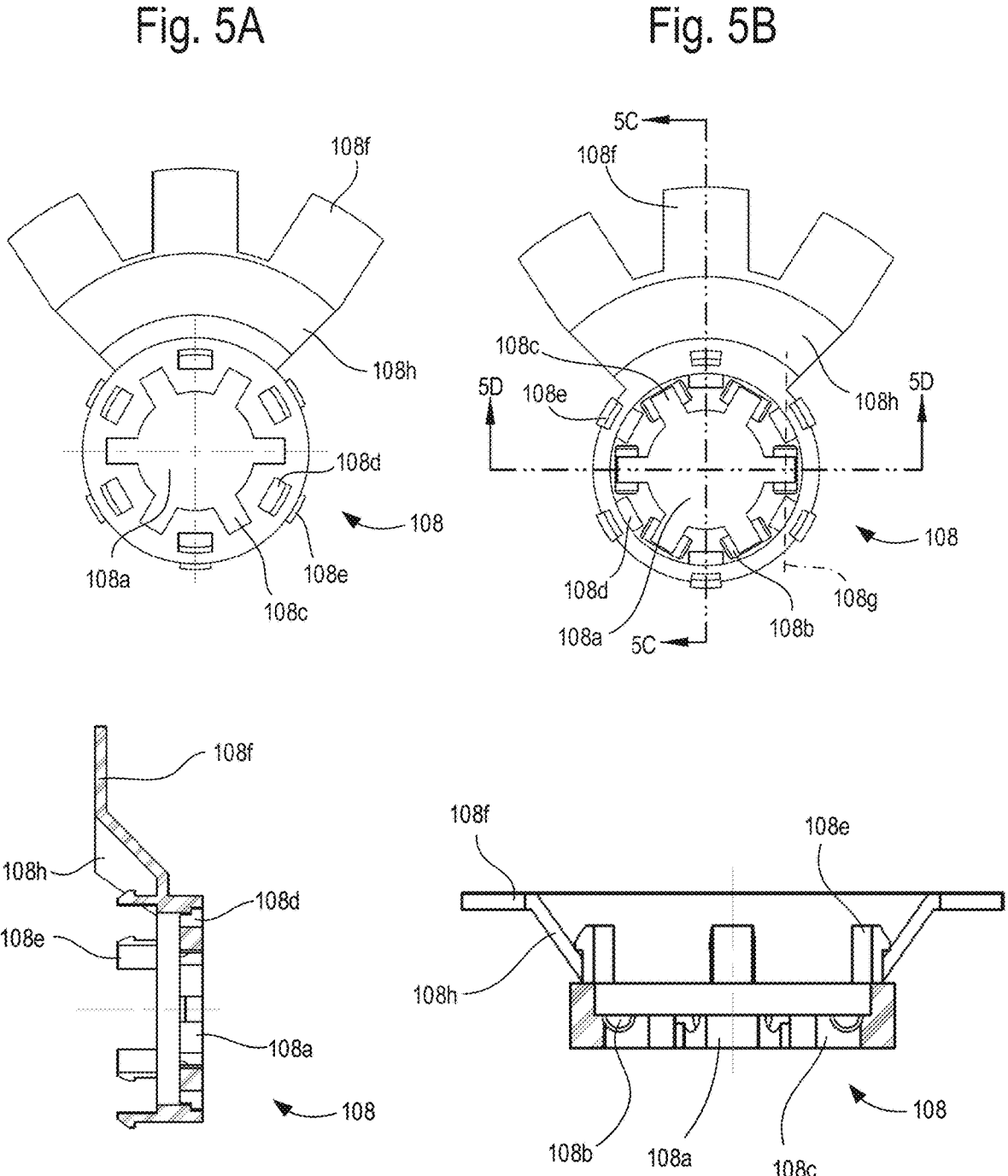
FIGS. 5A to 5D are bottom plan, top plan, side cross-section and front cross-section various views, respectively, of an exemplary port housing.

FIGS. 2A-3B show another embodiment of an expandable access port 100, which is similar to the embodiment of FIG. 1, but with certain alternative structures as described below. FIGS. 2A and 2B show the expandable access port 100 with the expandable port 104 in the contracted position, and FIGS. 3A and 3B show the expandable port 104 in the expanded position. In both cases, the introducer 106 is assembled to the remainder of the expandable access port 100. As shown in FIG. 2A, the expandable port 104 extends along the longitudinal axis 100a in a distal direction D from the activation assembly 102. To help in explaining features herein, FIG. 2A also illustrates a proximal direction P, which is opposite the distal direction D.

FIG. 3B also shows a navigation probe 126 in place inside the introducer 106, and a guidance arm 128 mounted to the activation assembly 102. The guidance arm 128 also serves as a tracking device to directly monitor the position of the expandable access port 100 after the navigation probe 126 is removed, or if the device is used without a navigation probe 126. Details of the guidance arm 128 are provided below.

An exemplary embodiment of an activation assembly 102 is shown in FIGS. 4A-8B. The activation assembly 102 generally includes a port housing 108 and a lock ring 110 that are assembled together to form an activation arm mounting body, and an activation ring 112 that is movably mounted to the activation arm mounting body. The port housing 108 defines a port housing opening 108a, the lock ring 110 defines a lock ring opening 100a, and the activation ring 112 defines an activation ring opening 112a. The port housing opening 108a, lock ring opening 100a and activation ring opening 112a are aligned, and each surrounds or defines at least a portion of the activation assembly opening 102a.

In this example, the activation ring 112 is rotationally mounted to the activation arm mounting body, such as explained below, such that the activation ring 112 can be rotated relative to the activation arm mounting body and about the longitudinal axis 100a, between a first activation ring position and a second activation ring position. The first activation ring position is shown in FIGS. 2A and 2B, and in this position the expandable port 104 is in the contracted position. The second activation ring position is shown in FIGS. 3A and 3b, and in this position the expandable port 104 is in the expanded position.

As best shown in FIGS. 4A-5D, the port housing 108 comprises a generally ring-shaped structure that defines the port housing opening 108a. The port housing 108 includes a plurality of first pivot recesses 108b that surround the longitudinal axis 100a. Similarly, the lock ring 110 is a generally ring-shaped structure that defines the lock ring opening 100a, and includes a plurality of second pivot recesses 110b that surround the longitudinal axis 100a. The port housing 108 and lock ring 110 are secured together, such that the first pivot recesses 108b and second pivot recesses 110b collectively form cavities that each define a respective pivot locations 102b (see FIGS. 13 and 14). The pivot locations 102b may be cylindrical (as shown), spherical, or have any other shape suitable to hold a corresponding pivot to rotate about a fixed axis. The pivot locations 102b are distributed around the longitudinal axis 100a, and each defines a respective pivot axis 108g (see FIGS. 5B and 6A). The pivot axes 108g lie in a common plane that is perpendicular to the longitudinal axis 100a. The pivot axes 108g are oriented such that they do not intersect the longitudinal axis 100a. Each pivot axis 108g also preferably extends tangentially to the longitudinal axis 100a (i.e., tangential to an imaginary circle having its center at the longitudinal axis 100a, with each pivot axis 108g being equidistant at its closest location to the longitudinal axis 100a. The pivot axes 108g also may be equidistantly positioned in the circumferential direction, such as shown in FIGS. 5B and 6A, which show six pivot axes 108g spaced at angles of 60° about the longitudinal axis 100a.

The lock ring 110 is secured to the port housing 108 by any suitable means. For example, the lock ring 110 is secured to the port housing 108 by locking tabs 110d that snap into respective locking tab receivers 108d, preferably in a manner that does not readily facilitate disconnection. In the illustrated example, the locking tabs 110d are provided on the lock ring 110, and the locking tab receivers 108d are provided on the port housing 108, but this arrangement may be reversed in whole or in part (i.e., one more of the locking tab receivers 108d may be on the lock ring 110, and one or more of the locking tabs 110d may be on the port housing 108). In other cases, the lock ring 110 and port housing 108 may be connected by adhesives, ultrasonic welding, rivets, reversible mechanical fasteners (e.g., screws), and so on.

The port housing 108 and/or lock ring 110 may include supplemental structures to increase their utility. For example, the port housing 108 may include one or more extensions 108f to which the introducer 106 and accessories (surgical tools, navigation devices, etc.) may be mounted. The extensions 108f also may be configured to secure to a clamp to hold the expandable access port 100 at a fixed location relative to the patient, operating table or surgical frame. Each extension 108f may include a lock mechanism 108j, or be shaped to connect to a lock provided on a different part. The details of such locks are not the subject of this disclosure, are well known in the art, and need not be described herein.

The activation arm mounting body (the connected port housing 108 and lock ring 110) may include multiple extensions 108f (e.g., two to four extensions 108f). The extensions 108f also may be arranged on one side of the activation arm mounting body (i.e., all within a 180° segment, or more preferably a 90° segment, about the longitudinal axis 100a). This provides greater access for the surgeon to operate without obstruction on the other side of the activation arm mounting body.

As noted above, the activation ring 112 is secured to the activation arm mounting body to rotate about the longitudinal axis 100a relative to the activation arm mounting body. In this example, the port housing 108 includes a plurality of sliding tabs 108e that snap into corresponding sliding tab receivers 112c in the activation ring 112. Each sliding tab receiver 112c comprises a circumferential slot having a relatively narrow width in the radial direction, and an end portion having a somewhat larger width in the radial direction. Each sliding tab 108e terminates at a hook that can be inserted into the wide end portion of each sliding tab receiver 112c, and then slid along the narrow portion of the sliding tab receiver 112c to rotate the activation ring 112 relative to the port housing 108. A hook or protrusion (not shown) may be provided between the wide and narrow portions of each sliding tab receiver 112c to prevent the respective sliding tab 108e from returning to the wide portion of the sliding tab receiver 112c. Thus, the parts cannot be disassembled accidentally during use, and more preferably cannot be disassembled under any normal circumstances (e.g., without breaking the parts).

In the illustrated example, the sliding tabs 108e are provided on the port housing 108, and the sliding tab receivers 112c are provided on the activation ring 112, but this arrangement may be reversed in whole or in part (i.e., one more of the sliding tabs 108e may be on the activation ring 112, and one or more of the sliding tab receivers 112c may be on the port housing 108). Also, the sliding tabs 108e and/or sliding tab receivers 112c may be provided on the lock ring 110, rather than the port housing 108.

In other embodiments, the activation ring 112 may be rotationally fixed to the activation arm mounting body using other connections. For example, the activation ring 112 may be captured in place against the activation arm mounting body by a central locking ring that threads into the activation arm mounting body. As another example, pins or screws may be inserted through the sliding tab receivers 112c and secured to the activation arm mounting body to capture the activation ring 112 in place. Other alternatives and embodiments will be apparent to persons of ordinary skill in the art in view of the present disclosure.

In still other embodiments, the activation ring 112 may be mounted to the activation arm mounting body move in other directions rather than the rotation described above. For example, the activation ring 112 may be mounted on rails to slide laterally relative to the activation arm mounting body.

Referring to FIG. 2A (as an example), the activation ring 112 preferably is located on the proximal side of the port housing 108. This allows unhindered access to the activation ring 112 when the activation arm mounting body is secured in place at the surgery site. Furthermore, the arrangement of sliding tabs 108e and sliding tab receivers 112c allows the activation ring 112 to rotate relative to the activation arm mounting body throughout its entire operative range of motion while remaining at a fixed location along the longitudinal axis longitudinal axis 100a. This arrangement minimizes the overall length of the expandable access port 100, and prevents the possible creation of unwanted axial forces along the longitudinal axis 100a as the activation ring 112 is rotated relative to the activation arm mounting body. While preferred, this arrangement is not required in all embodiments.

Figures 17A, 17B:
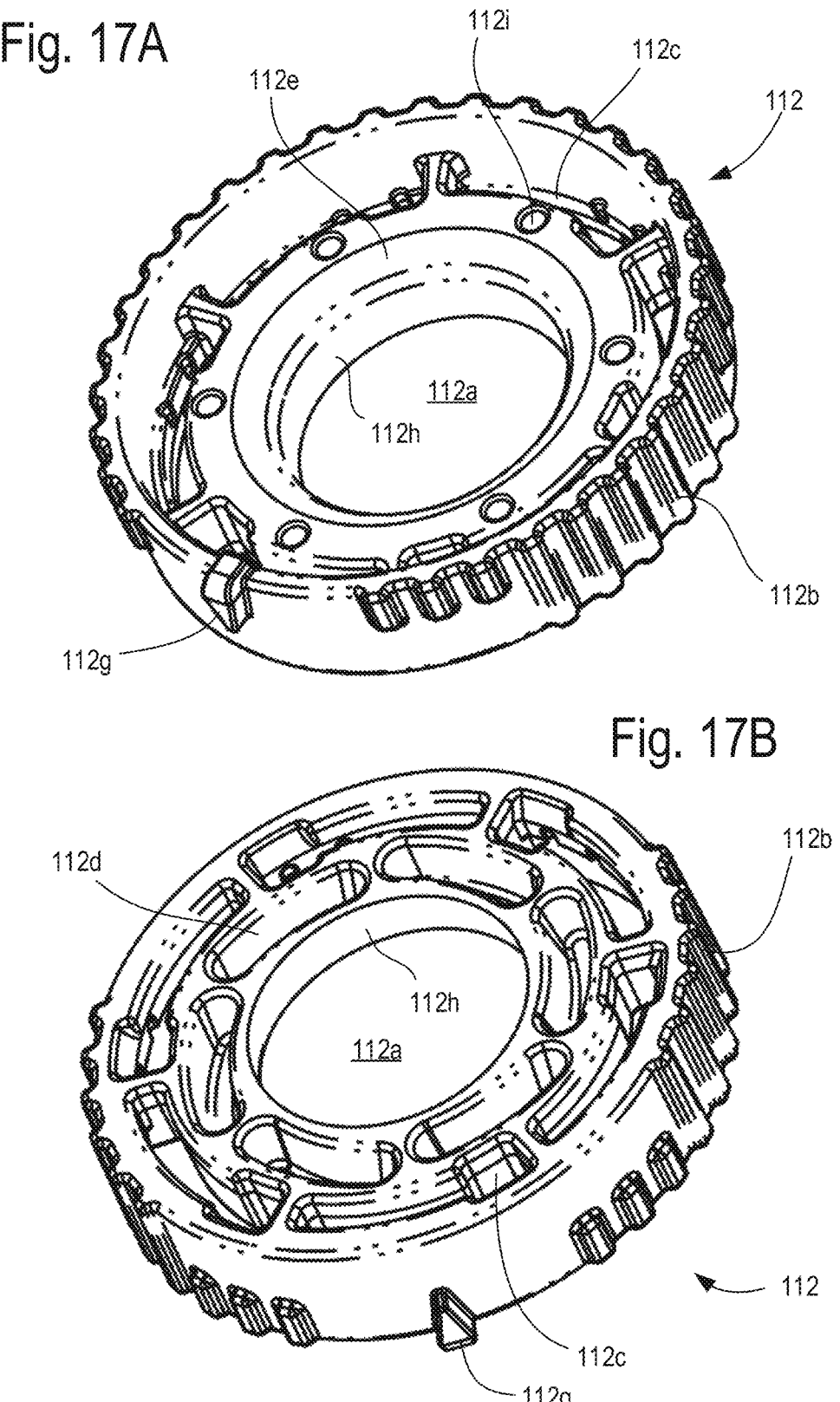
FIGS. 17A and 17B are top isometric and bottom isometric views, respectively, of another example of an activation ring.

As also shown in FIGS. 1, 17A and 17B, the activation ring 112 may have an outer surface defining a grip 112b, and the grip 112b optionally may be larger in diameter than an adjacent portion of the activation arm mounting body. This also facilitates ease of use, by providing a tactile distinction between the activation ring 112 and activation arm mounting body, and helping to ensure that rotational forces are not erroneously applied to the activation arm mounting body during operation, and increasing the surgeon's ability to firmly hold the activation ring 112.

As shown in FIG. 2A, one or more of the extensions 108f may extend to be positioned at, or spaced in the proximal direction from, a proximal side 112f of the activation ring 112. For example, one or more of the extensions 108f may be secured to the ring-like portion of the port housing 108 via an extension base 108h that extends in the proximal direction P. This arrangement makes the extensions 108f more accessible for connecting to accessories and position locks, and allows the expandable port 104 to be positioned deeper in the brain.

Figure 8A:
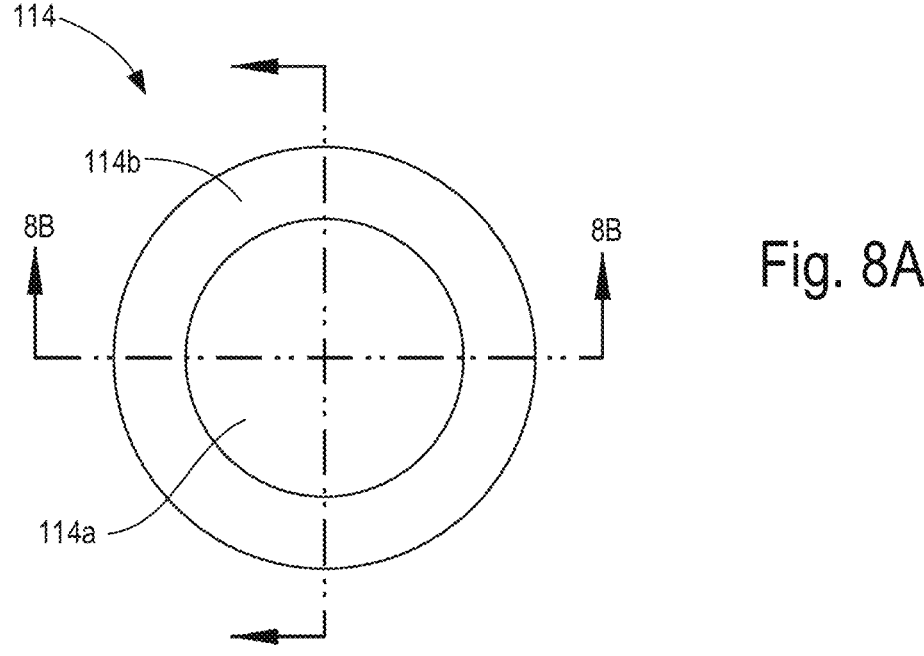
FIGS. 8A and 8B are top plan and side cross-section views, respectively, of an exemplary activation ring cover.
Figure 8B:
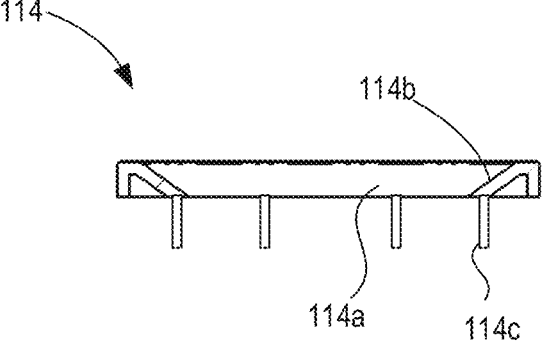
Figures 9A, 9B, 9C, 9D:
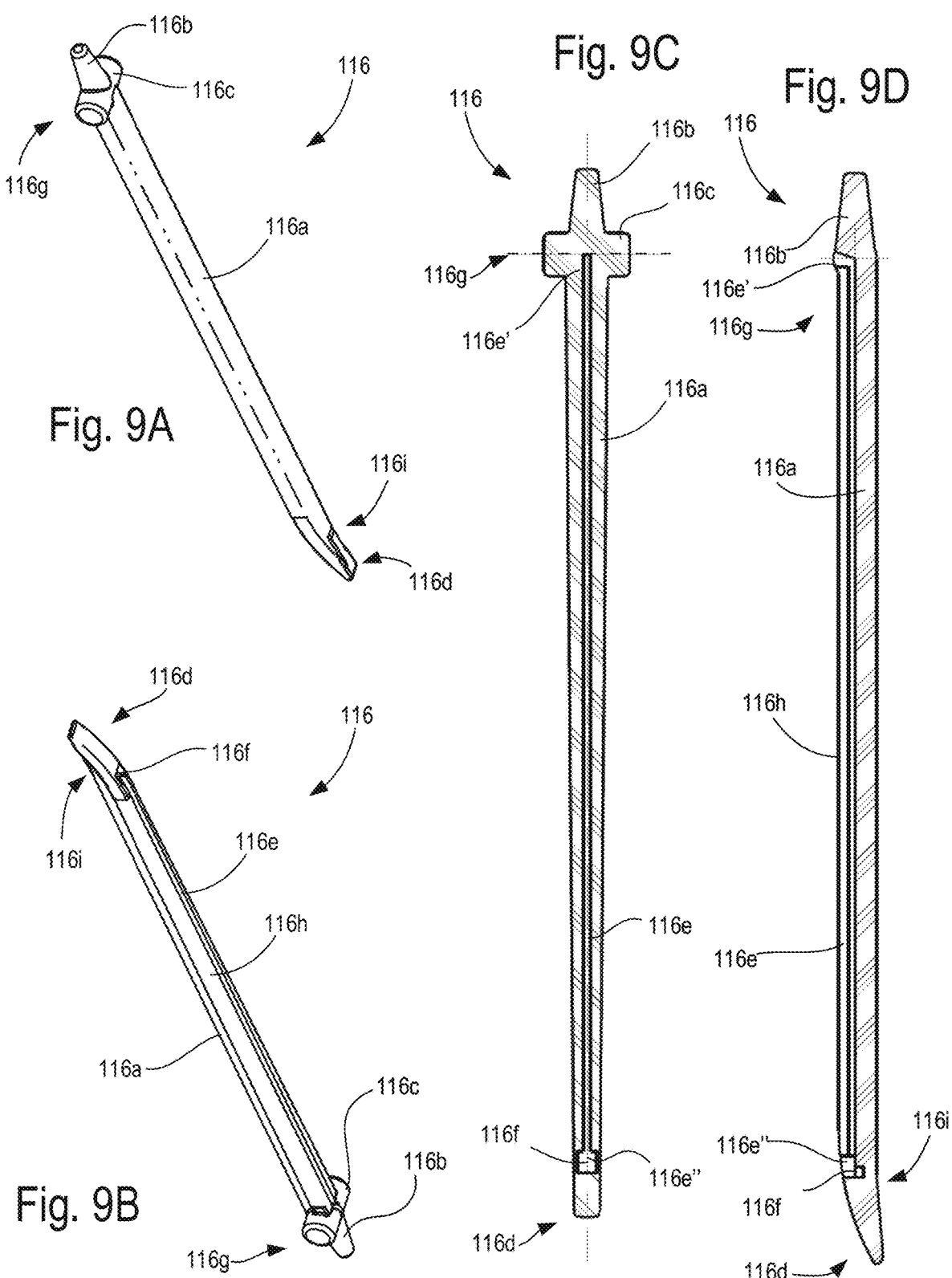
FIGS. 9A to 9D are top isometric, bottom isometric, side cross-section and front cross-section views, respectively, of an exemplary.
Figure 13:
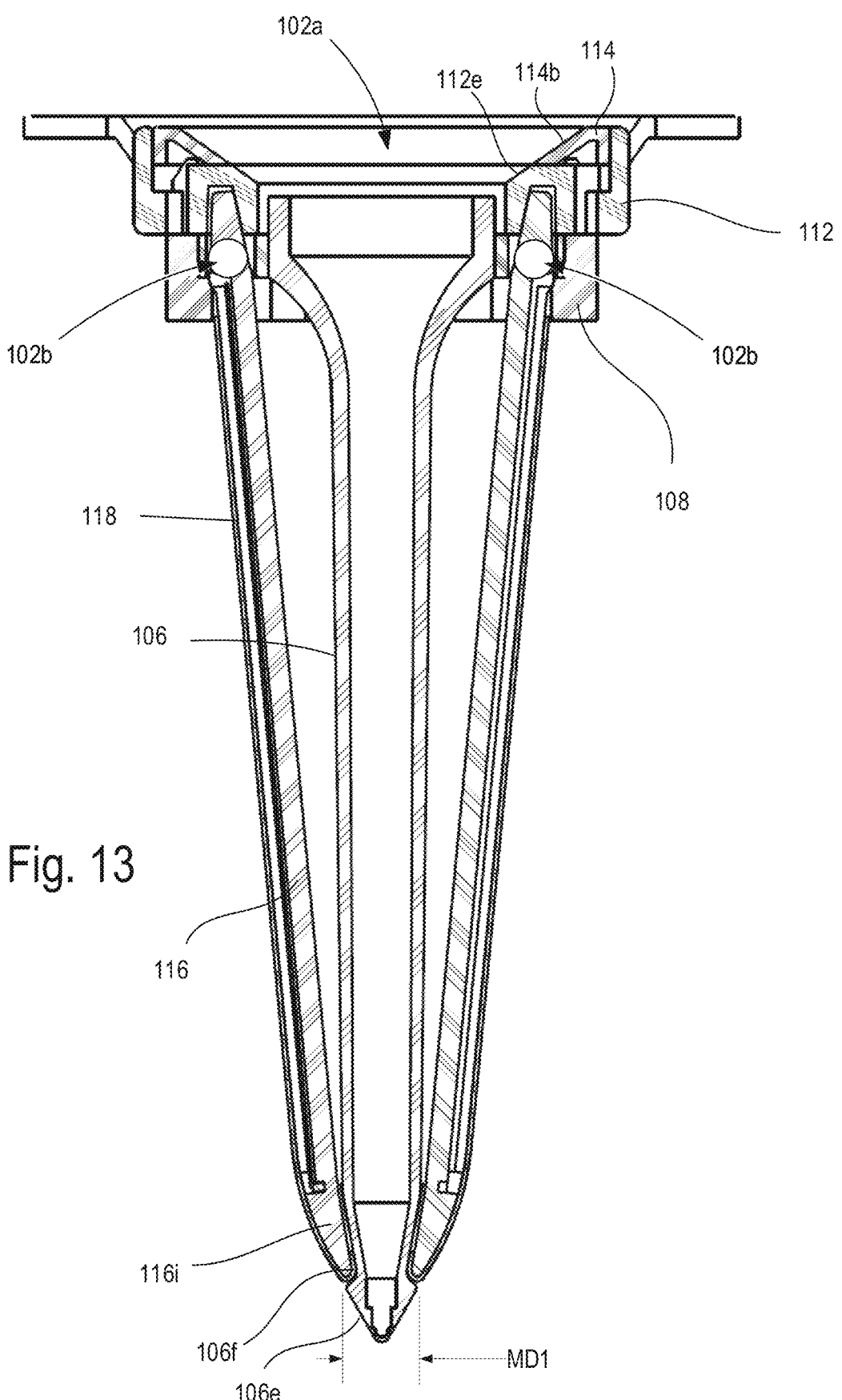
FIGS. 13 and 14 are side cross-section views of an assembled expandable access port shown with the expandable port in the contracted position and expanded position, respectively.
Figure 14:
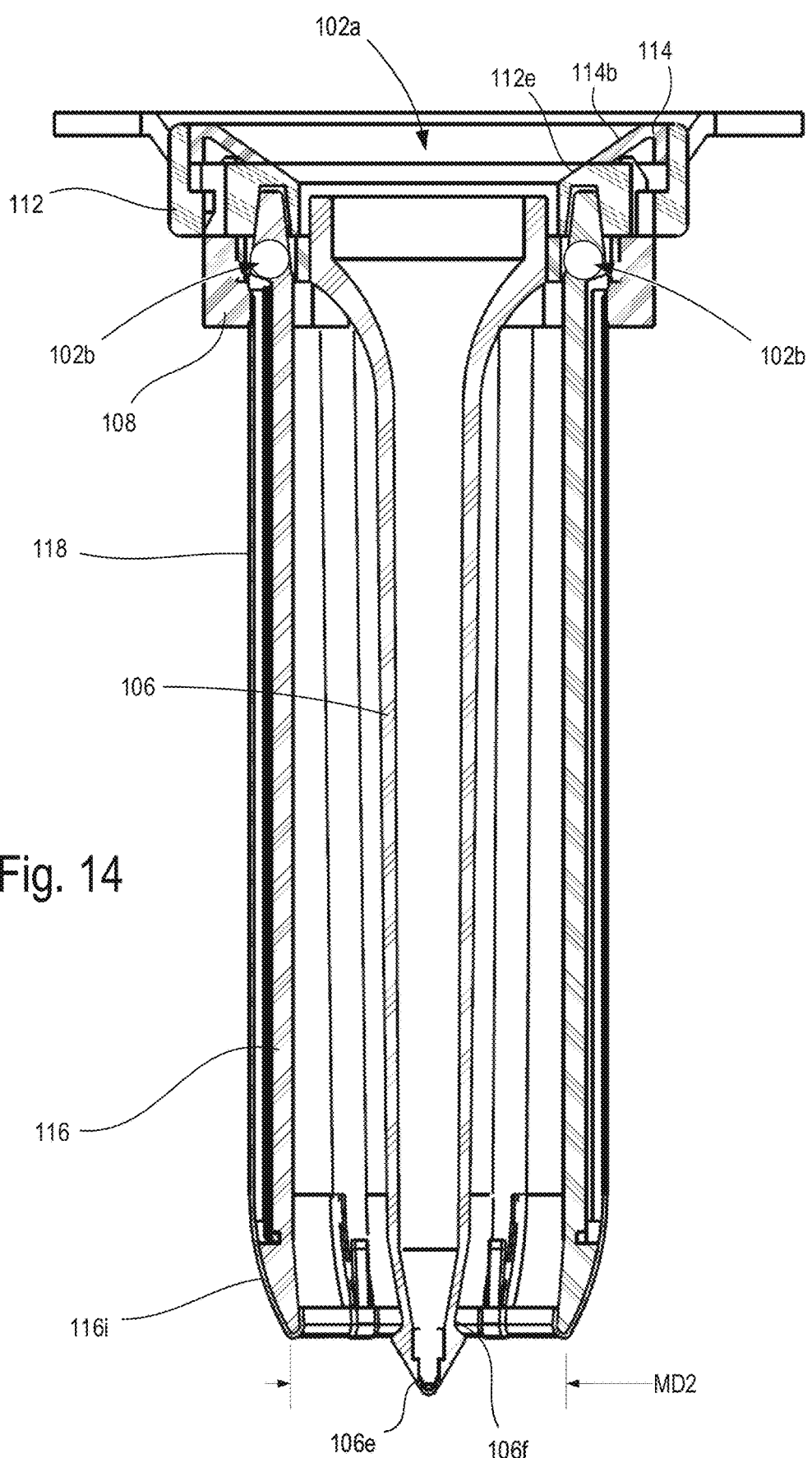
Figures 15A, 15B, 15C:
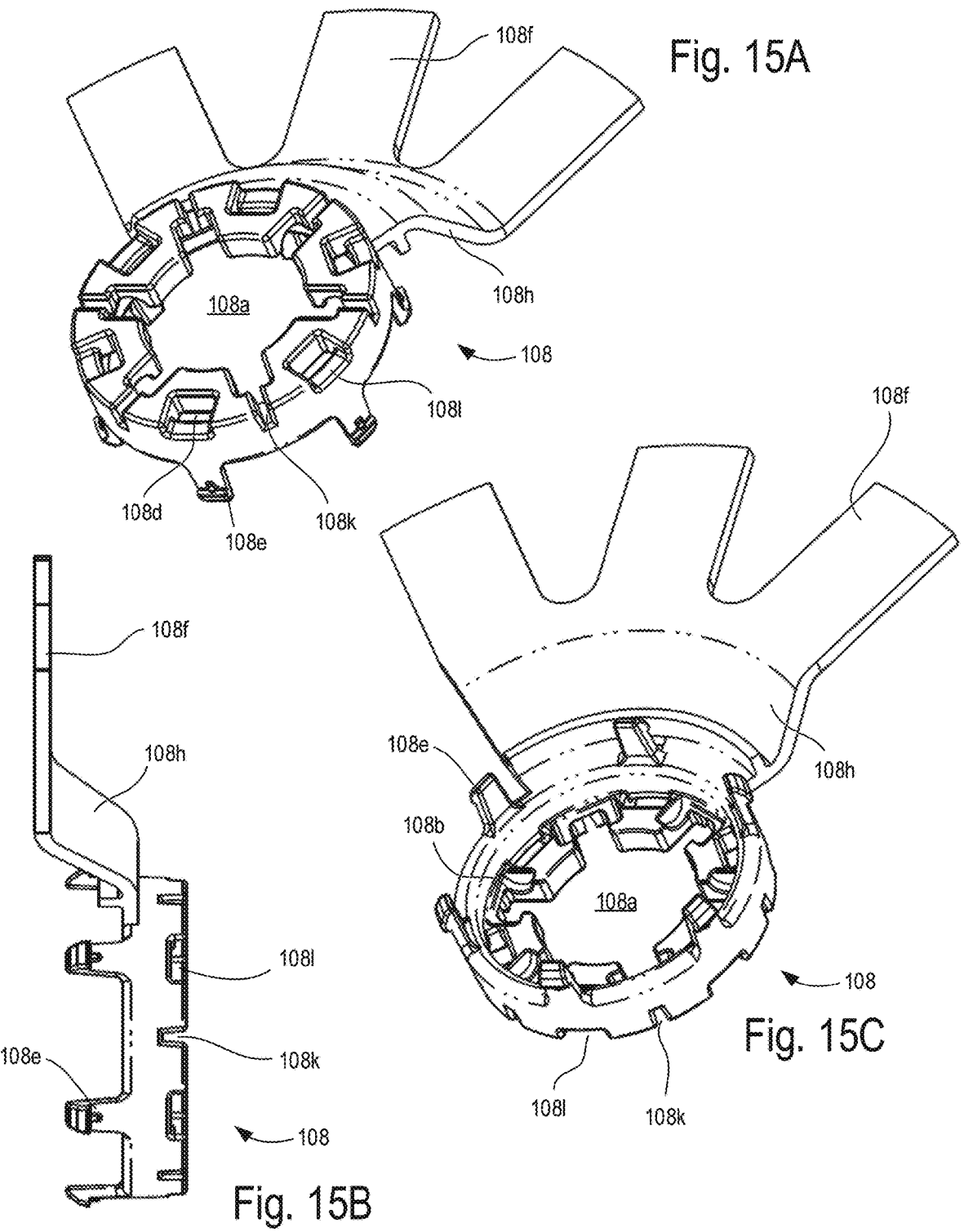
FIGS. 15A to 15C are bottom isometric, top isometric, and side views, respectively, of another example of a port housing.
Figures 16A, 16B, 16C:
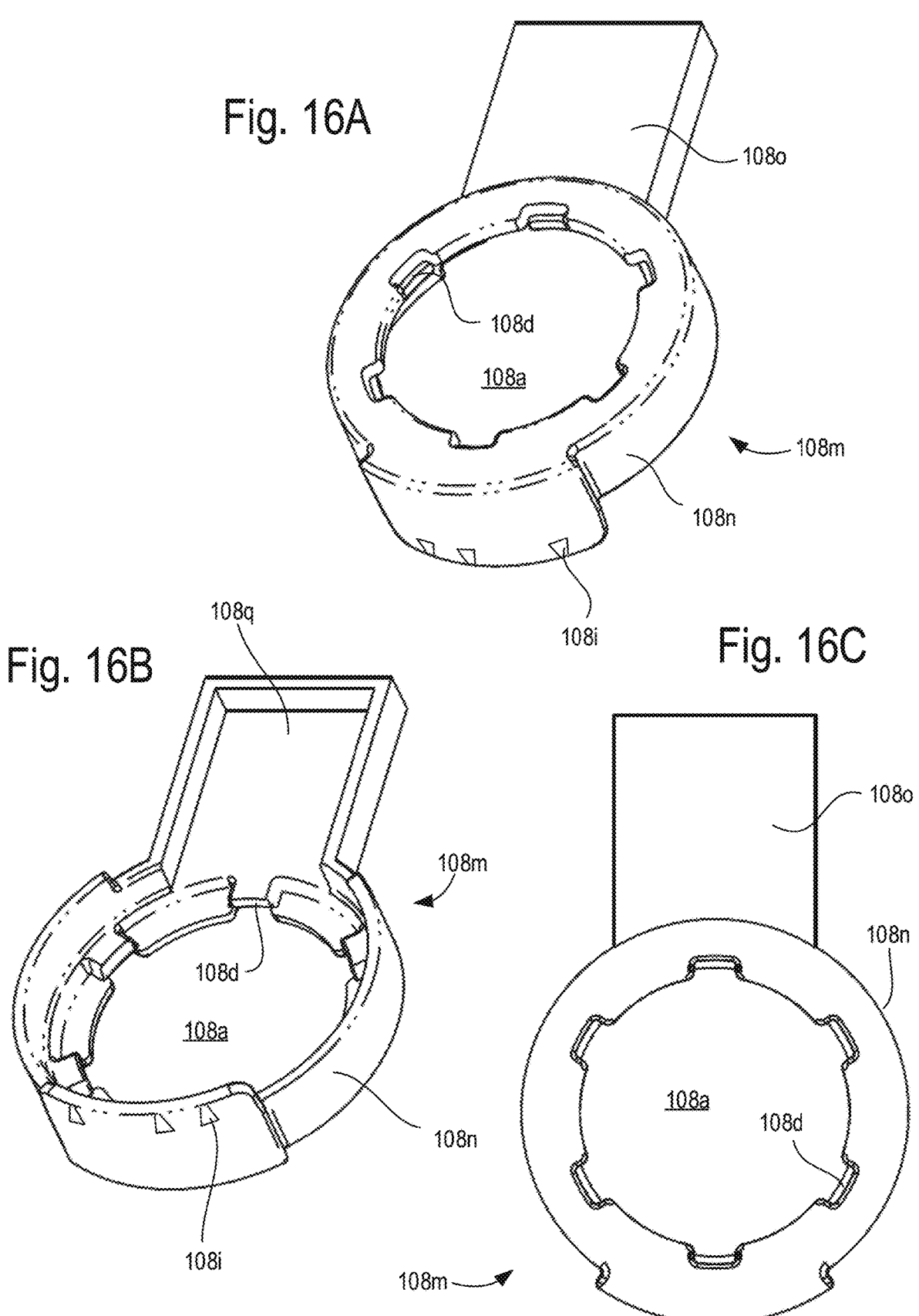
FIGS. 16A-16C are bottom isometric, top isometric and bottom plan views, respectively, of an exemplary connector housing.

Referring to FIGS. 8A-8B, the activation assembly 102 may include an activation ring cover 114 that covers the proximal side 112f of the activation ring 112. The activation ring cover 114 encloses the proximal sides of the sliding tab receiver 112c to prevent ingress of liquids or other matter that might obstruct operation of the activation ring 112. The activation ring cover 114 has an activation ring cover opening 114a that is concentric with the activation ring opening 112a. As best shown in FIGS. 13 and 14, the activation ring 112 may define a first tapered inlet surface 112e, and the activation ring cover 114 may define a second tapered inlet surface 114b that align to form a continuous tapered entry to the activation assembly opening 102a that decreases in diameter in the distal direction D. The activation ring cover 114 may be secured to activation ring 112 by any means, such as adhesives, snap fitment, ultrasonic welding, and so on. In this example, the activation ring cover 114 has pins 114c that are secured into holes 112i (see Figure in the adjacent face of the activation ring 112. One or all of the activation ring cover 114, first tapered inlet surface 112e and activation ring cover opening 114a also may be omitted.

Details of the expandable port 104 are now described in relation to FIGS. 9A-10D. The expandable port 104 generally includes a plurality of activation arms 116 and a membrane 118.

Each activation arm activation arm 116 comprises an elongated body 116a that extends in the distal direction D from a respective proximal arm end 116g to a respective distal arm end 116d. The proximal arm end 116g of each activation arm 116 is pivotally attached to the activation arm mounting body by a respective pivot 116c. In this example, each pivot 116c comprises a cylindrical body that is captured in place at a respective pivot location 102b and extends along the respective pivot axis 108g when the activation arm 116 is assembled to the activation arm mounting body (i.e., when the pivot 116c is captured between a respective first pivot recesses 108b and a respective second pivot recess 110b). This allows the activation arm 116 pivot about a respective pivot axis 108g. In other cases, the pivots 116c may comprise spherical bodies, pins that are provided separately and inserted through holes in the activation arm 116, and so on.

Each activation arm 116 is pivotable between a first arm position, in which the distal arm end 116d is a first distance D1 from the longitudinal axis 100a (see FIG. 2A), and a second arm position, in which the distal arm end 116d is a second distance D2 from the longitudinal axis 100a (see FIG. 3A). The second distance D2 is greater in magnitude than the first distance D1. The activation ring 112 is operable to move the activation arms 116 between their respective first and second arm position. More specifically, the activation ring 112 is rotatable between a first activation ring position in which the activation arms 116 are in their first arm positions, and a second activation ring position in which the activation arms 116 are in their second arm positions.

The activation arms 116 preferably cannot be moved any closer together than the first distance D1, so as to prevent the activation arms 116 from pinching brain tissue when the activation arms 116 are contracted without the presence of the introducer 106. This may be achieved, for example, by configuring the activation ring 112 such that it cannot move the activation arms 116 inwardly beyond the first position, by providing travel stops that contact the activation arms 116, or by making the activation arms such that they converge to contact each other along their circumferential sides in the first position. Other alternatives and embodiments will be apparent to persons of ordinary skill in the art in view of the present disclosure.

In this example, the activation ring 112 moves the activation arms 116 by engagement between respective cam slots 112d in the activation ring 112, and respective cam followers 116b at the proximal arm ends 116g of each slot 116e. As shown in FIG. 7A, the cam slots 112d are formed as recesses in the lower face of the activation ring 112. As the name suggests, each cam slot 112d is formed as an eccentric ramp about the longitudinal axis 100a. Specifically, each cam slot 112d extends about a portion of the activation ring opening 112*a* from a respective first cam slot end 112*d'* to a respective second cam slot end 112*d''*, and each respective second cam slot end 112*d''* is closer to the longitudinal axis 100*a* than each respective first cam slot end 112*d'*. The portion of the cam slot 112*d* between the first cam slot end 112*d'* and the second cam slot end 112*d''* may be straight, arced (shown) or have any other smooth continuous shape that performs the function described herein.

Each cam follower 116*b* extends into a respective one of the cam slots 112*d*, and rotating the activation ring 112 relative to the activation arm mounting body causes the cam slots 112*d* to drive the respective cam follower 116*b* towards or away from the longitudinal axis 100*a*, depending on the direction of rotation. In this case, each activation arm 116 acts as a class 1 lever, with the pivot 116*c* located between the cam follower 116*b* and the distal arm end 116*d*. Thus, when the cam followers 116*b* are located at the first cam slot ends 112*d'* the distal arm ends 116*d* are located in their respective first arm positions to contract the expandable port 104, and when the cam followers 116*b* are located at the second cam slot ends 112*d'* the distal arm ends 116*d* are located at their respective second arm positions to expand the expandable port 104. The cam slots 112*d* may include protrusions (not shown) that extend inwardly to provide one or more locations at which movement of the respective cam followers 116*b* is inhibited without applying a somewhat greater torque to the activation ring 112. Such protrusions can be positioned to establish predefined locations at which the activation arms 116 are held at one or more positions. For example, a protrusion may be provided to hold the activation arms 116 at their respective first or second positions, or anywhere between. Such protrusions can help the surgeon feel where the determined locations are. Other shapes, such as bends in the cam slots 112*d* can be provided to serve the same function.

The cam slots 112*d* may be shaped such that the cam followers 116*b* cannot back-drive the activation ring 112. Specifically, the angle of contact between the cam followers 116*b* and cam slots 112*d* may be selected such that a force applied to rotate the arm 116 generates a frictional load that prevents relative motion between the parts. This angle can be determined using conventional engineering principles (e.g., static coefficient of friction of an object on a ramp), and need not be describe in further detail herein.

The cam slots 112*d* also may be shaped to capture both sides the cam followers 116*b* such that the arms 116 cannot move freely in either direction. This prevents the arms 116 from moving beyond the position dictated by one side of the cam slot surface 112, and provides precise control of the arms' positions when rotating the activation ring 112 in alternating directions. This is expected to be beneficial to allow the surgeon to apply driving forces to precisely open and close the arms 116, preferably to any desired position, without relying on resilient forces (e.g., pressure from brain tissue) to collapse the arms 116 when it is desired to retract the arms. The cam slots 112*d* preferably also are configured to prevent the activation ring 112 from being moved to drive the activation arms 116 beyond their respective first position, such as by terminating each cam slot 112*d* at a closed end that stops on the cam follower 116*b*.

In other embodiments, the activation ring 112 can be configured to operate as a class 2 lever on the activation arms 116. For example, the cam slots 112*d* and cam followers 116*b* may be located between the pivot 116*c* and distal arm end 116*d* of each 116. Other alternatives and embodiments will be apparent to persons of ordinary skill in the art in view of the present disclosure.

The activation arm mounting body is configured to permit engagement between the cam slots 112*d* and cam followers 116*b*, such as by including a respective cam follower port 110*c* passing through the lock ring 110 to a proximal side 110*e* of the lock ring 110 to accommodate each cam follower 116*b*. Similarly, the activation arm mounting body is configured to permit the activation arms 116 to rotate distally from each pivot location 102*b*, such as by providing a respective activation arm port 108*c* on the distal side of each pivot location 102*b*. The cam follower ports 110*c* and/or activation arm ports 108*c* may be dimensioned to prevent excessive motion of the activation arms 116 if the activation ring 112 becomes detached from the activation arm mounting body.

In the shown example, the mechanism is configured such that all of the activation arms 116 move in unison at all times, thus ensuring that the device maintains a uniform generally circular shape during opening and closing. However, other embodiments may have features for adjusting the movement of, or disabling, one or more activation arms 116.

The membrane 118 surrounds the activation arms 116, and extends from a proximal membrane end 118*a* adjacent the activation assembly 102 to a distal membrane end 118*b* adjacent to the distal arm ends 116*d*. The membrane 118 comprises a flexible material that is expandable to permit the distal arm ends 116*d* to move from their respective first positions to their respective second positions. The membrane 118 may be secured to the activation arms 116, but preferably is overmolded onto the activation arms 116. Overmolding can be accomplished by placing the assembled activation assembly 102 and activation arms 116 into a mold that receives the activation arms 116, and injecting the membrane material into the mold to surround each activation arm.

The membrane 118 may comprise any suitable material that provides the desired degree of elongation. For example, the membrane 118 may comprise a thermoplastic elastomer, and/or an elastomer based on styrenic olefinic rubber and hydrogenated isoprene, containing polypropylene as a reinforcing agent and mineral oil as a plasticizer and processing aid.

As shown in FIG. 10D, the membrane 118 may be molded to have a generally circular cross-sectional profile, as viewed along the longitudinal axis 100*a*. The membrane 118 also may be shaped to have a respective distinct rib 118*d* located at each activation arm 116, and a respective wall 118*e* located between each adjacent pair of activation arms 116. As shown in FIG. 10D, each rib 118*d* may have a slightly larger diameter than the adjacent walls 118*e*, but this is not required. The ribs 118*d* may be molded to fully surround each 116, or they may only surround the respective outer radial surface 116*h* (i.e., the side facing away from the longitudinal axis 100*a*) of each 116. The membrane 118 may extend fully from the activation assembly 102 to the distal arm ends 116*d*, and may include a lip 118*c* that wraps around the distal arm ends 116*d*.

The membrane 118 also may include depth markers 118*f* (see FIG. 10B), which may be printed onto the membrane 118 or formed as bumps or protrusions. The depth markers 118*f* may include numerical characters (e.g. numbers indicating dimensions or relative locations) or other shapes (e.g., letters) to identify a respective position of each depth marker 118*f*. The depth markers also may comprises printed images or bumps/protrusions defined on the activation arms 116, that are visible through the membrane 108. Other alternatives and embodiments will be apparent to persons of ordinary skill in the art in view of the present disclosure.

The membrane 118 may have any suitable dimensions. For example, the membrane 118 may have a wall thickness of 0.024 inches to 0.008 inches, and more preferably of 0.020 inches to 0.012 inches, and even more preferably of 0.015 inches to 0.017 inches. In one embodiment, the membrane 118 may have a nominal wall thickness of 0.016 inches. It will be appreciated that these, and other dimensions herein, are subject to manufacturing tolerances, and the recitation of a specific number is intended to include typical variations due to manufacturing tolerances.

The membrane 118 also may be selected to provide a desirable degree of expansion to allow the activation arms 116 to open to the desired second arm positions. For example, the membrane 118 may be selected such that it expands by at least 250% of its original circumference at the point of greatest elongation (typically the distal membrane end 118b). More preferably, the membrane 118 may be selected such that it expands by at least 300%, and even more preferably by 350% at the point of greatest elongation. This expansion is illustrated in FIGS. 13 and 14 as the change between membrane diameter MD1 at the distal membrane end 118b in FIG. 13 and the membrane diameter MD2 at the distal membrane end 118b in FIG. 14.

The membrane 118 also may have and suitable size for use as a brain retractor. For example, the membrane 118 may have a contracted diameter of MD1 of 0.40 inches and an expanded diameter of 0.80 inches or more. In other cases, the membrane 118 may have a contracted diameter of MD1 of 0.30 inches and an expanded diameter of 0.90 inches or more. In still other cases, the membrane 118 may have a contracted diameter of MD1 of 0.25 inches and an expanded diameter of 1.00 inches or more.

Figure 12:
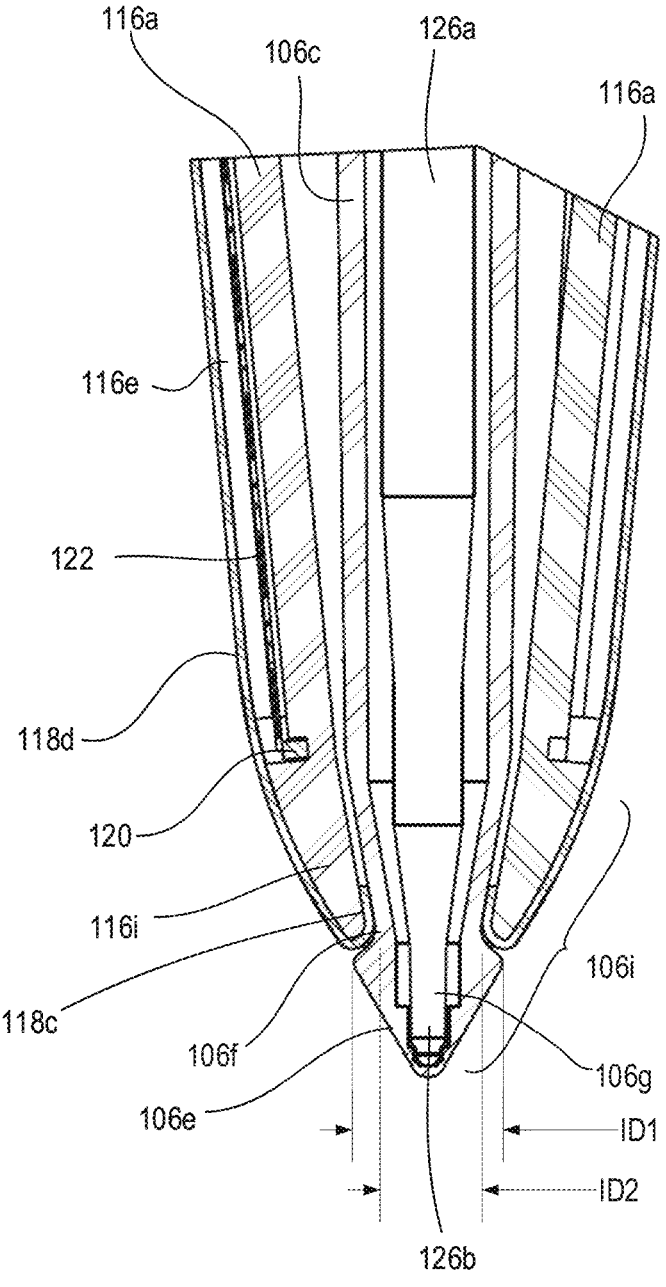
FIG. 12 is a detail side cross-section view of the distal end of an assembled expandable access port.

Referring back to FIGS. 9A-9D, and also to FIG. 12, one or more of the activation arms 116 may include a light 120. The light 120 may comprise a light emitting diode (LED), a terminal end of a light guide (e.g., a fiber optic cable), and so on. The activation arm 116 also may be formed as a light guide that is optically connected to a remote light source. In the shown example one or more of the activation arms 116 is formed of a transparent material (e.g., polycarbonate plastic), and has an LED light 120 located adjacent the distal arm end 116d. Light from the light 120 can pass through the distal arm end 116d to reach the surgery site. The distal arm end 116d also may be shaped or have surface treatments that help guide and distribute the light at the surgery site. Such shapes (e.g. Fresnel-type lenses or pyramidal bumps) and surface treatments for guiding and distributing light are known in the art.

The light 120 may be mounted to an inner surface of the activation arm 116 or at other locations. Preferably, the light 120 is mounted in a light receiver 116f that is recessed into the activation arm 116. The activation arm 116 has a slot 116e that leads to the light receiver 116f. The slot 116e is dimensioned to receive a light connector 122, such as a light guide or an electrical wire to power the light 120. In the shown example, the slot 116e extends along the activation arm 116 from a proximal slot end 116e' to a distal slot end 116e" adjacent the light receiver 116f. The proximal slot end 116e' may be located at or near the pivot 116c, or at any other location where access may be provided for a light connector 122 to enter the slot 116e.

The slot 116e may be located at any part of the activation arm 116, but preferably extends along the outer radial surface 116h. In this case, the membrane 118 can be over-molded over the outer radial surface 116h, such that a portion of the rib 118d is overmolded into the slot 116e. In this case, the engagement between the membrane 118 and the outer radial surface 116h helps hold the rib 118d at a fixed location as the activation arm 116 moves to its second (expanded) position. When fully constructed, the membrane 118 also encases the light 120 and the light connector 122 between the outer radial surface 116h and 118, thus holding the light 120 in place during use and keeping the light 120 away from contact with the brain tissue.

It will also be appreciated that one or more of the activation arms 116 may include a slot 116e or other shapes for the purpose of receiving an overmolded part of the membrane 118 (i.e., without a light 120), to enhance the connection between the activation arms 116 and the membrane 118.

Referring now to FIGS. 11A-14, an exemplary introducer 106 and its interaction with the remainder of the expandable access port 100 is described in detail. The introducer 106 extends from a proximal introducer end 106a to a distal introducer end 106b, and has a tubular wall 106c that defines a cannula 106d. The cannula 106d extends along the longitudinal axis 100a from the proximal introducer end 106a to a point adjacent to the distal introducer end 106b. The cannula 106d terminates at a probe tip receiver 106g that is configured to receive one or more different navigation probes 126. When fully inserted, the probe shaft 126a extends along the cannula 106d, and the probe tip 126b seats in the probe tip receiver 106g to hold the probe tip 126b at a fixed location.

At the distal introducer end 106b, the introducer 106 has an introducer tip 106e, which tapers to increase in size in the proximal direction P, to a diameter ID1. The introducer tip 106e optionally may have an opening that leads into the probe tip receiver 106g, which can be helpful to vent pressure in the brain as the expandable access port 100 is inserted. On the proximal side of the introducer tip 106e, the introducer 106 has an outer annular recess 106f. The annular recess 106f is region of the tubular wall 106c that has a reduced diameter ID2 as compared to the maximum diameter ID1 of the introducer tip 106e.

The introducer 106 is connected to the remainder of the expandable access port 100 by inserting it through the activation assembly opening 102a, and securing the proximal introducer end 106a to the activation arm mounting body. In this case, the introducer 106 has a mounting tab 106j that extends radially from the tubular wall 106c to overlie and connect to one of the extensions 108f, to thus hold the introducer 106 in an operative position in which the expandable access port 100 can be inserted into the brain to the surgery site. In the operative position, the cannula 106d extends along the longitudinal axis 100a, and the introducer tip 106e extends in the distal direction D beyond the distal arm ends 116d. This arrangement is best shown in FIGS. 12 and 13.

With the introducer 106 in the operative position and the activation arms 116 in their respective first (contracted) positions, at least a portion of each distal arm end 116d is received within the annular recess 106f. This helps prevent the distal arm ends 116d from pulling on the brain tissue as the expandable access port 100 is inserted and prevents the brain tissue from pulling the activation arms 116 away from the introducer 106. Furthermore, each activation arm 116 also preferably includes an inward bend 116i at its distal arm end 116d, to help form a continuous tapered outer wall 106i extending from the distal introducer end 106b to a point along or behind the annular recess 106f. Each inward bend 116i comprises a portion of the respective activation arm 116 that is bent towards the longitudinal axis 100a to form a tapered portion of the outer radial surface 116h. In the shown example, the inward bend 116*i* is located at the end of a straight portion of the elongated body 116*a*. At least a portion of each inward bend 116*i* extends into the annular recess 106*f*, and the outer surface of the inward bend 116*i* (or portion of the membrane 118 surrounding the inward bend 116*i*) preferably forms a curved taper that transitions gradually between the taper angle of the introducer tip 106*e* and the taper angle of the straight portion of the outer radial surface 116*h*. However, it is also envisioned that the inward bend 116*i* may meet the slot 116*e* or the straight portion of the elongated body 116*a* at a distinct angle.

The foregoing arrangement provides several benefits. First, the continuous tapered outer wall 106*i* portion formed by the introducer tip 106*e* and inward bend 116*i* presents an atraumatic shape for inserting the expandable access port 100 into the brain. At the same time, the inward bends 116*i* can be made relatively wide, as compared to arms that extend straight to the introducer tip 106*e*, which helps increase the stiffness of the activation arms 116 at their distal arm ends 116*d*. Still further, the inward bends 116*i* also present a curving surface at the brain tissue when the expandable port 104 is expanded, such as shown in FIG. 14, which is expected to reduce the likelihood and/or severity of ischemia along the distal arm ends 116*d* and distal membrane end 118*b*.

The introducer 106 also may include other features to increase its utility. For example, the proximal introducer end 106*a* may be formed with a tapered inlet 106*h* to help guide a navigation probe 126 into the cannula 106*d*. The introducer 106 also may be formed to mate closely with the activation assembly 102 to hold the introducer 106 against movement perpendicular to the longitudinal axis 100*a* (i.e., lateral movement). For example, the introducer 106 may have an introducer outer face 106*l* that contacts a corresponding lock ring inner face 110*f* of activation ring inner face 112*h* to prevent lateral movement of the proximal introducer end 106*a* relative to the activation assembly 102. One of more of the introducer outer face 106*l*, lock ring inner face 110*f* and activation ring inner face 112*h* also may be tapered to decrease in size in the distal direction D. For example, the introducer outer face 106*l* and lock ring inner face 110*f* may have matching taper angles TA, or all three of the introducer outer face 106*l*, lock ring inner face 110*f* and activation ring inner face 112*h* may have matching taper angles. In this case, when the introducer 106 is assembled to the rest of the expandable access port 100, the matching taper angles prevent the introducer 106 from moving laterally relative to the rest of the expandable access port 100, and also hold the introducer 106 at a fixed location along the longitudinal axis 100*a* to prevent it from being inserted beyond the desired location. The matching taper angles also may inhibit or prevent relative rotation of the introducer 106, lock ring 110 and activation ring 112, to thereby prevent accidental rotation of the activation ring 112 as the expandable access port 100 is inserted into place.

It will be appreciated that a structure comparable to the lock ring inner face 110*f* may instead be provided at any other part of the activation assembly 102, such as by being formed as an inner surface wall or walls of the port housing 108 and/or activation ring cover 114. Other alternatives and embodiments will be apparent to persons of ordinary skill in the art in view of the present disclosure.

Other embodiments of certain features are shown in FIGS. 15A through 18B. These embodiments may be used together, or in combination with other embodiments described herein.

FIGS. 15A-16C show an embodiment of a port housing 108. This embodiment is similar to the embodiment of FIGS. 5A-5D, but includes a connector housing 108*m* and other features to facilitate connection of a light 120 to a power source or a light guide to a light source. In this case, the port housing 108 includes a slot 108*k* extending from one or more of the first pivot recesses 108*b*, preferably in a generally radial direction. When the port housing 108 is assembled with the lock ring 110, the slots 108*k* each provide access for a respective light 120, such as an electrical wire or a fiber optic cable.

The connector housing 108*m* is secured to the remainder of the activation arm mounting body to a form a housing interior space 108*p* (see FIG. 18A) that receives the light connector 122. More specifically, the connector housing 108*m* has a connector housing outer body 108*n* that contains the portion of the port housing 108 through which the slots 108*k* extend. The connector housing outer body 108*n* also has a connector housing opening 108*q* through which the light connector 122 passes to connect to a power supply or light supply. The connector housing opening 108*q* may be located at any suitable location. In this case, the connector housing opening 108*q* is provided on a connector housing extension 108*o* that extends radially from the remainder of the port housing 108. The connector housing extension 108*o* optionally may be positioned under the extensions 108*f* to provide relatively little obstruction to the surgical theater.

In this embodiment, the locking tab receivers 108*d* are provided on the connector housing 108*m*, such that the locking tab 110*d* of the lock ring 110 connects to the connector housing 108*m* with the main body of the port housing 108 captured in place between the lock ring 110 and the connector housing 108*m*. The locking tab receivers 108*d* may be recessed towards the lock ring 110, and configured to fit into matching tab receiver recess 108*l* formed in the bottom of the main body of the port housing 108, to thereby reduce the overall height of the assembled port housing 108.

The activation arm mounting body also includes one or more body position indicators 108*i*. The body position indicators 108*i* are visual, and optionally also tactile, indicators to show the rotational position of the activation ring 112 relative to the port housing 108. As shown in FIGS. 17A-17B, the activation ring 112 likewise has one or more ring position indicators 112*g*, which align with the body position indicators 108*i* in different ways depending on the rotational position of the activation ring 112 relative to the port housing 108. In this case, the activation ring 112 has a single ring position indicator 112*g*, and the port housing 108 has three body position indicators 108*i* arranged at different circumferential locations. The body position indicators 108*i* are, in this case, provided on the connector housing 108*m*, but alternatively may be provided on the main body of the port housing 108 or elsewhere on the activation arm mounting body.

When the activation assembly 102 is assembled, the ring position indicator 112*g* is positioned adjacent to a first body position indicator 108*i'* when the activation ring 112 is in the first position (i.e., when the expandable port 104 is contracted), and a second body position indicator 108*i''* when the activation ring 112 is in the second position (i.e., when the expandable port 104 is expanded). The ring position indicator 112*g* aligns with a third body position indicator 108*i'''*, which is located between the other two body position indicators 108*i'*, 108*i''*, when the activation ring 112 is in an intermediate position. This third body position indicator 108*i'''* may be helpful when the surgeon does not wish to fully expand the expandable port 104. More or fewer body position indicators 108*i* may be used in other embodiments.

The intermediate position beneficially may be the position at which the distal arm ends 116*d* and the membrane lip 118*c* (if present) are just radially outside the annular recess 106*f* in the introducer 106. Stated differently, the intermediate position may be the position at which the distal arm ends 116*d* and membrane lip 118*c* (if present) are spaced radially by the maximum diameter ID1 of the introducer tip 106*e* to thereby allow the introducer 106 to be freely removed in the proximal direction without interfering with the arms 116 and other portions of the expandable structure. This allows the surgeon to open the arms 116 by the minimum amount necessary to remove the introducer 106, as may be helpful in some circumstances.

FIGS. 17A-17B also show the activation ring 112 having knurling on the grip 112*b* to enhance the feel and usability of the activation ring 112. The knurling may be replaced by other structures to enhance grip, such as a rubber or other high-friction ring, or the like. The activation ring 112 also (or alternatively) may include one or more handles or levers (not shown) for operating the activation ring 112. The activation ring 112 also includes a ring position indicator 112*g*.

Figures 18A, 18B:
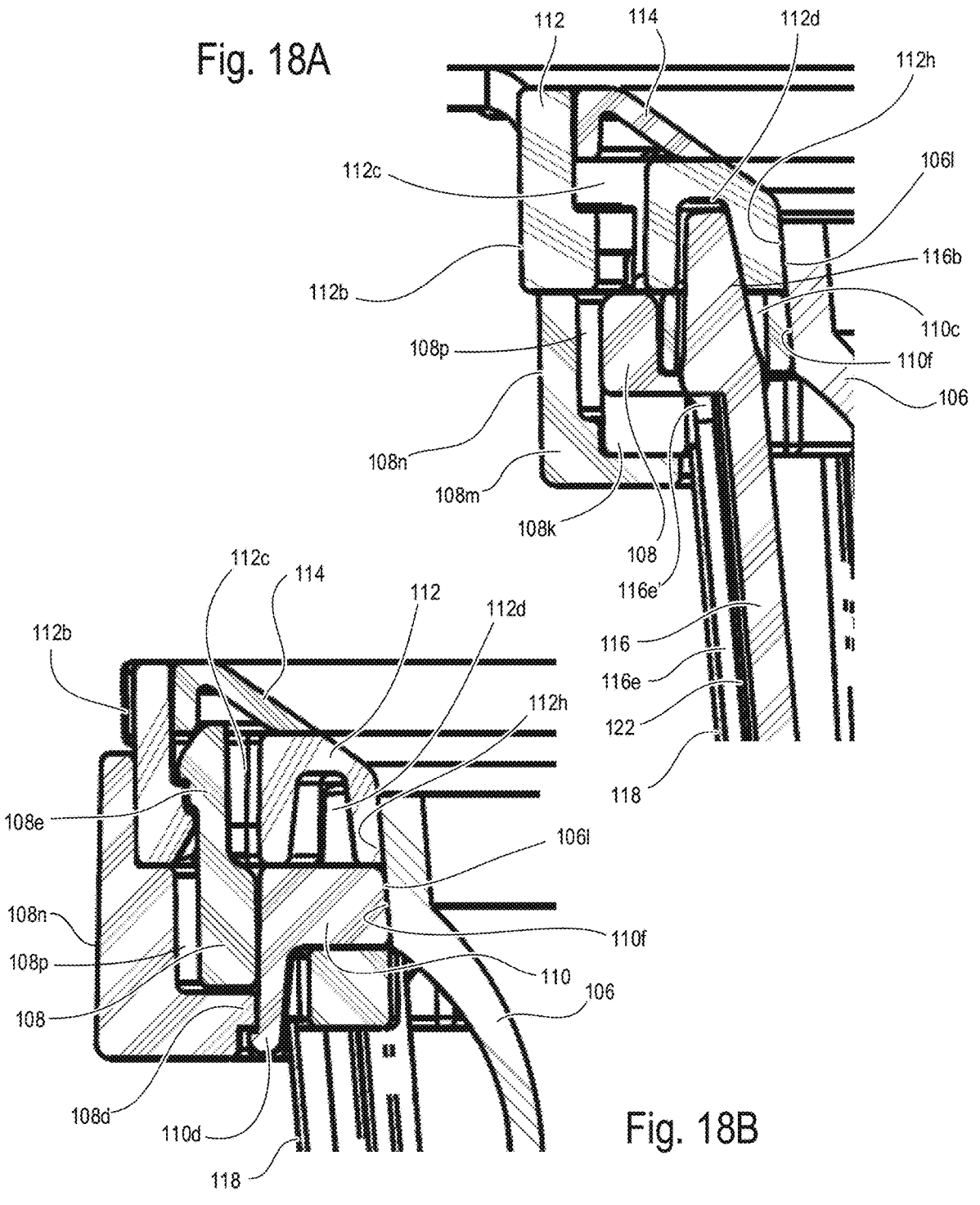
FIGS. 18A and 18B are detail side cross-section views of the proximal end of an assembled expandable access port, shown along two different cross-section planes.

FIGS. 18A-18B are cross-sectional views that show the assembly of the various parts in detail. Here, it can be seen that the lock ring 110 connects via locking tabs 110*d* to the locking tab receivers 108*d* to secure the connector housing 108*m* to the rest of the port housing 108, and capture the main body of the port housing 108 in place. Also, FIG. 18A shows the housing interior space 108*p* formed between the connector housing 108*m* and the rest of the port housing 108, and how the slot 108*k* aligns with the proximal slot end 116*e'* of the associated activation arm 116 to provide a passage for the light connector 122. The connection of the port housing 108 to the activation ring 112 via the sliding tabs 108*e* is also shown. These figures also show how the cam followers 116*b* extend through the cam follower ports 110*c* to engage the cam slots 112*d*, the interaction between the tapered activation ring inner face 112*h*, introducer outer face 106*l* and lock ring inner face 110*f*, and other features.

Figures 19A, 19B, 19C:
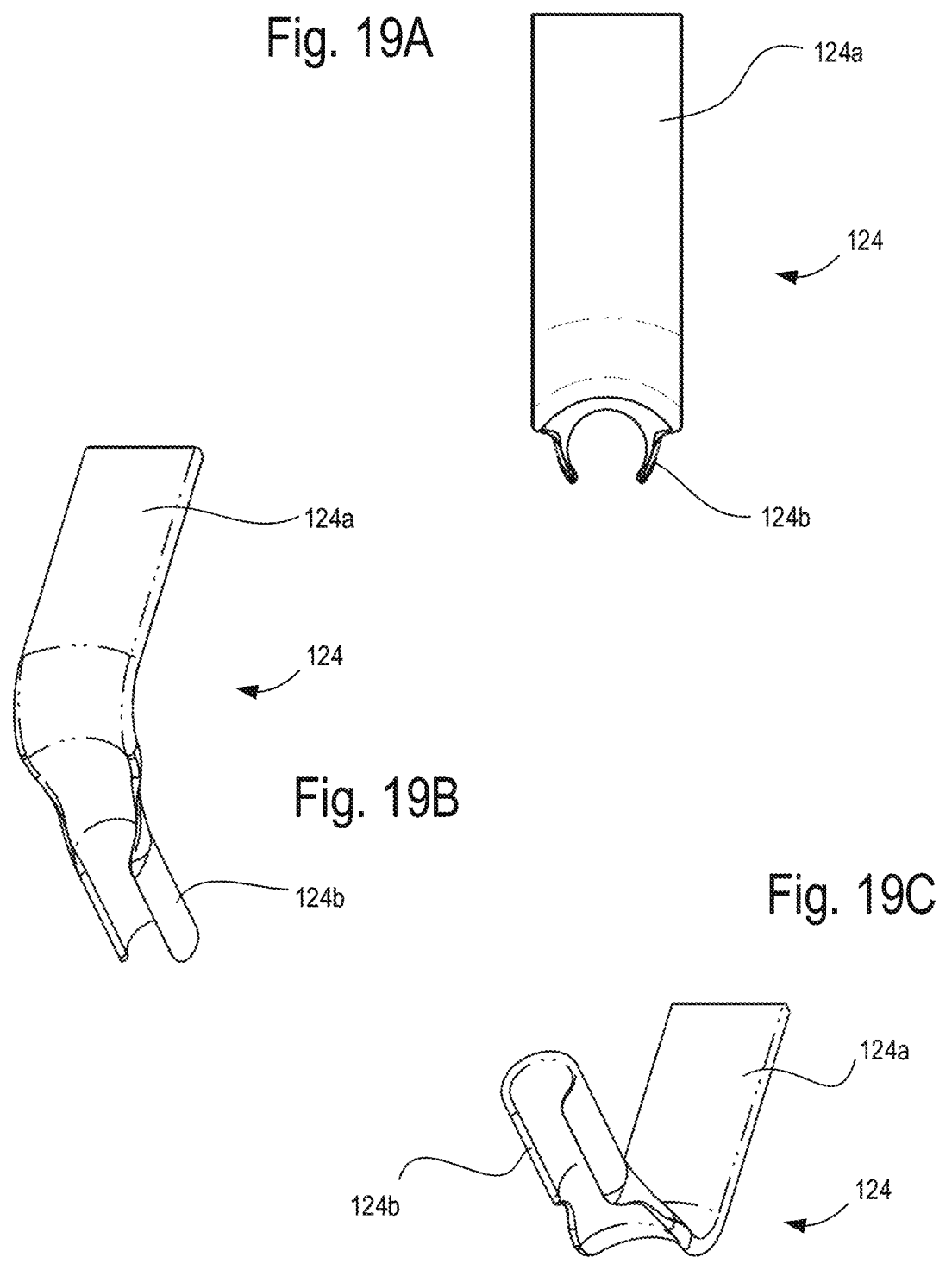

FIGS. 19A-19C show an example of a surgical tool mount 124 that may be used with embodiments of an expandable access port 100. The surgical tool mount 124 includes a tab 124*a* that is configured to secure to an extension 108*f*, and a connector 124*b* that is configured to secure to or guide a surgical instrument, such as an endoscope, a suction hose, a light, and so on. In this case, the connector 124*b* comprises a cylindrical clip having an open side to allow the clip to flex and generate a restoring force to hold the instrument in place. Other embodiments may have different constructions, as will be apparent to persons of ordinary skill in the art in view of the present disclosure.

Figures 20A, 20B:
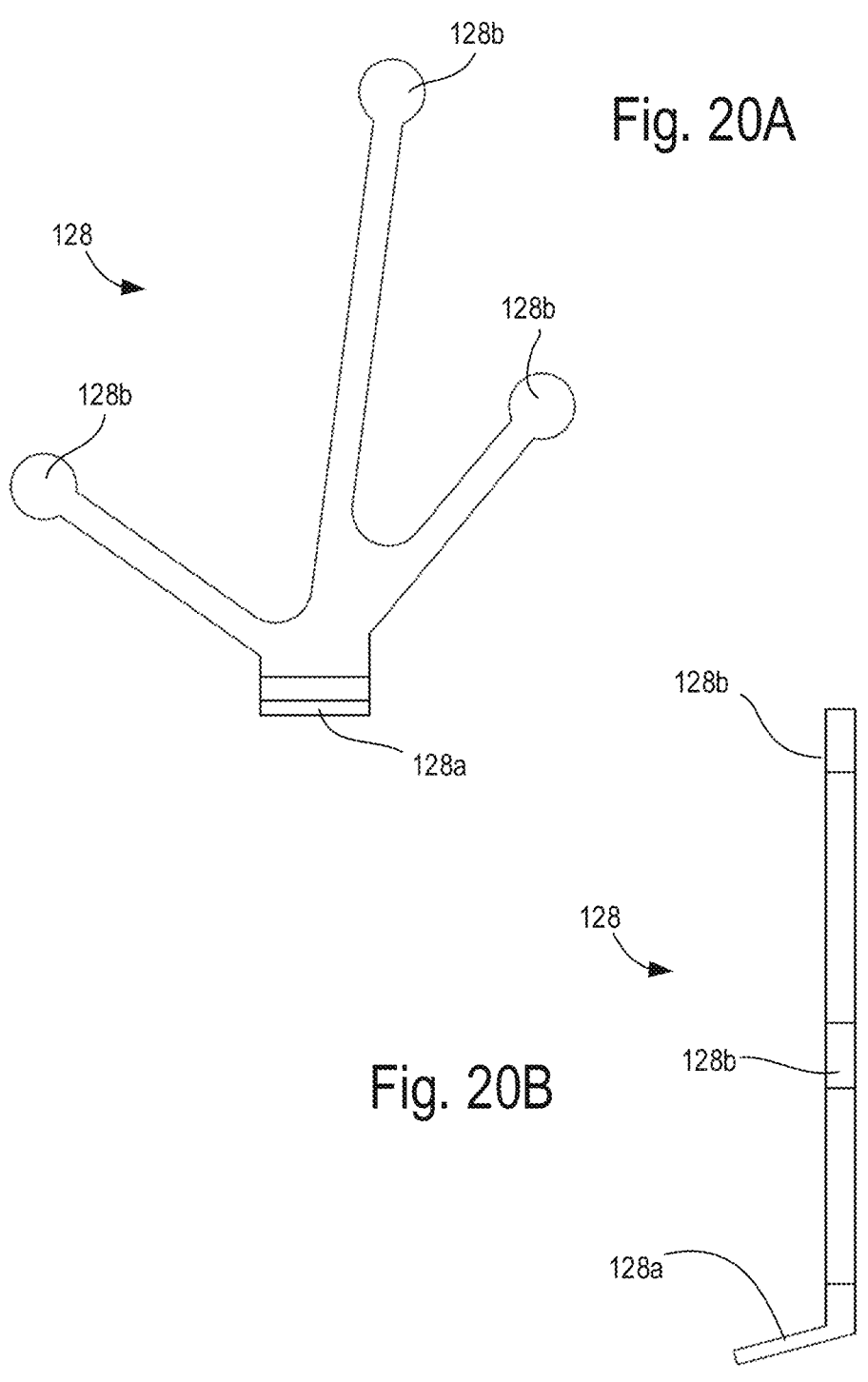
FIGS. 20A and 20B are front and side views of an exemplary guidance arm.

FIGS. 20A-20B show an example of a guidance arm 128 that may be used with embodiments of an expandable access port 100. The guidance arm 128 includes a tab 128*a* that is configured to attach to the expandable access port 100, such as by securing it to an extension 108*f*, and an array of indicators 128*b*, such as reflective spheres or discs, that are used for visually tracking the position of the guidance arm 128 via a stereotactic navigation system, as known in the art. The indicators 128*b* preferably are mounted to extend from the tab 128*a* at an angle extending away from the longitudinal axis 100*a*, to help clear the area above the expandable access port 100 for surgical operations. Similar indicators 128*b* may also be used in conjunction with a navigation probe 126, as also known in the art. In addition, the indicators 128*b* may be directly integrated into the body of the expandable access port 100, such as by mounting them on an extension 108*f* or multiple extensions 108*f*. Other alternatives and embodiments will be apparent to persons of ordinary skill in the art in view of the present disclosure.

Figures 21A, 21B:
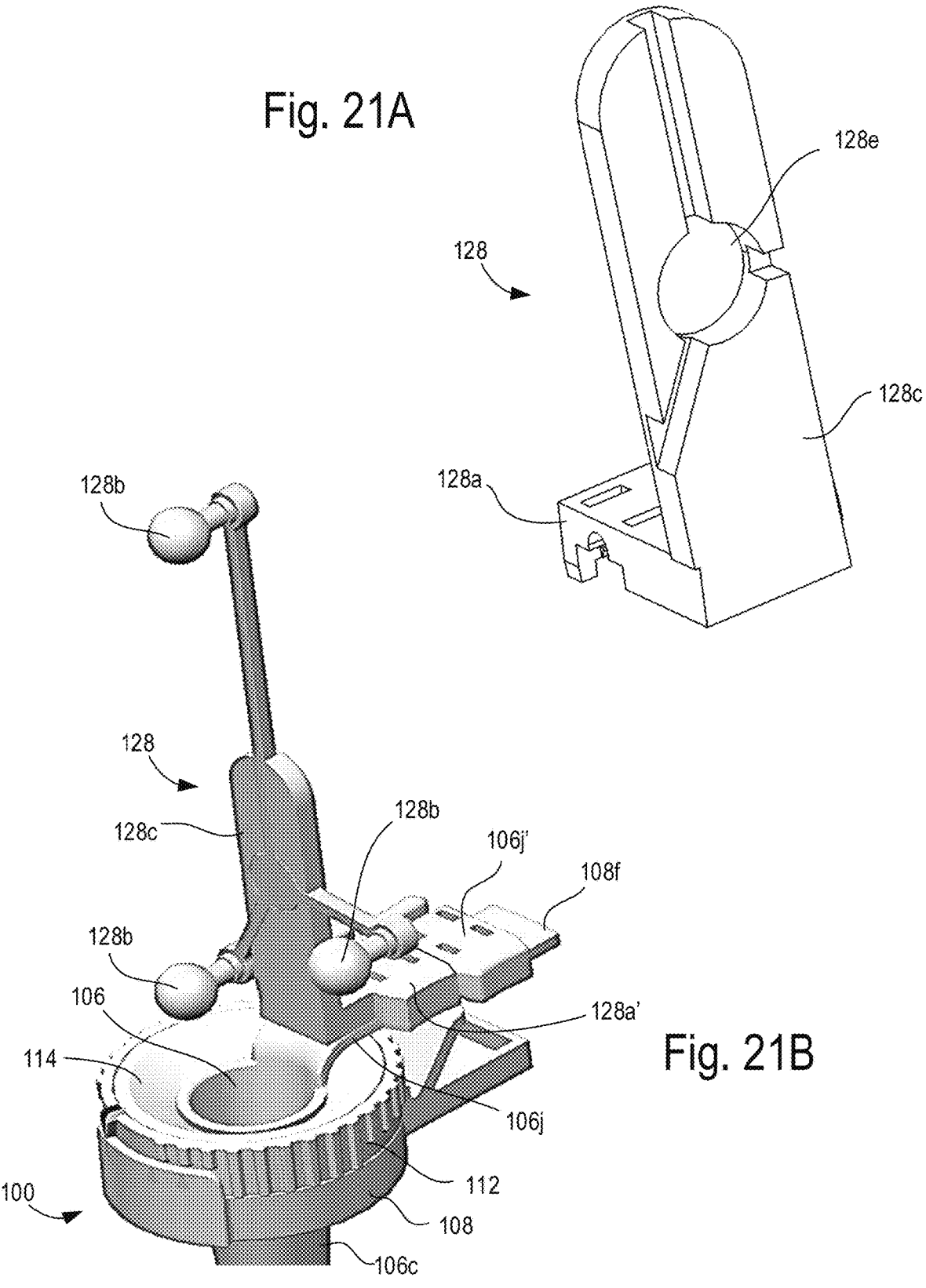
FIGS. 21A and 21B illustrate another example of a guidance arm and its connection to an expandable access port.

FIGS. 21A-21B show another embodiment of a guidance arm 128. In this case, the guidance arm 128 also includes a tab 128*a* for connecting to the expandable access port 100 (e.g., by securing to an extension 108*f*), and an array of indicators 128*b*. Here, the guidance arm 128 is provided as a two-part assembly with a base 128*c* to which the indicators 128*b* are attached. In this example, the indicators 128*b* are mounted on a frame 128*d* that fits into a corresponding opening 128*e* of the base 128*c*. Magnets or other fasteners may be used to selectively connect the frame 128*d* to the base 128*c*. This arrangement allows different arrays of indicators 128*b* to be used. For example, different frames 128*d* may be provided with indicators 128*b* at different locations corresponding to space requirements or particular requirements of different tracking systems.

FIG. 21B also shows how a guidance arm 128 can be mounted to the remainder of the expandable access port 100. In this case, the guidance arm tab 128*a* is secured by a lock 128*a'* to an introducer mounting tab 106*j*. The introducer mounting tab 106*j* is secured to a port housing extension 108*f* by its own lock 106*j'*. Thus, the guidance arm 128 may be removed separately, or in conjunction with the introducer 106.

Figure 22A:
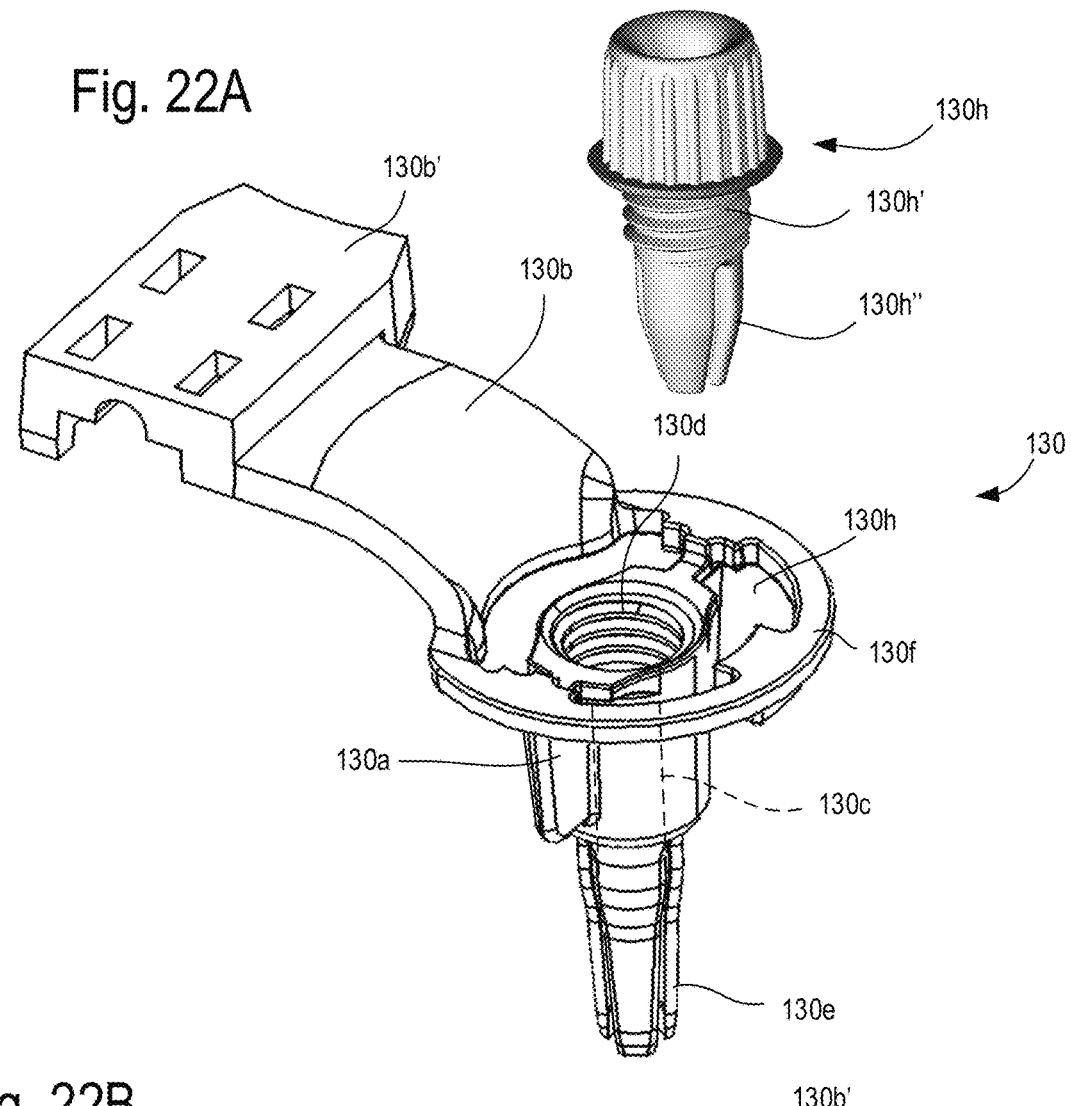
FIGS. 22A and 22B illustrate another example of a navigation probe lock.
Figure 22B:
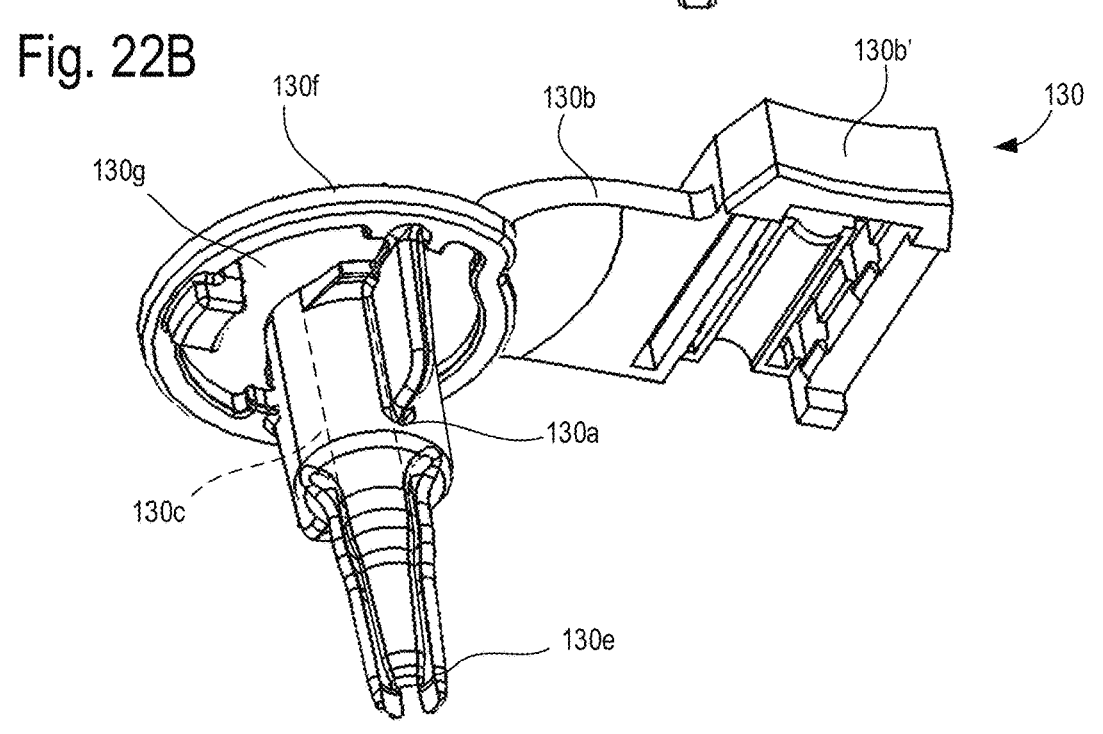
Figure 22C:
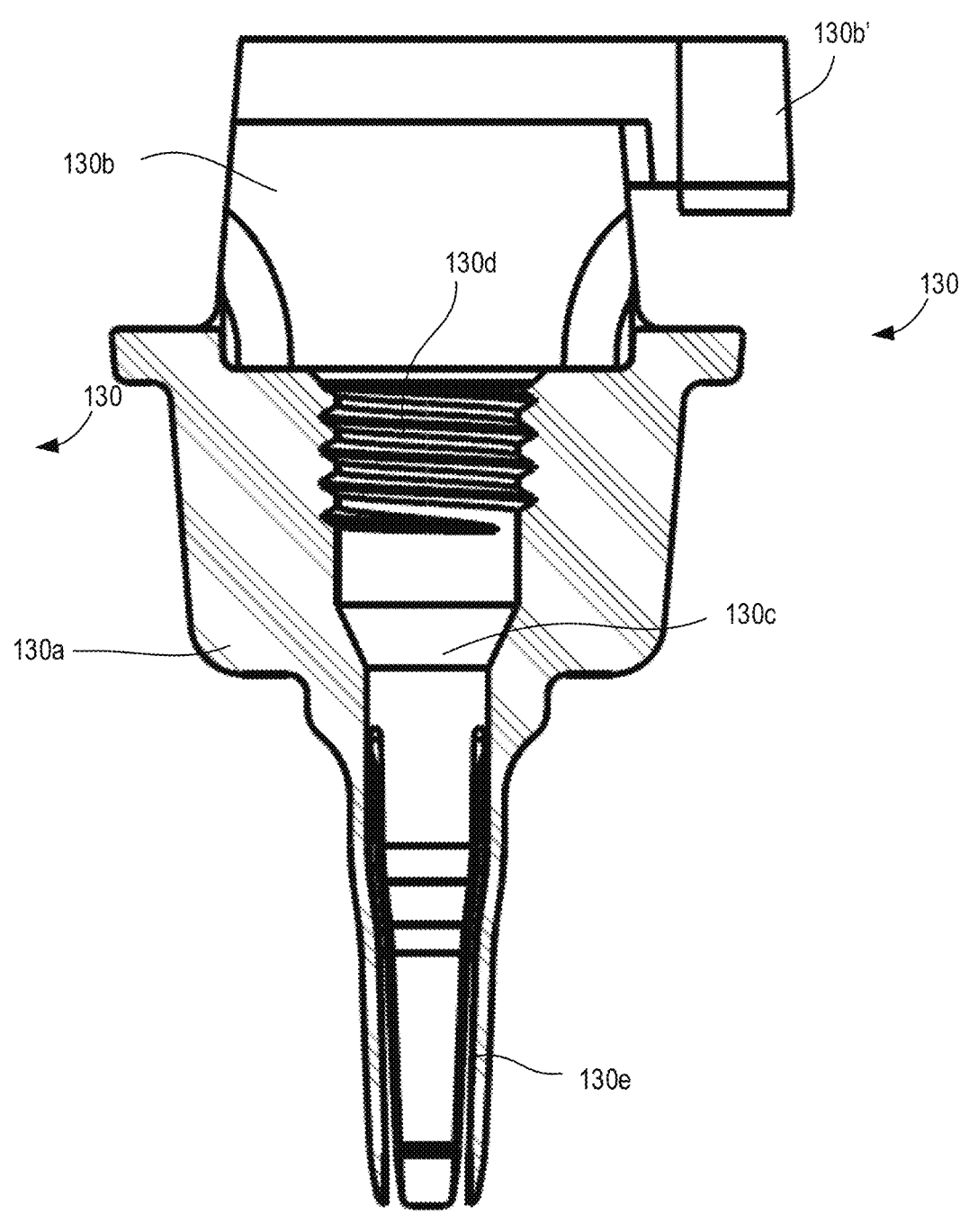
FIG. 22C is a cross-section view of the navigation probe lock of FIGS. 22A and 22B.

FIGS. 22A-22C show an example of a probe lock 130 that may be used to hold a navigation probe 126 in registration with the expandable access port 100. The probe lock 130 comprises a lock body 130*a* that extends into the introducer 106, and a tab 130*b* that is connectable to a port housing extension 108*f*. the tab 130*b* includes or is configured to secure to any suitable lock 130*b'*. The lock body 130*a* comprises a central passage 130*c* having a threaded bore 130*d* at its proximal end, and one or more flexible arms 130*e* at its distal end. The threaded bore 130*d* receives external threads 130*h'* or a lock nut 130*h*. The lock nut 130*h* has a central bore to receive the probe shaft, and tapered fingers 130*h"*. The tapered fingers 130*h"* are compressed radially inward by the inner walls of the central passage 130*c* as the nut 130*h* is threaded into the bore 130*d*, to thereby clamp the navigation probe 126 in place. The flexible arms 130*e* help to allow navigation probes with different diameters to be used in the probe lock 130 by flexing to fit the particular probe's diameters. When the parts are assembled, the central passage 130*c* may be collinear with the longitudinal axis 100*a*, but this is not strictly required. The lock body 130*a* may be connected to the tab 130*b* by a ring body 130*f* having openings 130*g* through which the surgeon can view down the introducer. Examples of various suitable probe lock features are provided in U.S. application Ser. No. 17/473, 282 (publication no. 2021/0401457), which is incorporated by reference herein.

Figures 23A, 23B:
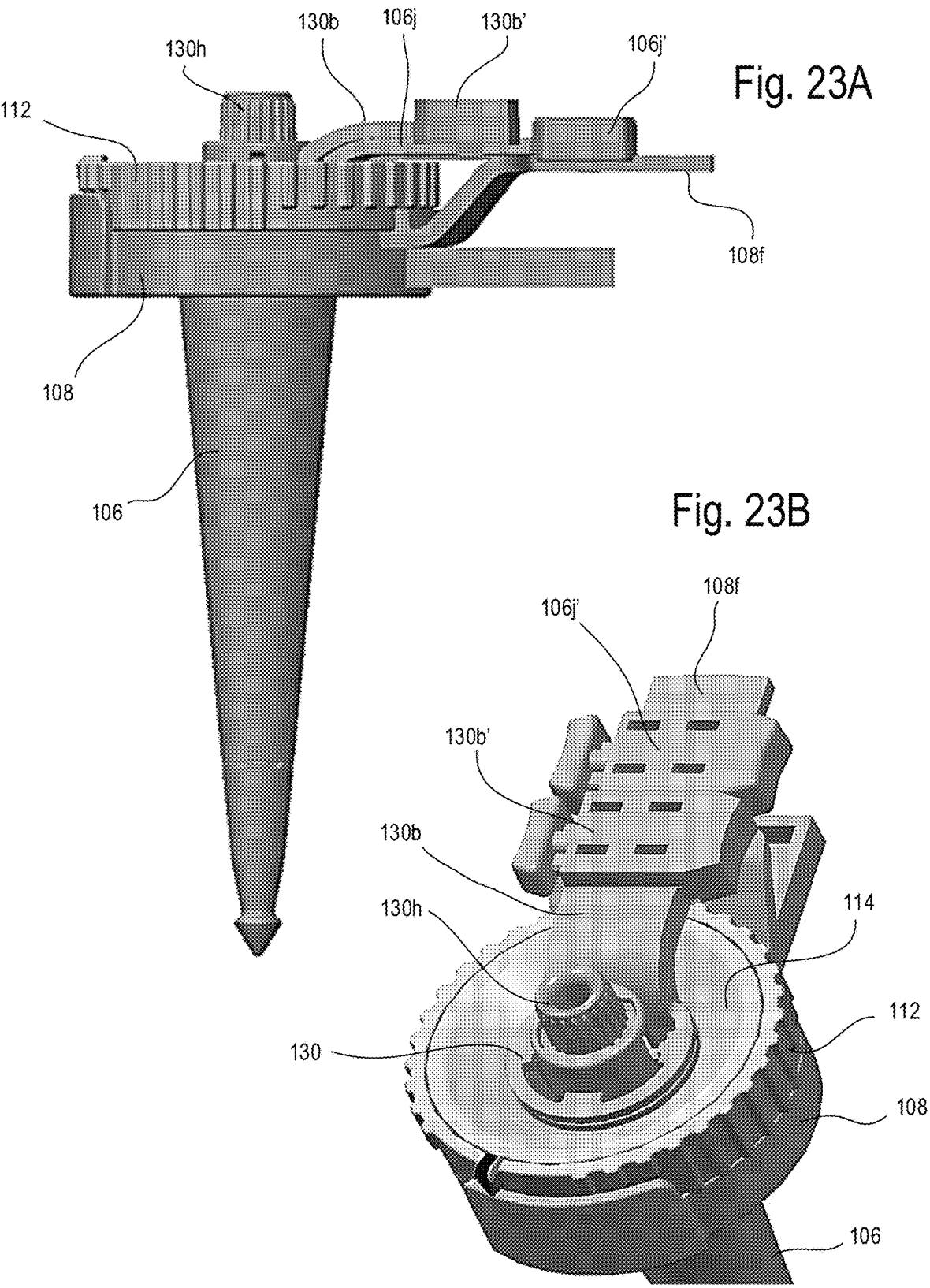
FIGS. 23A and 23B illustrate the navigation probe lock of FIGS. 22A and 22C installed with an expandable access pot.
Figure 25:
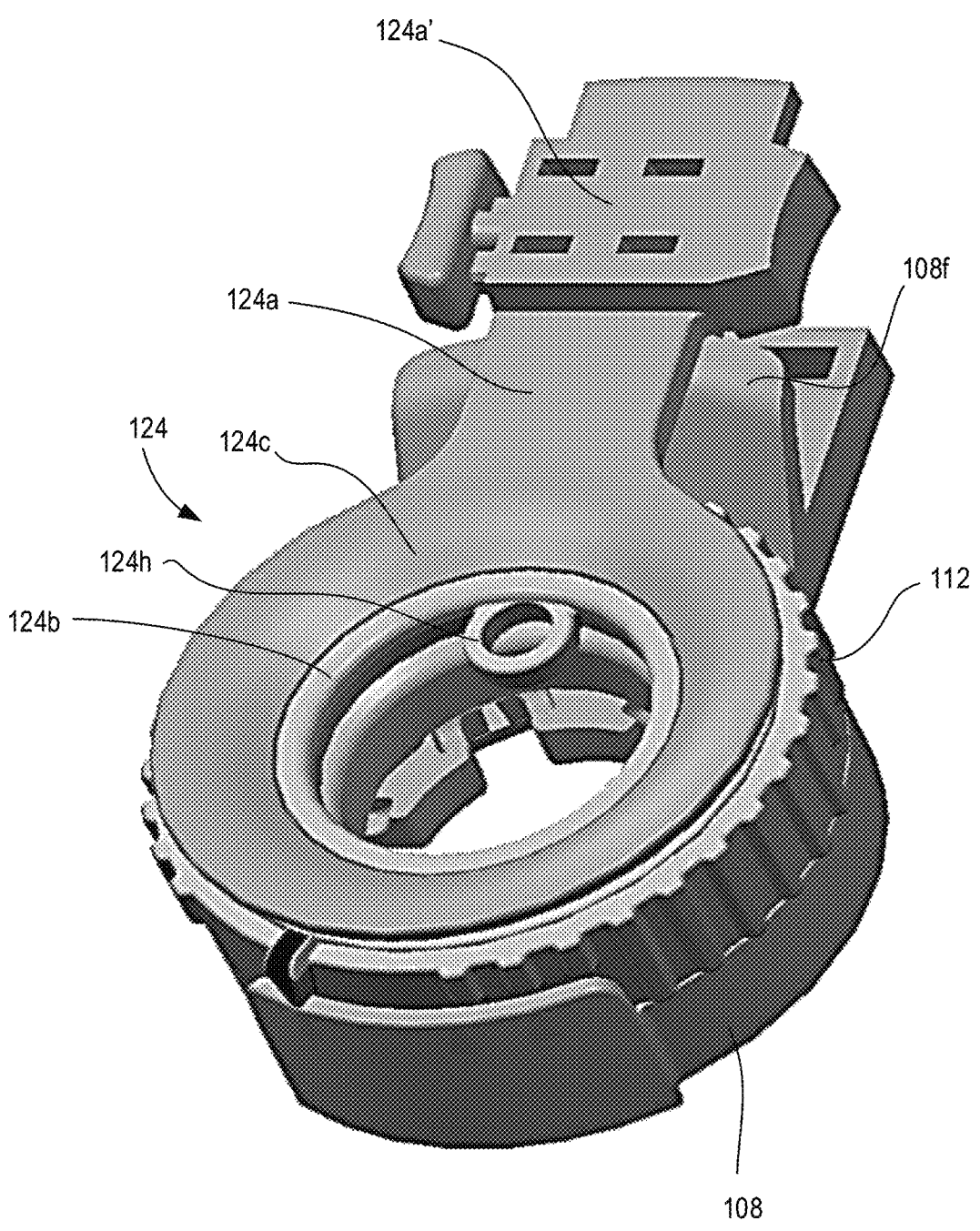
FIG. 25 shows the surgical tool mount of FIGS. 24A and 24B attached to other parts of an expandable access port.

FIGS. 23A and 23B show the probe lock 130 of FIGS. 22A-22C installed with an expandable access port. In this case, the arms 116 and membrane 118 are removed to see the shape of this alternative introducer 106, which is conical. The conical introducer 106 is dimensioned to fit closely within the space formed by the arms 116 when the arms 116 are in their collapsed position, and thereby help support the arms 116 and prevent unwanted flexure as the access port is move to the surgery site. As shown in the figures, the lock tab 130*b* may be mounted to the remainder of the assembly by connecting its lock 130*b'* to the tab 106*j* of the introducer 106. The introducer tab 106*j* is, in turn attached by a lock 106*j'* to one of the port housing extensions 108*f.* Other embodiments may connect the parts in other ways.

FIGS. 24A and 24B show another example of a surgical tool mount 124. In this case, the surgical tool mount 124 comprises a tab 124*a* that is configured to secure via a lock 124*a'* to a port housing extension 108*f,* and a ring-shaped mount body 124*c.* The mount body 124*c* has a circular central opening 124*d* that surrounds the activation assembly opening 102*a,* and a connector 124*b* that fits within the central opening 124*d.* The connector 124*b* preferably is configured to rotate within the central opening 124*d.* For example, the connector 124*b* may have an outer rim 124*e* that fits on top of an inner rim 124*f* formed in the central opening 124*d,* and tabs 124*g* that surround the bottom of the inner rim 124*f.* The outer rim 124*e* and tabs 124*g* form an annular space that captures the inner rim 124*f* and prevents the connector 124*b* from separating from the mount body 124*c,* while still allowing the connector 124*b* to rotate within the mount body 124*c.* A ring-shaped connector 124*b* such as shown is expected to provide smooth rotation by the mating circular surfaces, and allows the surgeon to position the endoscope 132 or other device at the most convenient location. In addition, the connector 124*b* may be made without any kind of locking device, so that it is freely movable at all times as the need might arise during surgery. Travel stops may be provided, however, to limit rotation to a specific range. Friction between the connector 124*b* and mount body 124*c* can hold the connector 124*b* in a fixed location until the surgeon applies a force to rotate the connector 124*b.* While free movability is desired in some embodiments, in other cases, a lock, such as a thumb screw, may be provided to hold the connector 124*b* at a fixed location.

The connector 124*b* may include any suitable mechanism for holding any one or more types of surgical instrument. For example, the connector 124*b* may have a tool connector in the form of an inner ring 124*h* that is dimensioned to hold an endoscope 132. In this case, the inner ring 124*h* is located at the outer radial edge of the connector 124*b,* so that the instrument, when installed, is offset from the longitudinal axis 100*a.* For example, in the shown embodiment, the inner ring 124*h* is radially offset from the central axis of the opening 124*i.* The remainder of the connector 124*b* has an opening 124*i* that is located within the central opening 124*d* of the mount body 124*c* and preferably surrounds the longitudinal axis 100*a.* In this way, the instrument can be positioned at any desired angular location about the longitudinal axis 100*a,* and still allow access for other instruments to be used within the expandable port 100.

The inner ring 124*h* (or other types of tool connector) may use any suitable lock or holding mechanism to hold the instrument. For example, the inner ring 124*h* may comprise a circular opening that is dimensioned to snugly fit the outer surface of the endoscope 132 such that the endoscope 132 can be moved distally and proximally by the surgeon by hand, while still holding the endoscope in any position when the surgeon releases the endoscope 132. The inner ring 124*h* also may have a radial slot such that the inner ring 124*h* is defined by two arms, in which case the arms may be flexible to provide a resilient force to grip a surgical instrument positioned between the arms. A separate lock device, such as a locking screw, may also be used. Materials, such an overmolded high-friction elastomer, may be used to modify the operation of the inner ring 124*h.* Other embodiments may use clamps compression nut arrangements (e.g., like threaded bore 130*d* and nut 130*h*) or the like. Other alternatives and embodiments will be apparent to persons of ordinary skill in the art in view of the present disclosure.

Figure 26:
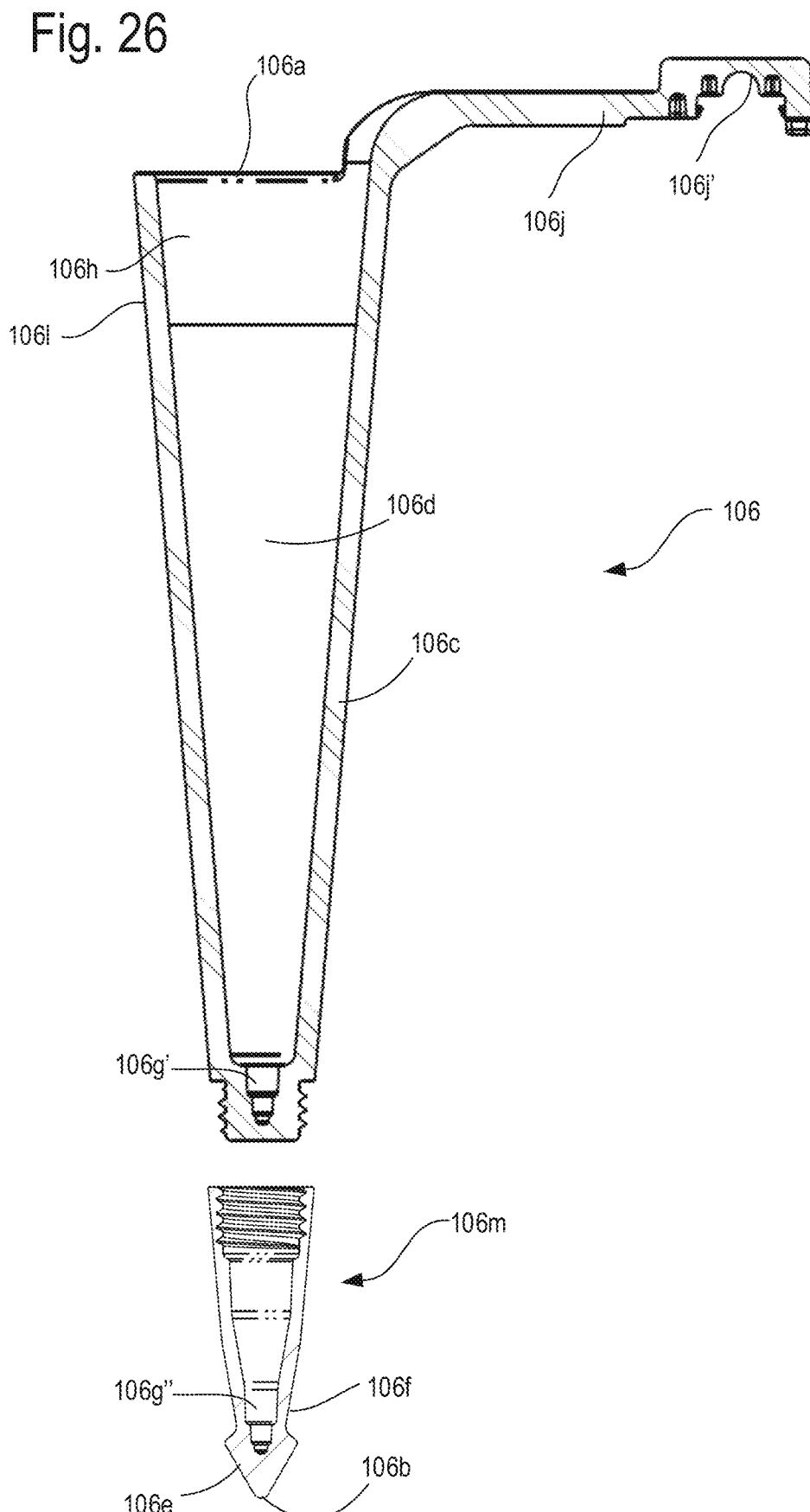
FIG. 26 is a cross section view of an exemplary introducer.

FIG. 26 illustrates the exemplary introducer 106 of FIGS. 23A and 23B in cross section to show additional optional details. The introducer 106 is similar to the one in FIGS. 11A-11C, but has an integral lock 106*j',* a continuous conical tapered wall 106*c* forming the cannula 106*d,* and a separately formed tip unit 106*m.* The tip unit 106*m* includes the introducer tip 106*e,* and optionally an annular recess 106*f.* The tip unit 106*m* is configured to permanently or removable attach to the rest of the introducer 106. In the shown example, the tip unit 106*m* has internal threads 106*n* that engage external threads 106*o* on the tapered wall 106*c.* In other cases, snap fitments may be used (e.g., a non-reversible snap connector), or the tip unit 106*m* may be secured by adhesives, welding, and so on.

The tip unit 106*m* is provided to allow the use of different navigation devices with different probe shaft lengths. For example, in the shown embodiment, the introducer cannula 106*d* terminates to form a probe tip receiver 106*g'* at the end of the conical wall 106*c.* In use, the probe shaft tip seats in the probe tip receiver 106*g',* and is offset from the distal introducer end 106*b* by a fixed, known distance. This distance can be used to offset the calibration of the navigation system. Thus, in those cases in which a probe shaft is not long enough to extend to the distal introducer end 106*b,* the two-part introducer shown of FIG. 26 can be used to account for the shorter length.

The introducer 106 of FIG. 26 can also be modified in various ways. For example, the introducer cannula 106*d* may terminate at a simple opening that allows the navigation probe shaft to pass through to be seated in a probe tip receiver 106*g''* in the tip unit 106*m.* It is also envisioned that introducers 106 having various constructions may be provided as a kit for use in different configurations as required by the particular circumstances. For example, an introducer tip unit 106*m* may be provided with one or more introducer bodies as shown (i.e., having a probe tip receiver 106*g'*), along with one or more introducer bodies that has have openings to allow the probe shaft pass into the tip unit 106*m.* This may be helpful, for example, to allow the surgeon to select between different introducer lengths and configurations for the particular case, and then secure the tip to the desired introducer body for use in surgery. Other alternatives and embodiments will be apparent to persons of ordinary skill in the art in view of the present disclosure.

Having explained details of embodiments of expandable access ports 100, the operation will be understood. For example, the expandable access port 100 may be operated by connecting the introducer 106 to the activation assembly 102 with the introducer tip 106*e* positioned distally beyond the distal arm ends 116*d,* rotating the activation ring 112 to move the activation arms 116 to the first (contracted) positions, then inserting the assembled expandable access port 100 to the surgery site, operating the activation ring 112 to move the activation arms 116 to the second (expanded) positions, removing the introducer 106, and performing a surgical procedure through the expanded 104. Additional optional steps include, but are not limited to, installing a navigation probe 126 in the introducer 106 or attaching a guidance arm 128 to the activation assembly 102 and using the navigation probe 126 or guidance arm 128 to guide the expandable access port 100 into place using stereotactic navigation, as known in the art. Also, a navigation probe 126 may be attached to the introducer 106 to guide the expandable access port 100 during initial insertion, and a guidance arm 128 may be used to ensure continued placement while the expandable access port 100 is used for the surgical procedure or to reposition the expandable access port 100 during surgery. Other optional steps include operating a light 120 to illuminate the surgery site, and mounting a surgical tool mount 124 to the activation assembly 102 to hold or guide additional surgical instruments, and the like.

It will also be understood that method of manufacturing an expandable access port 100 are also encompassed by this disclosure. For example, an expandable access port 100 may be manufactured by: providing an activation assembly 102 defining an activation assembly opening 102a surrounding a longitudinal axis 100a; providing a plurality of activation arms 116 arranged around the longitudinal axis 100a, each activation arm 116 in a distal direction D from a respective proximal arm end 116g to a respective distal arm end 116d, with each respective distal arm end 116d being movably connected to the activation assembly 102 and movable, upon operation of the activation assembly 102, between a respective first position in which each respective distal arm end 116d is spaced a respective first distance D1 from the longitudinal axis 100a, and a respective second position in which each respective distal arm end 116d is spaced a respective second distance D1 from the longitudinal axis 100a, wherein each respective second distance D2 is greater in magnitude than each respective first distance D1; and overmolding a membrane 118 onto the plurality of activation arms 116, the membrane 118 extending in the distal direction D from a proximal membrane end 118a adjacent the activation assembly 102 to a distal membrane end 118b adjacent the respective distal arm ends 116d, wherein the membrane 118 comprises a flexible material that is expandable to permit the plurality of activation arms 116 to move from the respective first positions to the respective second positions. Optional steps to this method include, but are not limited to, forming the membrane 118 from materials and with dimensions and other properties as described above, overmolding the membrane 118 into slots 116e formed on the activation arms 116, capturing a light 120 in place within a slot 116e, overmolding the membrane 118 into a structure comprising ribs 118d on the outer radial surface 116h of each activation arm 116 and walls 118e between each adjacent pair of ribs 118d, and overmolding a lip 118c around the distal arm ends 116d.

The various parts of the expandable access port may be made of any material that is suitable for the purposes herein, and has adequate biocompatibility for use in a surgical setting. For example, the activation arms 116 and membrane 118 of the expandable port 104 may be constructed as described above, and may be transparent or semi-transparent to allow visualization of the brain tissue surrounding the expandable port 104. Similarly, the introducer 106, port housing 108, lock ring 110, activation ring 112 and activation ring cover 114 may be constructed of polycarbonate or other materials, and may be transparent or opaque.

The present disclosure provides a number of exemplary embodiments of the invention defined by the appended claims. The description of such embodiments is not intended to limit the scope of the claims beyond what is defined in the claims. It will also be understood that, while embodiments may provide particular advantages in certain cases, the scope of the claims is not limited to embodiments providing any particular advantage or functionality. It will further be appreciated that other embodiments encompassed by the claims may diverge from those described herein in both appearance and functionality, and the various features of particular embodiments described herein may be used with other embodiments without departing from the scope of the claims.

The invention claimed is:

1. An expandable surgical access port comprising:
an activation assembly defining an activation assembly opening surrounding a longitudinal axis, the activation assembly comprising:
an activation arm mounting body defining an activation arm mounting body opening surrounding at least a portion of the activation assembly opening, the activation arm mounting body comprising a plurality of pivot locations surrounding the longitudinal axis, each pivot location defining a respective pivot axis extending in a plane perpendicular to the longitudinal axis and not intersecting the longitudinal axis, and
an activation ring mounted to the activation arm mounting body and defining an activation ring opening surrounding at least a portion of the activation assembly opening, wherein the activation ring is rotatable about the longitudinal axis relative to the activation arm mounting body, to rotate between a first activation ring position and a second activation ring position, wherein the activation ring remains at a fixed location along the longitudinal axis throughout a full range of movement between the first activation ring position and the second activation ring position;
a plurality of activation arms arranged around the longitudinal axis, each activation arm extending in a distal direction from a respective proximal arm end to a respective distal arm end, with each respective proximal arm end being pivotally connected to the activation assembly at a respective one of the plurality of pivot locations, wherein each activation arm is pivotable about the respective pivot axis, upon movement of the activation ring from the first activation ring position to the second activation ring position, from a respective first arm position in which each respective distal arm end is spaced a respective first distance from the longitudinal axis, and a respective second arm position in which each respective distal arm end is spaced a respective second distance from the longitudinal axis, wherein each respective second distance is greater in magnitude than each respective first distance;
a membrane surrounding the plurality of activation arms and extending from a proximal membrane end adjacent the activation assembly to a distal membrane end, wherein the membrane comprises a flexible material that is expandable to permit the plurality of activation arms to move from the respective first positions to the respective second positions.

2. The expandable surgical access port of claim 1, wherein the activation arm mounting body comprises:
a port housing defining a port housing opening surrounding at least a portion of the activation assembly opening and comprising a plurality of first pivot recesses; and
a lock ring defining a lock ring opening surrounding at least a portion of the activation assembly opening and comprising a plurality of second pivot recesses;
wherein the lock ring is secured to the port housing with each of the first pivot recesses adjacent to a respective one of the second pivot recesses to define a respective one of the pivot locations.

3. The expandable surgical access port of claim 2, wherein the activation ring is attached to the port housing by a rotatable connection.

4. The expandable surgical access port of claim 3, wherein the rotatable connection comprises a plurality of sliding tabs and corresponding sliding tab receivers.

5. The expandable surgical access port of claim 1, wherein each pivot location comprises a respective activation arm port extending in the distal direction along the longitudinal axis from the respective pivot axis, and each activation arm is movable within at least a portion of each activation arm port.

6. The expandable surgical access port of claim 1, wherein the activation ring is rotatable in a first direction about the longitudinal axis relative to the activation arm mounting body to drive the activation arms from their respective first arm positions to their respective second arm positions, and rotatable in a second direction about the longitudinal axis relative to the activation arm mounting body to drive the activation arms from their respective second arm positions to their respective first arm positions.

7. The expandable surgical access port of claim 6, wherein the activation ring comprises a plurality of cam slots, each cam slot extending about a portion of the activation ring opening from a respective first cam slot end to a respective second cam slot end, wherein each respective second cam slot end is closer to the longitudinal axis than each respective first cam slot end.

8. The expandable surgical access port of claim 7, wherein:
   each activation arm comprises a respective pivot, and a respective cam follower extending in the proximal direction from the respective pivot and into a respective one of the cam slots; and
   wherein rotation of the activation ring from the first activation ring position to the second activation ring position causes each respective cam follower to move from the respective first cam slot end to the respective second cam slot end to thereby move the respective activation arm from the respective first arm position to the respective second arm position.

9. The expandable surgical access port of claim 8, wherein each pivot location comprises a respective cam follower port extending in a proximal direction, opposite the distal direction, along the longitudinal axis from the respective pivot axis, and each cam follower extends through a respective one of the cam follower ports.

10. The expandable surgical access port of claim 1, wherein the activation ring comprises a tapered inlet surface reducing in diameter in the distal direction.

11. The expandable surgical access port of claim 1, wherein each activation arm comprises:
   a respective pivot located at the respective proximal arm end and rotationally secured a respective one of the pivot locations; and
   a respective straight elongated body extending from the respective pivot to the respective distal arm end;
   wherein the respective distal arm end of each activation arm comprises an inward bend towards the longitudinal axis.

12. The expandable surgical access port of claim 1, wherein at least one of the activation arms comprises a respective light located at the respective distal arm end.

13. The expandable surgical access port of claim 12, wherein the at least one activation arm comprises a respective slot extending at least partially between the respective proximal arm end and the respective distal arm end from a proximal slot end to a distal slot end, and wherein the respective light is located at the respective distal slot end.

14. The expandable surgical access port of claim 13, wherein the at least one activation arm comprises one of a light guide and an electrical wire extending along the slot from the proximal slot end to the light.

15. The expandable surgical access port of claim 14, wherein the proximal slot end is at the respective pivot of the respective activation arm.

16. The expandable surgical access port of claim 13, wherein the respective slot is located in a respective outer radial surface of the respective activation arm.

17. The expandable surgical access port of claim 1, wherein each pivot axis is tangential to the longitudinal axis.

18. The expandable surgical access port of claim 1, wherein the activation ring is positioned on a proximal side of the activation arm mounting body.

19. The expandable surgical access port of claim 1, wherein the activation ring comprises an outer surface defining a grip, wherein the grip is larger in a respective diameter than a respective diameter of an adjacent portion of the activation arm mounting body.

20. The expandable surgical access port of claim 1, wherein the activation ring comprises an outer surface comprising knurling.

21. The expandable surgical access port of claim 1, wherein the activation ring mounting body further comprises one or more extensions located at or proximally from a proximal side of the activation ring.

22. The expandable surgical access port of claim 1, wherein the activation ring mounting body further comprises one or more extensions configured to connect to one or more of: a clamp, a navigation device, and a surgical tool mount.

23. The expandable surgical access port of claim 1, further comprising a position indicator configured to identify a position of the activation ring relative to the activation arm mounting body.

24. The expandable surgical access port of claim 1, wherein:
   the activation arm mounting body comprises one or more body position indicators; and
   the activation ring comprises one or more ring position indicators;
   wherein the one or more body position indicators and the one or more ring position indicators are aligned when the activation ring is at one or more predetermined positions relative to the activation arm mounting body.

25. The expandable surgical access port of claim 1, wherein the activation ring comprises an outer surface defining a grip, wherein the grip is larger in a respective diameter than a respective diameter of an adjacent portion of the activation arm mounting body.

26. The expandable surgical access port of claim 1, further comprising depth markers spaced along the longitudinal axis and visible on or through the membrane.

27. The expandable surgical access port of claim 1, further comprising a surgical tool mount configured to secure to the activation arm mounting body, the surgical tool mount comprising:
   a ring-shaped mount body defining a circular opening; and
   a ring-shaped connector mounted in the opening and configured to rotate about a central axis of the circular opening, the ring-shaped connector having a tool lock radially offset from the central axis of the circular opening.

28. The expandable surgical access port of claim 27, wherein the ring-shaped connector is freely rotatable about at least a portion of the central axis of the circular opening
and does not comprise a rotation lock.

* * * * *